US010738125B2

(12) United States Patent
Goubier et al.

(10) Patent No.: US 10,738,125 B2
(45) Date of Patent: Aug. 11, 2020

(54) ANTI-CD25 ANTIBODY AGENTS

(71) Applicants: Tusk Therapeutics Ltd., Hertfordshire (GB); Cancer Research Technology Limited, London (GB)

(72) Inventors: Anne Goubier, Hertfordshire (GB); Beatriz Goyenechea Corzo, Hertfordshire (GB); Josephine Salimu, Hertfordshire (GB); Kevin Moulder, Hertfordshire (GB); Pascal Merchiers, Hertfordshire (GB); Mark Brown, Hertfordshire (GB); Sergio Quezada, London (GB); James Geoghegan, Lyme, NH (US); Bianka Prinz, Lebanon, NH (US)

(73) Assignees: Tusk Therapeutics Ltd., London (GB); Cancer Research Technology Limited, Hertfordshire (GB)

( * ) Notice: Subject to any disclaimer, the term of this patent is extended or adjusted under 35 U.S.C. 154(b) by 0 days.

(21) Appl. No.: 16/352,703

(22) Filed: Mar. 13, 2019

(65) Prior Publication Data
US 2019/0322752 A1 Oct. 24, 2019

Related U.S. Application Data

(60) Provisional application No. 62/642,218, filed on Mar. 13, 2018, provisional application No. 62/642,230, filed on Mar. 13, 2018, provisional application No. 62/642,232, filed on Mar. 13, 2018, provisional application No. 62/642,243, filed on Mar. 13, 2018, provisional application No. 62/642,248, filed on Mar. 13, 2018.

(30) Foreign Application Priority Data

Mar. 13, 2018 (GB) .................... 1804027.9
Mar. 13, 2018 (GB) .................... 1804028.7
Mar. 13, 2018 (GB) .................... 1804029.5
Mar. 13, 2018 (WO) ............. PCT/EP2018/056312

(51) Int. Cl.
C07K 16/28 (2006.01)
A61K 39/395 (2006.01)
A61P 35/00 (2006.01)
A61K 39/00 (2006.01)
A61P 35/02 (2006.01)
C07K 14/55 (2006.01)
C12N 15/85 (2006.01)

(52) U.S. Cl.
CPC .... *C07K 16/2866* (2013.01); *A61K 39/39566* (2013.01); *A61P 35/00* (2018.01); *A61P 35/02* (2018.01); *C07K 14/55* (2013.01); *C07K 16/2818* (2013.01); *C07K 16/2827* (2013.01); *C12N 15/85* (2013.01); *A61K 2039/505* (2013.01); *A61K 2039/507* (2013.01); *C07K 2317/20* (2013.01); *C07K 2317/21* (2013.01); *C07K 2317/31* (2013.01); *C07K 2317/32* (2013.01); *C07K 2317/34* (2013.01); *C07K 2317/41* (2013.01); *C07K 2317/52* (2013.01); *C07K 2317/54* (2013.01); *C07K 2317/55* (2013.01); *C07K 2317/565* (2013.01); *C07K 2317/60* (2013.01); *C07K 2317/622* (2013.01); *C07K 2317/73* (2013.01); *C07K 2317/732* (2013.01); *C07K 2317/76* (2013.01); *C07K 2317/92* (2013.01); *C12N 2015/8518* (2013.01)

(58) Field of Classification Search
None
See application file for complete search history.

(56) References Cited

U.S. PATENT DOCUMENTS

| 2008/0025947 A1 | 1/2008 | Gillies et al. |
| 2014/0099254 A1 | 4/2014 | Chang et al. |
| 2016/0135925 A1 | 5/2016 | Mason et al. |
| 2019/0135925 A1 | 5/2019 | Quezada et al. |

FOREIGN PATENT DOCUMENTS

| WO | WO-2004/045512 A2 | 6/2004 |
| WO | WO-2004/074437 A2 | 9/2004 |
| WO | WO-2005/115451 A2 | 12/2005 |
| WO | WO-2005/123780 A2 | 12/2005 |
| WO | WO-2006/050172 A2 | 5/2006 |
| WO | WO-2006/108670 A2 | 10/2006 |
| WO | WO-2011/077245 A2 | 6/2011 |
| WO | WO-2014/145907 A1 | 9/2014 |
| WO | WO-2016/011264 A1 | 1/2016 |

(Continued)

OTHER PUBLICATIONS

Arce Vargas, F. et al., Fc-optimized Anti-CD25 depletes tumour-inflitrating regulatory T cells and synergizes with PD-1 blockade to eradicate established tumours, Immunity, 46: 577-586 (2017).

(Continued)

*Primary Examiner* — Daniel E Kolker
*Assistant Examiner* — Jegatheesan Seharaseyon
(74) *Attorney, Agent, or Firm* — Choate, Hall & Stewart LLP; Brenda Herschbach Jarrell; Michael L. Vetter

(57) ABSTRACT

The present disclosure provides antibody sequences found in antibodies that bind to human CD25. In particular, the present disclosure provides sequences of anti-human CD25 antibodies, which do not block the binding of CD25 to IL-2 or IL-2 signalling. Antibodies and antigen-binding portions thereof including such sequences can be used in pharmaceutical composition and methods of treatment, in particular for treating cancer.

25 Claims, 11 Drawing Sheets
Specification includes a Sequence Listing.

(56) References Cited

FOREIGN PATENT DOCUMENTS

| WO | WO-2016/021720 A1 | 2/2016 |
| WO | WO-2017/174331 A1 | 10/2017 |
| WO | WO-2018/167104 A1 | 9/2018 |
| WO | WO-2019/008386 A1 | 1/2019 |
| WO | WO-2019/175215 A1 | 9/2019 |
| WO | WO-2019/175216 A1 | 9/2019 |
| WO | WO-2019/175217 A1 | 9/2019 |
| WO | WO-2019/175220 A1 | 9/2019 |
| WO | WO-2019/175222 A1 | 9/2019 |
| WO | WO-2019/175223 A1 | 9/2019 |
| WO | WO-2019/175224 A1 | 9/2019 |
| WO | WO-2019/175226 A1 | 9/2019 |

OTHER PUBLICATIONS

Comes, A. et al., CD25+ Regulatory T cell depletion augments immunotherapy of micrometastases by an IL-21-Secreting Cellular Vaccine, Journal of Immunology, 176: 1750-175 (2006).

Dantal, J. et al., Cluster-Function Relationship of Rat-Antimouse P55 IL-2 Receptor Monoclonal Antibodies, Transplantation, 52: 110-115 (1991).

Ferrini, S. et al., Regulatory T cell depletion/blockade in combination with IL-21-based immunotherapy: a pre-clical[ sic ] study, Cancer Immunol Immunother., 57 (Suppl 1): S1-S53, p. 16 P050 (2008).

Furness, A.J.S. et al., Impact of tumour microenvironment and Fc receptor on the activity of immunomodulatory antibodies, Trends in Immunology, 35(7): 290-298 (2014).

Goudin, N. et al., Depletion of Regulatory T Cells Induces High Nos. Of Dendritic Cells and Unmasks a Subset of Anti-tumour CD8+CD11c+ PD-1lo Effector T Cells, PLOS One, 11(6): 1-11 (2016).

Goudine, N. et al., Depletion of Regulatory T Cells Induces High Numbers of Dendritic Cells and Unmasks a Subset of Anti-Tumour $CD8^+CD11c^+$ PD-$1^{lo}$ Effector T Cells, PLoS One, 11(6):e0157822 (2016).

Grauer et al., CD41FoxP31 regulatory T cells gradually accumulate in gliomas dming tumor growth and efficiently suppress antiglioma immune responses in vivo, Int. J. Cancer, 121:95-105 (2007).

Gubbels, J. et al., Ab-IL2 fusion proteins mediate NK cell immune synapse formation by polarizing CD25 to the target cell-effector cell interface, Cancer Immunol Immunother, 60:1789-1800 (2011).

Huss, D.J. et al., Anti-CD25 monoclonal antibody Fc variants differentially impact regulatory T cells and immune homeostasis, Immunology, 148(3): 276-286 (2016).

International Search Report for PCT/EP2017/056469, 6 pages (dated May 2, 2017).

International Search Report for PCT/EP2018/056312, (FC-Optimized Anti-CD25 for Tumour Specific Cell Depletion, filed Mar. 13, 2018) issued by ISA/EPO, 6 pages (Jun. 14, 2018).

Kohm, A.P. et al., Cutting edge: anti-CD25 monoclonal antibody injection results in the functional inactivation, not depletion, of CD4+CD25+T regulatory cells, J Immunol, 176: 3301-3305 (2006).

Nimmerjahn, F. et al., Fc[gammag]R dependent mechanisms of cytotoxic, agonistic, and neutralizing antibody activities, Trends in Immunology, 36(6): 325-336 (2015).

Ortega, G. et al., The murine IL 2 receptor. I. Monoclonal antibodies that define distinct functional epitopes on activated T cells and react with activated B cells, Journal of Immunology, 133: 1970-1975 (1984).

Poirier, M-D. et al., A combination of systemic and intracranial anti-CD25 immunotherapy elicits a long-time survival in murine model of Glioma, Journal of Oncology, 8 pages (2009).

Sampson, J.H. et al., A Pilot Study of IL-2Ra Blockade during Lymphopenia Depletes Regulatory T-cells and Correlates with Enhanced Immunity in Patients with Glioblastoma, PLOS One, 12 pages (2012).

Sampson, J.H. et al., A Pilot Study of IL-2Rα Blockade during Lymphopenia Depletes Regulatory T-cells and Correlates with Enhanced Immunity in Patients with Glioblastoma, PLoS One, 7(2):e31046 (2012).

Stewart, R. et al., the role of Fc gamma receptors in the activity of immunomodulatory antibodies for cancer, Journal of ImmunoTherapy of Cancer 2014, 2(29): 1-10 (2014).

Sutmuller, R.P.M. et al., Synergism of cytotoxic T lymphocyte-associated Antigen 4 blockade and depletion of CD25+ regulatory T cells in Antitumour therapy reveal alternative pathways for suppression of autoreactive cytotoxic T lymphocyte responses, Journal of Experimental Medicine, 194(6): 823-832 (2001).

Written Opinion for PCT/EP2017/056469, 7 pages (dated May 2, 2017).

Written Opinion for PCT/EP2018/056312, (FC-Optimized Anti-CD25 for Tumour Specific Cell Depletion, filed Mar. 13, 2018) issued by ISA/EPO, 9 pages (Jun. 14, 2018).

Zelenay, S. and Demengeot, J., Comment on "Cutting Edge: Anti-CD25 Monoclonal Antibody Injection Results in the Functional Inactivation, Not Depletion, of CD4+CD25+T Regulatory Cells", J Immunol, 177: 2036-2037 (2006).

Zhang, M. et al., Activating Fc Receptors Are Required for Antiumour Efficacy of the Antibodies Directed toward CD35 in a Murine Model of Adult T-Cell Leukemia, Cancer Research, 64: 5825-5829 (2004).

Zhang, Y. et al., Daclizumab reduced CD25 levels ion T cells through monocyte-mediated trogocytosis, Mult Scler., 20(2): 156-164 (2014).

International Search Report for PCT/GB2018/051923, mailed from the ISA/EP, 6 pages (dated Aug. 24, 2018).

Written Opinion for PCT/GB2018/051923, mailed from the ISA/EP, 9 pages (dated Aug. 24, 2018).

Morris, J. et al., Receptor-Directed Therapy of T-Cell Leukemias and Lymphomas, Journal of Immunotoxicology, 5:235-248 (2008).

Phillips, K. et al., IL-2Rα-Directed Monoclonal Antibodies Provide Effective Therapy in a Murine Model of Adult T-Cell Leukemia by a Mechanism Other than Blockade of IL-2/IL-2 Rα Interaction, Cancer Research, 60(24):6977-84 (2000).

Salimu, J. et al. Abstract 2787: Generation of first-in-class anti-CD25 antibodies depleting Treg without interfering with IL2 signalling for cancer therapies, Proceedings: AACR Annual Meeting 2018; Apr. 14-18, 2018, Cancer Research, 78(13 Supp,):Abstract 2787, 4 pages (2018).

Solomon, I. et al., A novel non-IL2 blocking anti-CD25 depleting antibody has single dose/single agent activity against established tumors, best available copy of Poster presented at AACR Conference held Apr. 14-18, 2018.

Solomon, I. et al., Abstract A3143: A Novel approach to deplete Treg cells using non-IL-2 blocking anti-CD25-targeting antibodies leads to complete rejection of established tumors, Proceedings: AACR Annual Meeting 2018; Apr. 14-18, 2018, Cancer Research, 78(13 Supp,):Abstract A3143, 4 pages (2018).

Third Party Submissions filed Feb. 27, 2020, in U.S. Appl. No. 16/494,962 (28 pages).

aCD25-a-674-HCDR1
YTFTSYYMH aCD25-a-674-HCDR2
IINPSGGSTSYAQKFQG aCD25-a-674-HCDR3
ARGGAEYIPAEYFQH aCD25-a-674-HCDR123:
QVQLVQSGAEVKKPGASVKVSCKASGYTFTSYYMHWVRQAPGQGLEWMGIINPS
GGSTSYAQKFQGRVTMTRDTSTSTVYMELSSLRSEDTAVYYCARGGAEYIPAEYF
QHWGQGTLVTVSS aCD25-a-674-LCDR1
RASQSVSSYLA aCD25-a-674-LCDR2
DASNRAT aCD25-a-674-LCDR3
QQRPFLPT aCD25-a-674-LCDR123
EIVMTQSPATLSLSPGERATLSCRASQSVSSYLAWYQQKPGQAPRLLIYDASNRAT
GIPARFSGSGSGTDFTLTISSLEPEDFAVYYCQQRPFLPTFGGGTKVEIK

MDSYLLMWGL  LTFIMVPGCQ  AELCDDDPPE  IPHATFKAMA  YKEGTMLNCE 60          70          80          90         100

CKRGFRRIKS  GSLYMLCTGN  SSHSSWDNQC  QCTSSATRNT  TKQVTPQPEE 110         120         130         140         150

QKERKTTEMQ  SPMQPVDQAS  LPGHCREPPP  WENEATERIY  HFVVGQMVY 160         170         180         190         200
aCD25ep-b                       aCD25ep-a
QCVQGYRALH  RGPAESVCKM  THGKTRWTQP  QLICTGEMET  SQFPGEEKPQ 210         220         230         240         250

ASPEGRPESE  TSCLVTTTDF  QIQTEMAATM  ETSIFTTEYQ  VAVAGCVFLL 260         270

ISVLLLSGLT  WQRRQRKSRR  TI
```

FIGURE 2

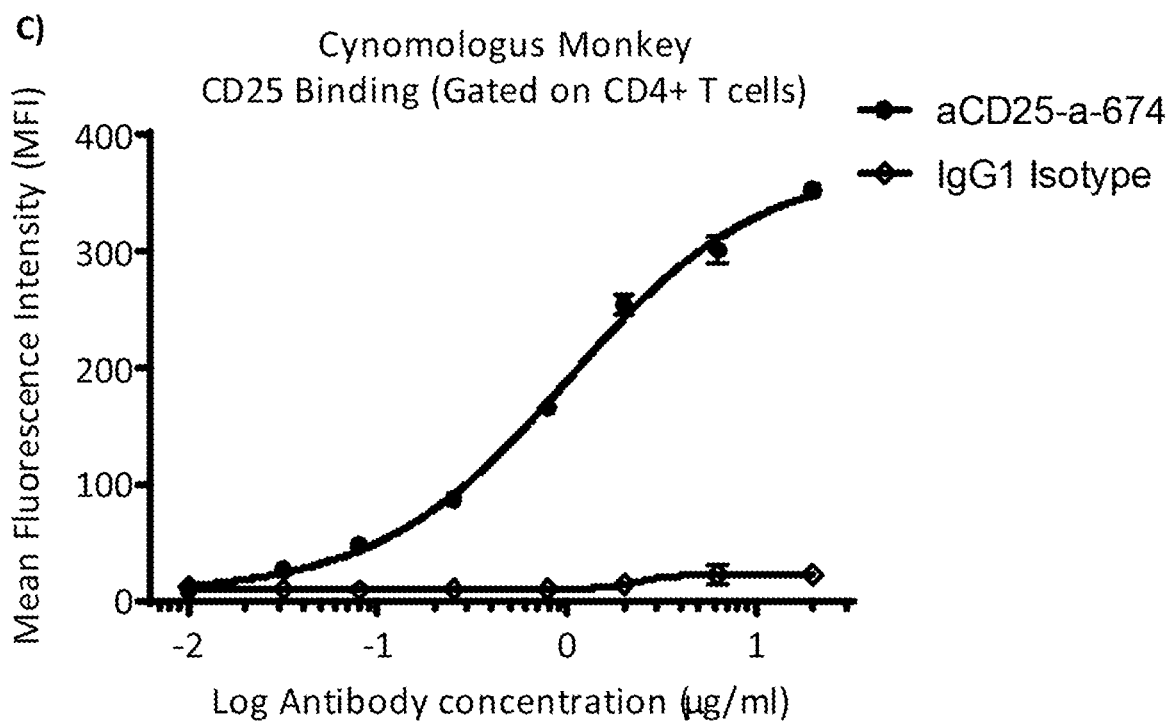
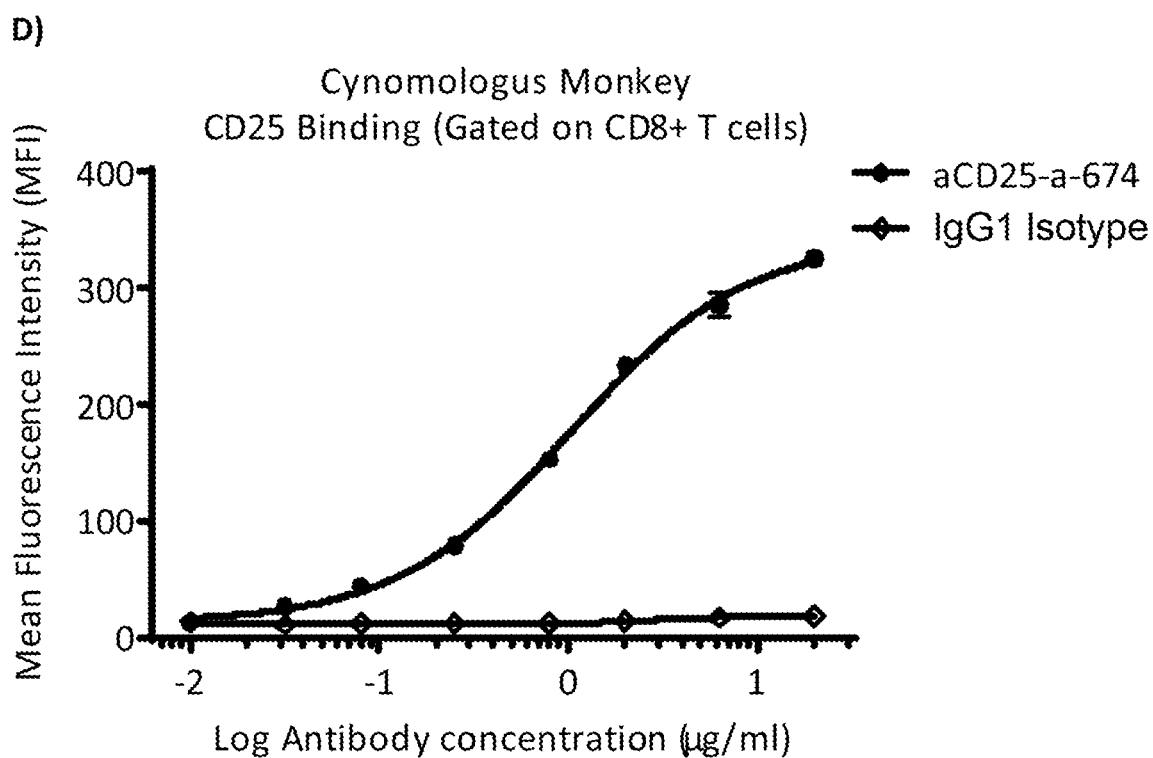
Figure 4. Cont.

A) Non IL-2 competing Ab (aCD25-a-674)
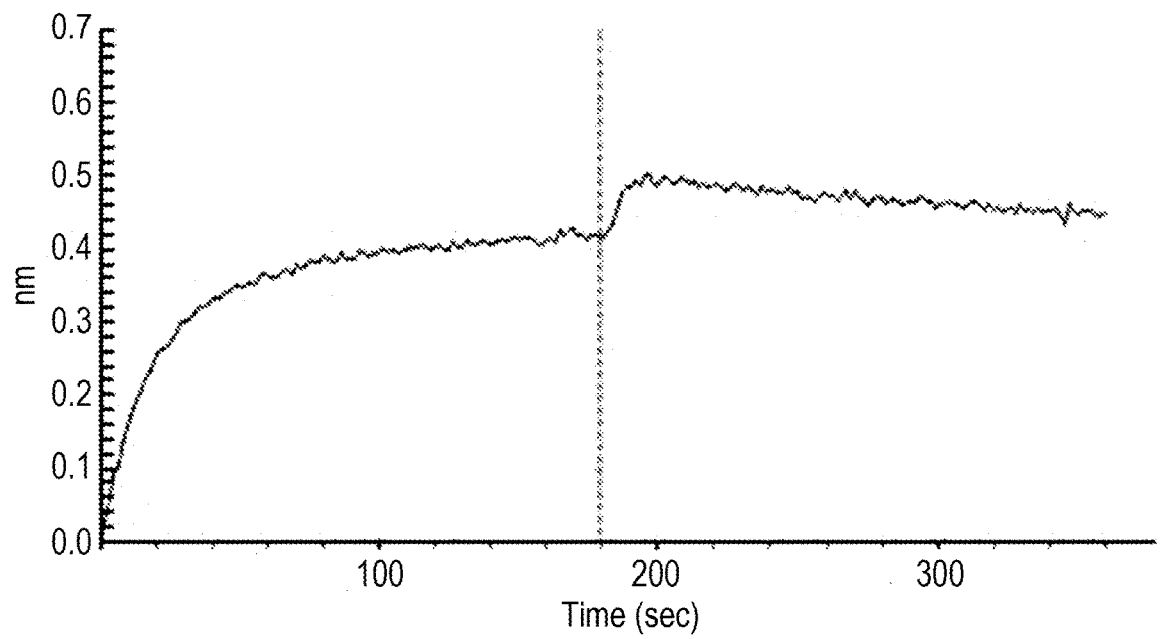
B) IL-2 Competing Ab
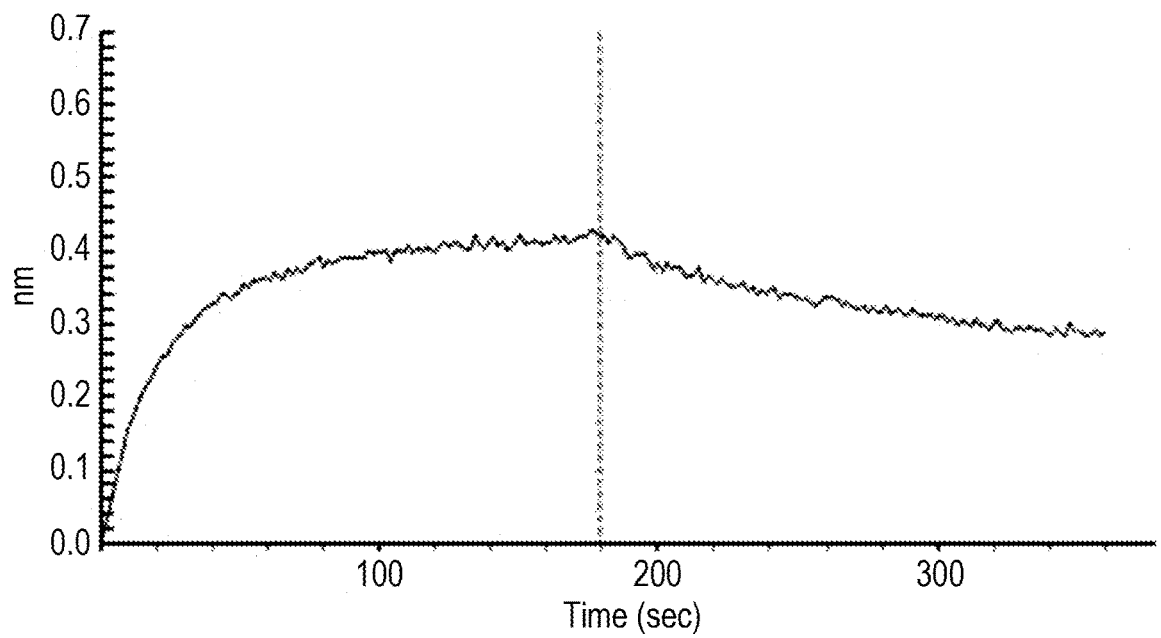
FIGURE 6

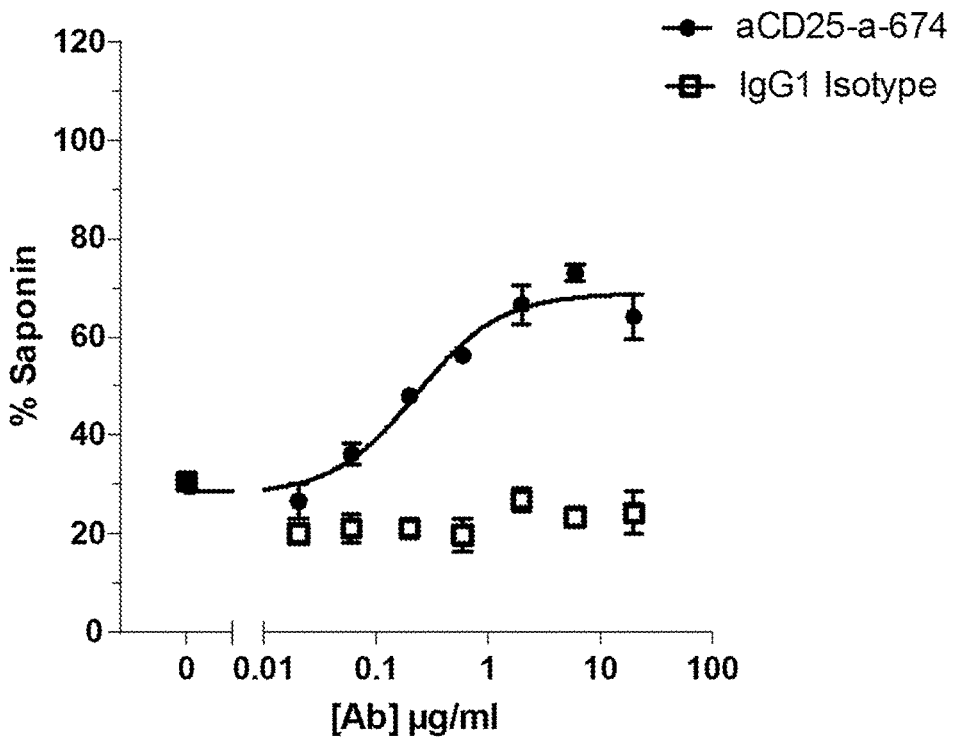
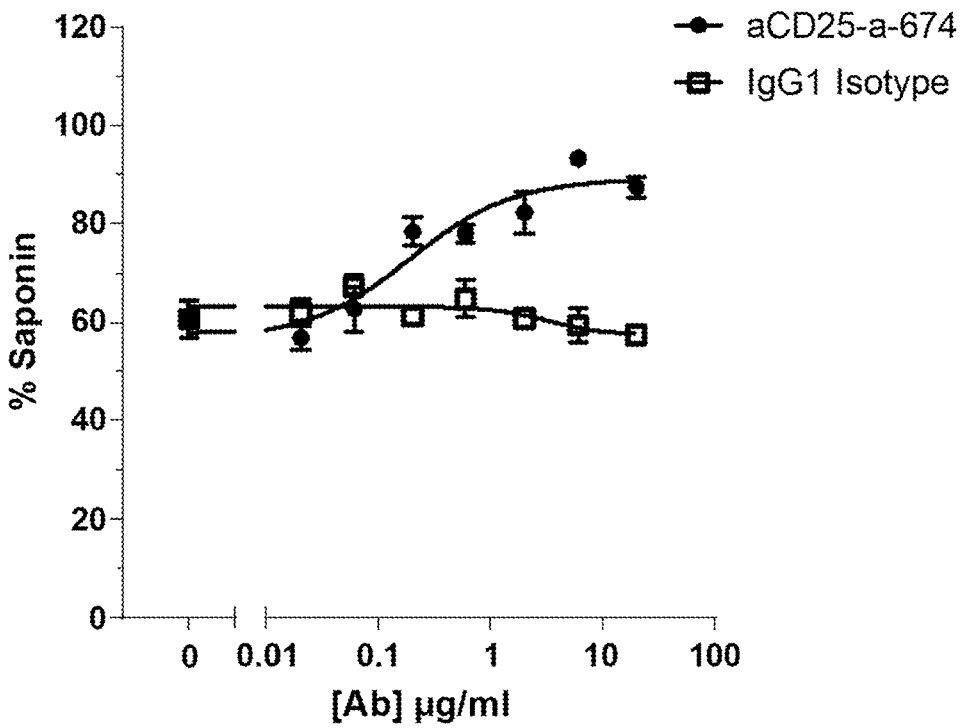
FIGURE 9

ANTI-CD25 ANTIBODY AGENTS

FIELD OF THE INVENTION

The present invention relates to anti-CD25 antibodies, pharmaceutical compositions comprising anti-CD25 antibodies and therapeutic uses of such antibodies.

The instant application contains a Sequence Listing which has been submitted electronically as .txt file named "Sequence Listing.txt" The .txt file was created on Mar. 6, 2019 and is 5,685bytes in size. The entire contents of the Sequence Listing are herein incorporated by reference.

BACKGROUND

Cancer immunotherapy involves the use of a subject's own immune system to treat or prevent cancer. Immunotherapies exploit the fact that cancer cells often have subtly different molecules on their surface that can be detected by the immune system. These molecules, or cancer antigens, are most commonly proteins, but also include molecules such as carbohydrates. Immunotherapy thus involves provocation of the immune system into attacking tumour cells via these target antigens. However, malignant tumours, in particular solid tumours, can escape immune surveillance by means of various mechanisms both intrinsic to the tumour cell and mediated by components of the tumour microenvironment. Amongst the latter, tumour infiltration by regulatory T cells (Treg cells or Tregs) and, more specifically, an unfavourable balance of effector T cells (Teff) versus Tregs (i.e. a low ratio of Teff to Treg), have been proposed as critical factors (Smyth M et al., 2014).

Since their discovery, Tregs have been found to be critical in mediating immune homeostasis and promoting the establishment and maintenance of peripheral tolerance. However, in the context of cancer their role is more complex. As cancer cells express both self- and tumour-associated antigens, the presence of Tregs, which seek to dampen effector cell responses, can contribute to tumour progression. The infiltration of Tregs in established tumours therefore represents one of the main obstacles to effective anti-tumour responses and to treatment of cancers in general. Suppression mechanisms employed by Tregs are thought to contribute significantly to the limitation or even failure of current therapies, in particular immunotherapies that rely on induction or potentiation of anti-tumour responses (Onishi H et al; 2012).

It has been consistently demonstrated that Treg cells contribute to the establishment and progression of tumors in murine models and that their absence results in delay of tumor progression (Elpek et al., 2007; Golgher et al., 2002; Jones et al., 2002; Onizuka et al., 1999; Shimizu et al., 1999). In humans, high tumor infiltration by Treg cells and, more importantly, a low ratio of effector T (Teff) cells to Treg cells, is associated with poor outcomes in multiple cancers (Shang et al., 2015). Conversely, a high Teff/Treg cell ratio is associated with favourable responses to immunotherapy in both humans and mice (Hodi et al., 2008; Quezada et al., 2006). Nevertheless, depletion of Tregs in tumours is complex, and results of preclinical and clinical studies in this area had been inconsistent, mostly due to the difficulty of identifying a target specific for Treg.

CD25 is one of the potential molecular targets for achieving depletion of Tregs. Indeed, CD25, also known as the interleukin-2 high-affinity receptor alpha chain (IL-2Rα), is constitutively expressed at high-levels on Treg cells, and it is absent or expressed at low-levels on T effector cells and is thus a promising target for Treg depletion. The IL-2/CD25 interaction has been the object of several studies in murine models, most of them involving the use of PC61, a rat anti-murine CD25 antibody (Setiady Y et al., 2010.). The CD25 binding and functional activities of this antibody have been compared to those of panel of monoclonal antibodies generated by different authors (Lowenthal J. W et al., 1985.; Moreau, J.-L et al.; Volk H D et al., 1989; Dental J et al., 1991,). While original studies demonstrated prophylactic but not therapeutic activity of PC61, a recent study showed that an Fc optimized version of this anti-CD25 antibody led to intra-tumoral Treg depletion and offers significant therapeutic benefit in several murine tumour models (Vargas A et al., 2017).

Available anti-CD25 antibodies such as PC61 block or inhibit the binding of IL-2 to CD25, as do many other anti-mouse CD25 antibodies and most of the antibodies disclosed as being anti-human CD25 antibodies; see for instance WO2004/045512, WO 2006/108670, WO1993/011238, WO1990/007861 and WO2017/174331. For example, basiliximab and daclizumab are anti-human CD25 antibodies that inhibit the binding of IL-2 to CD25 and have been developed to reduce activation of T-effector cells (Queen C et al, 1989 and Bielekova B, 2013). Basiliximab is a chimeric mouse-human CD25 antibody currently approved for graft versus host diseases and daclizumab is a humanized CD25 antibody approved for the treatment of multiple sclerosis.

A few other anti-CD25 antibodies still allow the binding of IL-2 to CD25, such as the clone 7D4 (anti-mouse CD25), clone 2E4 (anti-mouse CD25), clone MA251 (anti-human CD25) or 7G7B6 (anti-human CD25) (i.e. non-blocking antibodies). Inolimomab/BT536, whilst it is been purported not to block binding of IL-2 to CD25, does block the signalling of IL-2 via CD25. 7D4 is a rat IgM anti-mouse CD25 antibody that has been extensively used to detect CD25-positive cells in the presence of or following the treatment with PC61 or of antibodies having similar binding properties (Onizuka S et al., 1999). Very few documents disclose any functional property of 7D4-IgM antibody, alone or in comparison with PC61 (Kohm A et al., 2006; Hallett W et al., 2008; Fecci P et al., 2006; McNeill A et al., 2007; Setiady Y et al., 2010; Couper K et al., 2007). Indeed, the prior art does not teach the possibility to adapt or somehow modify the isotype or other structural features of 7D4 in order to obtain an improved antibody, in particular those that can be used in cancer therapy. The ability of 7D4-IgM (as such or as an engineered antibody) or of any anti-human CD25 designed or characterized as having CD25 binding features similar to those of 7D4 for mouse CD25 have not been evaluated in detail with respect to the optimized depletion of Treg cells.

As discussed above the infiltration of Treg cells in tumors, and in particular a low ratio of effector Teff cells to Treg cells, can lead to poor clinical outcome. CD25 has been identified as a Treg marker and could thus be an interesting target for therapeutic antibodies aiming at depleting Treg. Importantly, CD25 is the alpha subunit of the receptor for IL-2 and IL-2 is a key cytokine for Teff responses. Anti-CD25 antibodies that have undergone clinical testing so far whilst depleting Treg cells also block IL-2 signalling via CD25 (specifically a CD25/CD122/CD132 complex). The present inventors have now found that such a blockade of IL-2 signalling limits Teff responses and that an anti-CD25 antibody that does not block the IL2 signalling can effectively deplete Treg cells, whilst still allowing IL-2 to stimulate Teff cells, providing antibodies that exhibit a strong anti-cancer effect.

Thus, there is a need in the art for improved anti-CD25 antibodies, in particular those that do not block the binding of CD25 to IL-2 or IL-2 signalling, and that deplete Tregs, in particular in tumours, and that can be used in methods for treating cancer.

SUMMARY

The present invention provides new anti-CD25 Antibody Agents. In some embodiments, the provided anti-CD25 Antibody Agents are antibodies or antigen-binding fragments that specifically bind to CD25, particularly to human CD25, without blocking the binding of interleukin 2 (IL-2) to CD25, or signaling of IL-2 via CD25, and which efficiently deplete Tregs, in particular within tumors. The anti-CD25 Antibody Agents allow at least 50% of IL-2 signaling in response to IL-2 binding to CD25 compared to the level of signaling in the absence of the anti-CD25 Antibody Agent. The anti-CD25 Antibody Agents are therefore referred to as non-blocking or non-IL-2 blocking anti-CD25 Antibody Agents.

In some embodiments, the anti-CD25 Antibody agents or antigen-binding fragments bind CD25 without blocking the binding of IL-2 to CD25 or signalling of IL-2 via CD25. That is, in some embodiments, the anti-CD25 antibodies inhibit less than 50% of IL-2 signalling compared to IL-2 signalling in the absence of the antibodies. The anti-CD25 antibodies are characterized by structural elements that allow both binding CD25 without blocking the binding of IL-2 to CD25, or its signalling.

It has surprisingly been found that anti-CD25 antibodies that do not block IL-2 binding or signalling via CD25 and deplete Tregs have strong anti-tumour effects, in particular have a stronger anti-tumour effect than anti-CD25 antibodies that deplete Treg but block IL-2 signalling. The antibodies increased the CD4+Teff/Treg and CD8+Teff/Treg ratios. The effective depletion of tumor-infiltrating Treg cells whilst preserving IL-2 signalling on Teff cells leads to a therapeutic approach for use in treating cancer alone or in combination with other anti-cancer agents.

Those skilled in the art, however, will appreciate that teachings of the present disclosure are not limited by a particular mechanism of action of the provided antibodies or antigen-binding fragments thereof. Relevant structural and/or functional features of the provided antibodies are described herein and speak for themselves.

In some embodiments, the provided anti-CD25 Antibody Agents are characterized by one or more features that are associated with binding to a specific epitope in human CD25 extracellular domain, and/or that render them particularly amenable to pharmaceutical use and/or manufacturing.

The provided technologies, including the provided anti-CD25 Antibody Agents (e.g., the provided antibodies or antigen-binding fragments thereof), compositions including them, and/or uses for them, are useful in medicine. In some embodiments, such provided technologies are useful in cancer therapy and/or prophylaxis.

In some embodiments, the provided anti-CD25 Antibody Agents are exemplified by the antibodies having the sequence of aCD25-a-674, and more in general antibodies or agents that are or comprise one or more antigen-binding fragments or portions thereof, for example that comprise the aCD25-a-674-HCDR3 amino acid sequence as variable heavy chain complementarity determining region 3, and/or, in some embodiments, comprise one or both of the aCD25-a-674 HCDR1 and HCDR2 sequences. References to anti-CD25 Antibody Agents herein, such aCD25-a-674, includes variants thereof, including affinity matured variants thereof, unless the context implies otherwise.

In one embodiment, there is provided an anti-CD25 Antibody Agent that comprises the HCDR1, HCDR2 and HCDR3 amino acid sequences of aCD25-a-674. In another embodiment there is provided an anti-CD25 Antibody Agent that comprises the HCDR1, HCDR2, HCDR3, LCDR1, LCDR2 and LCDR3 amino acid sequences of aCD25-a-674. In another embodiment there is provided an anti-CD25 Antibody Agent that comprises the variable heavy amino acid sequence of aCD25-a-674. In another embodiment there is provided an anti-CD25 Antibody Agent that comprises the variable heavy and variable light amino acid sequences of aCD25-a-674, or of a variant thereof, including affinity matured variants.

In some embodiments, there is provided an anti-CD25 Antibody Agent that competes with aCD25-a-674 (or an antigen-binding fragment or derivative or variant thereof, including affinity matured variants) for binding to human CD25 extracellular domain.

In some embodiments, the provided anti-CD25 Antibody Agents (e.g. the provided antibodies including variants and derivatives thereof, such as affinity matured variants) antibodies or antigen-binding fragments thereof bind to human CD25 with a Kd in the range of $10^{-7}$ M or below (e.g., in the $10^{-8}$ or $10^{-9}$ or $10^{-10}$ or $10^{-11}$ or $10^{-12}$ or $10^{-13}$ range). In some embodiments the provided anti-CD25 Antibody Agents (e.g. the provided antibodies or antigen-binding fragments thereof, including variants and derivatives thereof, such as affinity matured variants) bind to human CD25 with a Kd value from $10^{-7}$ to $10^{-10}$, or from $10^{-7}$ to $10^{-9}$.

In some embodiments, the provided anti-CD25 Antibody Agents (e.g. the provided antibodies or antigen-binding fragments thereof, including variants and derivatives thereof) bind to an epitope on human CD25 that is bound by aCD25-a-674 (or an antigen-binding fragment or derivative or variant thereof). In some embodiments, such provided anti-CD25 Antibody Agents may bind to human CD25 extracellular domain. In some embodiments, the provided anti-CD25 Antibody Agents may bind to an epitope of CD25 (e.g., when assessed using one or more assays as described herein or otherwise known in the art), in particular the one identified as aCD25ep-a and aCD25ep-b. In some embodiments, the provided antibodies or antigen-binding fragments thereof may bind to human and non-human primate (for example Cynomolgus Monkey) CD25 (e.g., to an extracellular epitope on human and/or Cynomolgus Monkey CD25) with a Kd value in the $10^{-7}$ M range or below, for example in the $10^{-8}$ or $10^{-9}$ or $10^{-10}$ or $10^{-11}$ or $10^{-12}$ or $10^{-13}$ range. In some embodiments the provided anti-CD25 Antibody Agents (e.g. the provided antibodies or antigen-binding fragments thereof, including variants and derivatives thereof, such as affinity matured variants) bind to human CD25 with a Kd value from $10^{-7}$ to $10^{-10}$, or from $10^{-7}$ to $10^{-9}$.

Among other things, the present disclosure provides a procedure that can be utilized to identify and/or characterize particularly useful anti-CD25 Antibody Agents (e.g., anti-CD25 antibodies or antigen-binding fragments thereof) as described herein (e.g., anti-CD25 antibodies or antigen-binding fragments thereof characterized by certain structural and/or functional features, such as specific binding to human CD25 (e.g., to an extracellular epitope thereof), inclusion of one or more CDR sequence elements as described herein (and particularly inclusion of an HCDR3 sequence element, optionally in combination with HCDR1 and/or HCDR2 elements), impact on IL-2 signalling activity as described herein, cytotoxic activity as described herein (e.g., with respect to CD25-positive cells such as immune regulatory cells or CD25 expressing cancer cells), and combinations thereof). In some embodiments, particularly useful anti-CD25 antibodies as described herein are characterized by a plurality of such features. In some embodiments, one or more antibodies described herein may be characterized as anti-CD25 Antibody Agents.

Thus, as exemplified herein, certain antibodies and/or antigen-binding fragments comprising aCD25-a674 sequences (in particular aCD25-a-674-HCDR3 and/or aCD25-a-674-LCDR3) are characterized by such desirable structural and/or functional features; such antibodies and/or antigen-binding fragments thereof may be referred to herein as anti-CD25 Antibody Agents. Additionally, in accordance with the present disclosure, antibodies and antigen-binding fragments thereof that compete with aCD25-a-674 may be particularly useful antibodies; such antibodies and/or antigen-binding fragments thereof may also be referred to herein as anti-CD25 Antibody Agents.

Antibodies (and/or antigen-binding fragments thereof) described herein may be particularly useful in medicine (e.g., in therapy and/or in prophylaxis, for example in the treatment of cancer), and/or for use with respect to methods that require or involve targeting an epitope such as the one identified as aCD25ep-a and aCD25ep-b within human CD25 extracellular domain. The provided antibodies or antigen-binding fragments thereof may be prepared as presenting the most appropriate isotype, in particular human isotype from the group consisting of IgG1, IgG2, IgG3, and IgG4 isotype antibodies, more particularly human IgG1 or human IgG2, preferably human IgG1.

In one aspect, the present invention provides aCD25-a-674-HCDR3 amino acid sequence and polypeptides that include it, such as, for example, antibodies or antigen-binding fragments comprising the aCD25-a-674-HCDR3 amino acid sequence (SEQ ID NO: 4) as variable heavy chain complementarity determining region 3. In some embodiments, such antibody or antigen-binding fragment may be further characterized by comprising further aCD25-a-amino acid sequence elements such as:
  a) aCD25-a-674-HCDR1 amino acid sequence (SEQ ID NO: 2) as variable heavy chain complementarity determining region 1; and/or
  b) aCD25-a-674-HCDR2 amino acid sequence (SEQ ID NO: 3) as variable heavy chain complementarity determining region 2.

In some embodiments, provided antibodies or antigen-binding fragments thereof may comprise variable heavy chain complementarity determining regions defined above (i.e. aCD25-a-674 amino acid sequence elements) further in the correct order, specifically separated by antibody frame sequences, such as the ones included in aCD25-a-674-HCDR123 amino acid sequence (SEQ ID NO: 5), in particular for exerting correctly their binding and functional properties. For example, in some embodiments, a provided antibody or antigen-binding fragment said thereof can comprise aCD25-a-674-HCDR123 amino acid sequences (SEQ ID NO: 5) and, optionally:
  a) aCD25-a-674-LCDR1 amino acid sequence (SEQ ID NO: 6) as variable light chain complementarity determining region 1;
  b) aCD25-a-674-LCDR2 amino acid sequence (SEQ ID NO: 7) as variable light chain complementarity determining region 2; and
  c) aCD25-a-674-LCDR3 amino acid sequence (SEQ ID NO: 8) as variable light chain complementarity determining region 3.

Thus, in some embodiments, the present invention provides an isolated antibody or antigen-binding fragments thereof comprising a variable heavy chain comprising aCD25-a-674-HCDR123 amino acid sequence (SEQ ID NO: 5). Preferably, such isolated antibody or antigen-binding fragments thereof further comprises a variable light chain comprising aCD25-a-674-LCDR123 amino acid sequence (SEQ ID NO: 9), as described in the Examples. Moreover, aCD25-a-674 amino acid sequences also refer to antibody sequences that are defined by a number of substitutions with respect to the aCD25-a-674 amino acid sequence elements defined above. For example, such sequence may comprise, as variable heavy chain complementarity determining region 3 (HCDR3) a sequence containing 1, 2, 3, 4, or more amino acid substitutions within aCD25-a-674-HCDR3 (SEQ ID NO: 4). In a further embodiment, aCD25-a-674 amino acid sequences also refer to antibody sequences comprising, as variable heavy chain complementarity determining regions 1, 2 and 3 (HCDR1, HCDR2, and HCDR3) a sequence containing 1, 2, 3, 4, 5, 6, 7, 8, 9, 10 or more amino acid substitutions within aCD25-a-674-HCDR1 (SEQ ID NO: 2), aCD25-a-674-HCDR2 (SEQ ID NO: 3), and aCD25-a-674-HCDR3 (SEQ ID NO: 4), and more preferably a sequence containing 1, 2, 3, 4, 5, 6, 7, 8, 9, 10 or more amino acid substitutions within aCD25-a-674-HCDR123 (SEQ ID NO: 5). The antibodies presenting such aCD25-a-674 amino acid sequence elements and such substitutions can still present the binding and/or functional properties of aCD25-a-674, and of anti-CD25 Antibody Agents in general.

Accordingly, in one embodiment, the present invention provides an anti-CD25 Antibody Agent (i.e. an antibody or antigen-binding fragment thereof) comprising:
  a. the variable heavy chain region sequence of aCD25-a-674 (SEQ ID NO: 5) (or a variant thereof, such as an affinity matured variant thereof) or a variable heavy chain region sequence having up to 5 amino acid substitutions compared to the variable heavy chain region sequence of aCD25-a-674 (or a variant thereof, such as an affinity matured variant thereof); and/or
  b. the variable light chain region sequence of aCD25-a-674 (SEQ ID NO: 9) (or a variant thereof, such as an affinity matured variant thereof) or a variable light chain region sequence having up to 5 amino acid substitutions compared to the variable light chain region sequence of aCD25-a-674 (or a variant thereof, such as an affinity matured variant thereof).

In some embodiments, the amino acid substitutions do not occur in an CDR sequence.

In some embodiments, the present invention provides an anti-CD25 Antibody Agent (i.e. an antibody or antigen-binding fragment thereof) comprising:
  a. the variable heavy chain region sequence of aCD25-a-674 (SEQ ID NO: 5) (or a variant thereof, such as an affinity matured variant thereof) or a variable heavy chain region sequence having at least 80%, at least 85%, at least 90%, at least 95%, at least 96%, at least 97%, at least 98% or at least 99% sequence identity to the variable heavy chain region sequence of aCD25-a-674 (or a variant thereof, such as an affinity matured variant thereof); and/or b. the variable light chain region sequence of aCD25-a-674 (SEQ ID NO: 9) (or a variant thereof, such as an affinity matured variant thereof) or a variable light chain region sequence having at least 80%, at least 85%, at least 90%, at least 95%, at least 96%, at least 97%, at least 98% or at least 99% sequence identity to the variable light chain region sequence of aCD25-a-674 (or a variant thereof, such as an affinity matured variant thereof).

In some embodiments, the % sequence identity is calculated without the sequences of all 6 CDRs of aCD25-a-686 (or a variant thereof, such as an affinity matured variant thereof, as disclosed herein). For example, the anti-CD25 Antibody Agent may comprise a variable heavy chain region sequence having at least 95% identity to the variable heavy chain region sequence of aCD25-a-686 (or a variant thereof, such as an affinity matured variant thereof) and/or a variable light chain region sequence having at least 95% identity to the variable light chain region sequence of aCD25-a-686 (or a variant thereof, such as an affinity matured variant thereof), wherein any amino acid variations occur only in the framework regions of the variable heavy and light chain region sequences. In such embodiments, the anti-CD25 Antibody Agents having certain sequence identities comprise the complete heavy and light chain CDR1, CDR2 and CDR3 sequences of the anti-CD25 Antibody Agent from which they are derived.

The invention also provides variant antibodies or antigen-binding fragments thereof of the antibodies described herein. The invention provides antibodies or antigen-binding fragments thereof wherein any DG motif in the light or heavy chains of the antibodies may be altered, for example to reduce aspartate isomerization and/or wherein any NG motif in the light or heavy chains of the antibodies may be altered, for example to reduce asparagine deamidation and/or wherein any methionine in the light or heavy chains of the antibodies may be altered, for example to reduce methionine oxidation. For example, a DG motif may be altered to substitute one or both of the amino acids in the motif with a different amino acid. An NG motif may be altered to substitute one or both of the amino acids in the motif with a different amino acid. For example, such motifs may be mutated to EG, DQ or DA. A methionine residue may be altered to replaced it with a different amino acid, for example leucine or phenylalanine.

In such embodiments, the anti-CD25 antibody or antigen-binding fragment thereof may be, or may be derived from, for example, aCD25-a-674. The variant anti-CD25 antibodies provide further antibodies having any, and possibly all, binding and functional properties of aCD25-a-674. For example, the variant anti-CD25 antibodies are non-IL-2 blocking antibodies.

Accordingly, in some embodiments, the antibodies or fragments thereof provided herein can be mutated to remove or modify DG motifs or NG motifs, in particular DG or NG motifs appearing in the CDR regions, as is standard in the art to reduce susceptibility to chemical modification. Such antibodies that have been modified in this may way need to undergo further modification (for example affinity maturation) before arriving at a final sequence.

In one embodiment of the invention, there is provided a variant antibody having CDR1, CDR2 and CDR3 sequences of an antibody as disclosed herein (for example the CDR1, CDR2 and CDR3 sequences of aCD25-a-674), or the variable heavy and variable light chain of any antibody as disclosed herein (for example the variable heavy and variable light chain of any of aCD25-a-674), but differing from the specified sequence in that at least one or at least two DG or NG motifs in the CDRs (if present) have been changed to a different motif. The disclosed variants may be used and formulated as described for aCD25-a-674.

The invention also provides affinity matured antibodies, for example affinity matured variants derived from any of the antibodies disclosed herein. In one embodiment, the affinity matured antibodies are affinity matured antibodies having an altered DG motif and/or NG motif and/or altered to remove or mutate any methionine residues. The disclosed affinity matured variants may be used and formulated as described for aCD25-a-674.

In some embodiments the invention provides a method of preparing an anti-CD25 antibody comprising providing an antibody as herein described (e.g., aCD25-a-674 or an antigen binding fragment or variant thereof), and subjecting the antibody to affinity maturation, wherein the antibody produced binds to CD25 with greater affinity than the parental antibody. Preferably the produced antibody binds to CD25 with at least 20%, at least 30%, at least 40%, more preferably at least 50% greater affinity than the parental antibody binds to CD25, for example as measured by the Kd. Methods for measuring affinity are known in the art and described in the Examples below. The affinity matured antibodies produced by such methods can be formulated and used as described herein for the other anti-CD25 Antibody Agents.

Affinity maturation may be carried out according to any suitable method known to the skilled person. For example, in vitro antibody display systems are widely used for the generation of specific antibodies with high affinity. In these systems, the phenotype (i.e., the antibody fragment) is coupled to the genotype (i.e., the antibody gene) allowing the direct determination of the sequence of the antibody. Several systems have been developed to achieve display of antibody repertoires to allow subsequent selection of binders and by increasing the stringency of selection allows for the selection of higher and higher affinity variants. The antibody fragments can be expressed in yeast, ribosomes, phage display particles or by direct coupling to DNA.

Current antibody affinity maturation methods belong to two mutagenesis categories: stochastic and non-stochastic. Error-prone polymerase chain reaction (PCR), mutator bacterial strains, and saturation mutagenesis are typical examples of stochastic mutagenesis methods. Non-stochastic techniques often use alanine-scanning or site-directed mutagenesis to generate limited collections of specific variants. In addition, shuffling approaches to obtain shuffled variants of the parent antibody can also be used to improve antibodies affinity further.

Accordingly, in one embodiment of the invention, the method of affinity maturation is selected from the group consisting of stochastic mutagenesis (for example error-prone polymerase chain reaction (PCR), mutator bacterial strains, or saturation mutagenesis), non-stochastic mutagenesis (for example alanine-scanning or site-directed mutagenesis), shuffling (for example DNA shuffling, chain shuffling or CDR shuffling) and the use of the CRISPR-Cas9 system to introduce modifications.

Affinity maturation methods are described in, for example, Rajpal et al., Proc Natl Acad Sci USA, 2005, 102(24):8466-71, Steinwand et al., MAbs, 2014, 6(1):204-18, as well as in Handbook of Therapeutic Antibodies, Wiley, 2014, Chapter 6, Antibody Affinity (pages 115-140).

In some embodiments there is provided a method of preparing a pharmaceutical composition comprising providing an antibody prepared according to a method above, (i.e.

for producing an antibody by affinity maturation) and co-formulating the antibody with at least one or more pharmaceutically acceptable excipients. The antibody used in the preparation of the pharmaceutical composition can be an affinity matured variant of aCD25-a-674. The pharmaceutical compositions produced by such methods can be used in the methods of treatment of the present invention as described herein for the other anti-CD25 Antibody Agents.

Antibodies and/or antigen-binding fragments that specifically bind CD25 as described herein (e.g., an anti-CD25 Antibody Agents that may include one or more aCD25-a-674 amino acid sequence elements such aCD25-a-674-HCDR3 (SEQ ID NO: 4) or aCD25-a-674-HCDR123 (SEQ ID NO: 5), and/or that may compete with aCD25-a-674 for binding to human CD25 and non-human primate CD25, for example Cynomolgus monkey CD25, etc.) may be provided in any of a variety of formats. For example, in some embodiments an appropriate format may be or comprise a monoclonal antibody, a domain antibody, a single chain antibody, a Fab fragment, a F(ab')2 fragment, a single chain variable fragment (scFv), a scFv-Fc fragment, a single chain antibody (scAb), an aptamer, or a nanobody. In some embodiments, an antibody or antigen-binding fragment thereof (and particularly a monoclonal antibody), may be a rabbit, mouse, chimeric, humanized or fully human antibody or antigen-binding fragment thereof. In some embodiments, a provided antibody or antigen-binding fragment thereof may be of an IgG, IgA, IgE, or IgM isotype (preferably human ones), as it can be most appropriate for a given use. In some embodiments, a provided antibody or antigen-binding fragment thereof is an IgG isotype, more particularly an IgG1, IgG2, IgG3, or IgG4 isotype. (In some embodiments the antibody or antigen-binding fragment thereof is from the human IgG1 subclass. In another embodiment the antibody or antigen-binding fragment thereof is from the human IgG2 subclass). In some embodiments, a provided antibody or antigen-binding fragment thereof (e.g., is provided as part of a multi-specific binding agent such as, for example, when it is desirable to associate further binding and/or functional moieties to anti-CD25 Antibody Agents such as a aCD25-a-674 amino acid sequence, the isolated antibody or antigen-binding can be comprised in a bispecific antibody, a multispecific antibody, or other multi-specific format that may be available in the art.

In some embodiments, a provided anti-CD25 Antibody Agent comprises a CD25-binding entity (e.g., an anti-CD25 antibody or antigen-binding fragment thereof) and a conjugated payload such as a therapeutic or diagnostic agent. In many such embodiments, the agent is considered and/or referred to as an "immunoconjugate". Examples of technologies and compounds that can be used for generating specific immunoconjugates such as antibody-drug are disclosed in the literature (Beck A et al., 2017) and described as applicable to several known anti-CD25 antibodies (O'Mahony D et al, 2008; Oh et al, 2017; Kreitman R J et al, 2016; Flynn M J et al 2016).

In some embodiments, the present invention provides aCD25-a-674 amino acid sequences that identify provided antibodies or antigen-binding fragments thereof (or a variant thereof, including affinity matured variants). In some embodiments, such sequences identify provided antibodies or antigen-binding fragments thereof that bind an epitope in human CD25 (such as aCD25ep-a and aCD25ep-b), and optionally also a corresponding epitope of a non-human primate CD25, e.g. Cynomolgus monkey and/or of a murine CD25, either as isolated proteins or on the surface of cells expressing CD25 (such as immune cells or cell lines, e.g. SU-DHL1 cells).

In some embodiments, the present invention provides anti-CD25 antibodies or antigen-binding fragments that specifically bind to an epitope of human CD25, wherein the epitope comprises one or more amino acid residues comprised in the amino acids 150-158 and/or 176-186 of SEQ ID NO:1. Preferably the epitope comprises at least 4 amino acids wherein the epitope comprises one or more amino acids comprised in amino acids 150-158 and/or 176-186 of SEQ ID NO:1. Preferably the epitope comprises at least 5 amino acids, at least 6 amino acids, at least seven amino acids, at least eight amino acids, at least nine amino acids, at least ten amino acids, at least eleven amino acids, at least twelve amino acids, at least thirteen amino acids, or at least fourteen or more amino acids wherein the epitope comprises one or more amino acids comprised in amino acids 150-158 and/or 176-186 of SEQ ID NO:1. The epitope may be either linear or conformational, i.e. discontinuous. In some embodiments, the anti-CD25 antibodies or antigen-binding fragments specifically bind to an epitope of human CD25 wherein the epitope comprises at least two, at least three, at least four, at least five, at least six, at least seven, at least eight, at least nine, at least ten, at least eleven, at least twelve, at least thirteen, or at least fourteen or more amino acid residues comprised in amino acids 150-158 and/or 176-186 of SEQ ID NO:1. In some embodiments, the anti-CD25 antibodies or antigen-binding fragments bind to an epitope comprising amino acids 150-158 and 176-186 of SEQ ID NO:1.

In some embodiments, the present invention provides procedures for screening and/or characterizing antibodies or antigen-binding fragments that comprise a aCD25-a-674 amino acid sequence and/or that present binding features comparable to antibodies or antigen-binding fragments thereof comprising one or more aCD25-a-674 amino acid sequence elements (e.g. including aCD25-a-674-HCDR3 amino acid sequence (SEQ ID NO: 4) and/or competing with aCD25-a-674) that allow binding to human CD25 extracellular domain as isolated protein and on the surface of cells expressing human CD25, competing for the same epitope in particular the one identified in the Examples as aCD25ep-a (protein sequence RWTQPQLICTG (SEQ ID NO: 10); amino acids 176-186 in Uniprot sequence P01589) and aCD25ep-b (protein sequence YQCVQGYRA (SEQ ID NO: 11); amino acids 150-158 in Uniprot sequence P01589).

Furthermore, the present invention also provides procedures for screening antibodies or antigen-binding fragments thereof that present functional features comparable to antibodies or antigen-binding fragments thereof comprising one or more aCD25-a-674 amino acid sequence elements, such features including lack of inhibition of the interaction between IL-2 and CD25, lack of inhibition of IL-2 signalling, and cytotoxic activities, and acting as anti-CD25 Antibody Agents. At these scopes, the candidate antibodies can be tested in the assays that are described in the Examples or other assays that are known in the art for establishing the presence of any of such features, but possibly all of them when evaluated in in vitro/ex vivo assays, cell-based assays, and/or animal models.

In some embodiments, the present invention provides nucleic acid molecules encoding an isolated antibody or antigen-binding fragment thereof that comprises an anti-CD25 Antibody Agent such as an aCD25-a-674 amino acid sequence (or a variant thereof, including affinity matured variants). In some embodiments, such provided nucleic acid molecules may contain codon-optimized nucleic acid sequences, and/or may be included in expression cassettes within appropriate nucleic acid vectors for the expression in host cells such as, for example, bacterial, yeast, insect, piscine, murine, simian, or human cells.

In some embodiments, the present invention provides host cells comprising heterologous nucleic acid molecules (e.g. DNA vectors) that express a provided anti-CD25 Antibody Agent (e.g., an antibody or antigen-binding fragment thereof) having one or more properties, e.g., as described herein, of an anti-CD25 Antibody Agent (e.g., comprising a aCD25-a-674 amino acid sequence). In some embodiments, the present disclosure provides methods of preparing an anti-CD25 Antibody Agent (e.g., an antibody or antigen-binding fragment thereof) having one or more properties, e.g., as described herein, of an anti-CD25 Antibody Agent (e.g. comprising a aCD25-a-674 amino acid sequence). In some embodiments, such methods may comprise culturing a host cell that comprises nucleic acids (e.g., heterologous nucleic acids that may comprise and/or be delivered to the host cell via vectors). In some embodiments, such a host cell (and/or the heterologous nucleic acid sequences) is/are arranged and constructed so that the anti-CD25 Antibody Agent (e.g. the antibody or antigen-binding fragment thereof) is secreted from the host cell (e.g., so that it can be isolated from cell culture supernatants), and/or exposed on the cell surface (for instance, if such aCD25-a-674 amino acid sequences and sequence elements are intended to be used in the context of, or together with, such cells, as in artificial T cell receptors grafting the specificity of a monoclonal antibody onto T cells).

In some embodiments the antibody or antigen-binding fragment may be afucosylated. It is well known that antibody glycosylation may have impact on the activity, pharmacokinetics and pharmacodynamics of antibodies (e.g., monoclonal antibodies, recombinant antibodies, and/or antibodies that are otherwise engineered or isolated) and Fc-fusion proteins and specific technology may be exploited to obtain an antibody with the desired glycosylation profile (Liu L, 2015). Effector functions supporting the cytotoxicity of an antibody for use in accordance with the present invention (e.g., an anti-CD25 antibody as described herein, including for example an antibody which may be or be described as an anti-CD25 Antibody Agent) can be enhanced using methods to decrease antibody fucosylation levels. Antibodies comprising specific aCD25-a-674 sequence elements presenting such properties can be generated, for example, by expressing a aCD25-a-674 sequence using technologies for genetically engineering cell lines with absent or reduced fucosylation capacity, some of them commercially available such as Potelligent (Lonza), GlyMAXX (ProBiogen), those provided by Evitria, or by manipulating the manufacturing process, for example by controlling osmolarity and/or using enzyme inhibitors, see also for example the methods described in EP2480671.

In some embodiments, the present invention provides compositions (e.g. pharmaceutical compositions) comprising a provided antibody or an antigen-binding fragment thereof having desirable properties as described herein (e.g., as described for antibodies that are herein termed anti-CD25 Antibody Agents, specifically including, for example, aCD25-a-674 antibodies or antigen-binding fragments thereof or antibodies or antigen-binding fragments thereof that compete with aCD25-a-674 antibodies for binding with CD25). In some embodiments, such provided compositions are intended for and/or are used in a medical use, such as a therapeutic, diagnostic, or prophylactic use. In some embodiments, such a provided composition can further comprise a pharmaceutically acceptable carrier or excipient and/or may be for use in the treatment of cancer. In some embodiments, a pharmaceutical composition may be formulated with one or more carrier, excipients, salts, buffering agents, etc., as is known in the art. Those of skill in the art will be aware of and readily able to utilize a variety of formulation technologies, including as may be particularly desirable and/or useful for a given method and/or site of administration, for instance for parenteral (e.g. subcutaneous, intramuscular, or intravenous injection), mucosal, intratumoral, peritumoral, oral, or topical administration. In many embodiments, provided pharmaceutical compositions, comprising anti-CD25 Antibody Agent as described herein (e.g., an anti-CD25 antibody or antigen binding portion thereof, are formulated for parenteral delivery (e.g., by injection and/or infusion). In some embodiments, such a provided pharmaceutical composition may be provided, for example, in a pre-loaded syringe or vial format. In some embodiments, such a provided pharmaceutical composition may be provided and/or utilized, for example, in dry (e.g., lyophilized) form; alternatively, in some embodiments, such a provided pharmaceutical composition may be provided and/or utilized in a liquid form (e.g., as a solution, suspension, dispersion, emulsion, etc), in a gel form, etc.

In some embodiments, the present invention provides uses of anti-CD25 Antibody Agents (e.g., anti-CD25 antibodies or antigen-binding fragments thereof) as described herein (e.g. comprising a aCD25-a-674 amino acid sequence element), and/or of a composition comprising them, in treatment of and/or in the manufacture of a medicament for treatment of, a cancer, such as a B cell malignancy, a lymphoma, (Hodgkins Lymphoma, non-Hodgkins lymphoma, chronic lymphocytic, leukemia, acute lymphoblastic leukemia, myelomas), a myeloproliferative disorder, a solid tumor (such as a breast carcinoma, a squamous cell carcinoma, a colon cancer, a head and neck cancer, a lung cancer, a genitourinary cancer, a rectal cancer, a gastric cancer, sarcoma, melanoma, an esophageal cancer, liver cancer, testicular cancer, cervical cancer, mastocytoma, hemangioma, eye cancer, laryngeal cancer, mouth cancer, mesothelioma, skin cancer, rectal cancer, throat cancer, bladder cancer, breast cancer, uterine cancer, prostate cancer, lung cancer, pancreatic cancer, renal cancer, stomach cancer, gastric cancer, non-small cell lung cancer, kidney cancer, brain cancer, and ovarian cancer). The cancer can be also defined on the basis of presence of specific tumor-relevant markers and antigens such as CD20, HER2, PD-1, PD-L1, SLAM7F, CD47, CD137, CD134, TIM3, CD25, GITR, CD25, EGFR, etc or a cancer that has been identified as having a biomarker referred to as microsatellite instability-high (MSI-H) or mismatch repair deficient (dMMR). Furthermore, such conditions may also be considered when defining pre-cancerous, non-invasive states of the above cancers, such as cancer in-situ, smouldering myeloma, monoclonal gammopathy of undetermined significance, cervical intra-epithelial neoplasia, MALTomas/GALTomes and various lymphoproliferative disorders. Preferably in some embodiments the subject being treated has a solid tumor.

Thus, in some embodiments, the present invention provides methods of treating cancer in a subject, comprising administering to the subject an effective amount of a composition comprising a provided anti-CD25 Antibody Agent (e.g., anti-CD25 antibodies or antigen-binding fragments thereof) as described herein (e.g. comprising aCD25-a-674 amino acid sequences) or an antibody or antigen-binding fragment thereof that competes with an antibody comprising aCD25-a-674 amino acid sequences for the binding of CD25. Preferably in some embodiments the subject has a solid tumor.

Thus, in some embodiments, the present invention provides a method of depleting regulatory T cells in a subject comprising the step of administering to the subject an effective amount of a composition comprising a provided anti-CD25 Antibody Agent (e.g., anti-CD25 antibodies or antigen-binding fragments thereof) as described herein (e.g. comprising aCD25-a-674 amino acid sequences) or an antibody or antigen-binding fragment that competes with an antibody comprising aCD25-a-674 amino acid sequences for the binding of CD25. In one embodiment the subject has a solid tumor. In one embodiment the subject has a haematological cancer.

In some embodiments, provided methods may further comprise administering, simultaneously or sequentially in any order, at least one additional agent or therapy to the subject (i.e., so that the subject receives a combination therapy). In some embodiments, such an at least one additional agent or therapy can be or comprise an anticancer drug (e.g., a chemotherapeutic agent), radiotherapy (by applying irradiation externally to the body or by administering radioconjugated compounds), an anti-tumor antigen or marker antibody (the antigen or marker being for example CD4, CD38, CA125, PSMA, c-MET, VEGF, CD137, VEGFR2, CD20, HER2, HER3, SLAMF7, CD326, CAIX, CD40, CD47, or EGF receptor), a checkpoint inhibitor or an immunomodulating antibody (for example an antibody targeting PD-1, PD-L1, TIM3, CD38, GITR, CD134, CD134L, CD137, CD137L, CD80, CD86, B7-H3, B7-H4, B7RP1, LAG3, ICOS, TIM3, GAL9, CD28, AP2M1, SHP-2, OX-40, VISTA, TIGIT, BTLA, HVEM, CD160, etc.), a vaccine (in particular, a cancer vaccine, for example GVAX), an adjuvant, standard-of-use protocol, one or more other compounds targeting cancer cells or stimulating an immune response against cancer cells, or any combination thereof. Preferably the additional agent is an immune checkpoint inhibitor such as a PD-1 antagonist, for example an anti-PD-1 antibody or an anti-PD-L1 antibody. In certain particular embodiments, when such at least one additional agent or therapy is or comprises an antibody, the format of and/or the antigen targeted by such antibody can be chosen among those listed in the literature and possibly adapted to a given cancer (Sliwkowski M & Mellman I, 2013; Redman J M et al., 2015; Kijanka M et al., 2015). Such antigens and corresponding antibodies include, without limitation CD22 (Blinatumomab), CD20 (Rituximab, Tositumomab), CD56 (Lorvotuzumab), CD66e/CEA (Labetuzumab), CD152/CTLA-4 (Ipilimumab), CD221/IGF1R (MK-0646), CD326/Epcam (Edrecolomab), CD340/HER2 (Trastuzumab, Pertuzumab), and EGFR (Cetuximab, Panitumumab). In embodiments when the at least one additional agent or therapy is a chemotherapeutic agent, the chemotherapeutic agent can be those known in the art for use in cancer therapy. Such chemotherapeutic agents includes, without limitation, alkylating agents, anthracyclines, epothilones, nitrosoureas, ethylenimines/methylmelamine, alkyl sulfonates, alkylating agents, antimetabolites, pyrimidine analogs, epipodophylotoxins, enzymes such as L-asparaginase; biological response modifiers such as IFNα, IFN-γ, IL-2, IL-12, G-CSF and GM-CSF; platinum coordination complexes such as cisplatin, oxaliplatin and carboplatin, anthracenediones, substituted urea such as hydroxyurea, methylhydrazine derivatives including N-methylhydrazine (MIH) and procarbazine, adrenocortical suppressants such as mitotane (o,p'-DDD) and aminoglutethimide; hormones and antagonists including adrenocorticosteroid antagonists such as prednisone and equivalents, dexamethasone and aminoglutethimide; progestin such as hydroxyprogesterone caproate, medroxyprogesterone acetate and megestrol acetate; estrogen such as diethylstilbestrol and ethinyl estradiol equivalents; antiestrogen such as tamoxifen; androgens including testosterone propionate and fluoxymesterone/equivalents; antiandrogens such as flutamide, gonadotropin-releasing hormone analogs and leuprolide; non-steroidal antiandrogens such as flutamide; molecules that target TGFβ pathways, IDO (indoleamine deoxigenase), Arginase, and/or CSF1R; PARP inhibitors such as olaparib, Veliparib, Iniparib, Rucaparib; and MET inhibitors such as tivantinib, foretinib, golvatinib, cabozantinib and crizotinib.

Still further, the present invention provides a variety of kits or articles of manufacture containing a provided anti-CD25 Antibody Agent (e.g., anti-CD25 antibody or antigen-binding fragment thereof) as described herein (e.g. comprising aCD25-a-674 amino acid sequences) or related compositions that allow the administration, storage, or other use of such an isolated antibody or antigen-binding fragment. In some embodiments, a provided kit comprises a vessel, syringe, a vial, or other container comprising such compositions, optionally together with one or more articles of manufactures, diluents, reagents, solid phases, and/or instructions for the correct use of the kit.

In some embodiments, identification, characterization, and/or validation of particular anti-CD25 Antibody Agent (e.g., anti-CD25 antibody or antigen-binding fragment thereof) as described herein (e.g. comprising aCD25-a-674 amino acid sequences) for a particular use, such as a medical use, and in particular for treating cancer, can be performed by using one or more assays or systems as described herein. In some embodiments, such identification, characterization, and/or validation may involve analysis of activity in one or more cell-based assays, for example using different experimental set-ups and/or a panel of selected (e.g., cancer-derived cell lines). In some embodiments, particularly given the proposed immunological mechanism associated certain desirable anti-CD25 Antibody Agents as described herein activities, desirable identification, characterization, and/or validation can involve collection of relevant data generated in animal models wherein cancers are induced or wherein cancer cells are implanted as a xenograft or as a syngeneic/allogeneic cancer-derived cells. Alternatively or additionally, in some embodiments, animal models may be utilized that involve transfer of human cells such as PBMC (i.e. humanized PBMC mouse models) or CD34+ hematopoietic stem cells alone (i.e. CD34+ humanized mice) or CD34+ hematopoietic stem cells together with liver and thymus (e.g. NSG-BLT mice) to allow evaluating activity of the anti-CD25 Antibody Agents on human immune cells within a model system.

In some embodiments, relevant sequences of anti-CD25 Antibody Agents (e.g., anti-CD25 antibody or antigen-binding fragments thereof) as described herein (e.g. comprising aCD25-a-674 amino acid sequences or otherwise including structural and/or functional characteristics of an agent described herein as anti-CD25 Antibody Agent) can be cloned into and/or expressed in context of an antibody frame that is more appropriate or desirable for pharmaceutical and/or technical reasons. For example, such sequences (possibly as codon-optimized VH and VL coding sequences) can be cloned together with human IgG1 constant regions (hIgG1) and expressed using an appropriate antibody expression vectors and cell line (such as a CHO-derived cell line, e.g. CHO—S). In some particular embodiments, expression and secretion of provided antibody sequences in human IgG1 format antibodies can be analyzed after transfection in reduced conditions in cell lysates and in non-reduced conditions in supernatants that will be later used to purify the antibody (by affinity chromatography, gel filtration, and/or other appropriate technique). Binding and/or other functional properties of provided anti-CD25 antibody sequences, in human IgG1 format (e.g., anti-CD25 Antibody Agents-hIgG1) can be analysed, for example by using one or more assays described in Examples below. For instance, such hIgG1-format provided antibodies can be evaluated for binding to human and cynomolgus PBMC or purified Treg or in vitro derived Treg or CD25 positive cell lines (such as SU-DHL-1 or Karpas299), e.g., using flow cytometry.

Moreover, the effect of one or more anti-CD25 Antibody Agents (e.g., anti-CD25 antibody or antigen-binding fragments thereof) as described herein (e.g. comprising aCD25-a-674 amino acid sequences or otherwise including structural and/or functional characteristics of an agent described herein as an anti-CD25 Antibody Agent—such as an anti-CD25 Antibody Agent-hIgG1) on human primary tumor cells and/or immune cells, including regulatory T cells, isolated from human healthy donors and/or patients can be assessed. In order to investigate potential effects of the anti-CD25 Antibody Agents, the antibodies can be used to treat PBMC and/or cells isolated from tumors (and/or organs such as lymph nodes) and/or tumor explants or other 3D organoids and/or purified or in vitro generated regulatory T cells or other CD25 positive cells such as some NK cells or Dendritic cells. Potential read outs comprise CD25 positive cells viability, elimination and/or apoptosis, tumor cell killing, effector immune cells proliferation and function (e.g. Granzyme B production, cytotoxic activity, degranulation), antigen-specific responses (as measured for example by proliferation, degranulation or cytokine production in response to an antigen). Alternatively or additionally, mice or non-human primates can be treated and cellular status can be followed in blood samples (analysed as whole blood or isolated PBMCs) or after isolation of various organs and/or cells from the animals, by e.g. flow cytometry or immunehistochemistry.

Alternatively or additionally, one or more properties of anti-CD25 Antibody Agents (e.g., anti-CD25 antibody or antigen-binding fragments thereof) as described herein (e.g. comprising aCD25-a-674 amino acid sequences or otherwise including structural and/or functional characteristics of an agent described herein as an anti-CD25 Antibody Agent—such as an anti-CD25 Antibody Agents-hIgG1) may be evaluated, alone or in combination, by studying the effects of such anti-CD25 Antibody Agents on CD25 expressing cells (e.g. Tregs or CD25-expressing cancer cells). Read out can include cell killing, cell apoptosis, intra-cellular signalling monitoring (e.g. Stat-5 phosphorylation), impact on IL-2 binding to CD25 and signalling (e.g. Stat-5 phosphorylation or other signalling downstream of the IL-2 receptor) and IL-2 dependent functional activities (e.g. proliferation and cytokine production). Cellular effects of antibodies can then be followed in vivo when aCD25 Antibody Agent-hIgG1 antibodies are administered to cynomolgus monkeys or to relevant mouse model.

In order to gain further insights into the molecular interactions between a provided anti-CD25 Antibody Agent and human CD25, the crystal structure of the anti-CD25 Antibody Agent (e.g., to give one specific example, an aCD25-a-674-hIgG1 antibody) and human CD25 protein can be determined. Solubility and/or stability of provided anti-CD25 Antibody Agents (specifically including, for example, aCD25-a-674-hIgG1 antibodies) can be assessed through solubility studies, accelerated stress studies, freeze thaw studies and formal stability studies. Aggregation of the antibodies can be followed by visual inspection, size exclusion chromatography and dynamic light scattering and $OD_{280/320}$ absorbance.

BRIEF DESCRIPTION OF DRAWINGS

FIG. 1: Relevant protein sequences of aCD25-a-674. Each CDR for the heavy (aCD25-a-674-HCDR1 (SEQ ID NO: 2), aCD25-a-674-HCDR2 (SEQ ID NO: 3), and aCD25-a-674-HCDR3 (SEQ ID NO: 4)) and the light (aCD25-a-674-LCDR1 (SEQ ID NO: 6), aCD25-a-674-LCDR2 (SEQ ID NO: 7), and aCD25-a-674-LCDR3 (SEQ ID NO: 8)) chain is indicated separately and, underlined, within the frame sequence of the heavy and light chain antibody as initially identified by the screening procedure (aCD25-a-674-HCDR123 (SEQ ID NO: 5) and aCD25-a-674-LCDR123 (SEQ ID NO: 9), respectively).

FIG. 2: Consensus sequence of human CD25 (Uniprot code P01589) (SEQ ID NO:1). The extracellular domain of mature CD25, corresponding to amino acids 22-240, is underlined. The position of aCD25-a-674 epitope as preliminarily identified (aCD25ep-a and aCD25ep-b) is indicated.

FIG. 6: Shows non-competitive binding of aCD25-a-674 and IL-2 (A) and competitive binding of a IL-2 competing antibody with IL-2 (B) by biolayer interferometry on the Octet Red384 using a standard sandwich format binning assay. The anti-human CD25 antibody, aCD25-a-674, was loaded onto AHQ sensors. The sensors were then exposed to 100 nM human CD25 followed by human IL-2. Additional binding by human IL2 after antigen association indicates an unoccupied epitope (non-competitor), while no binding indicates epitope blocking (competitor).

FIG. 9: Functional characterization of aCD25-a-674 compared to human IgG1 isotype control in respect to killing of CD25-positive cell lines in an ADCC assay. CD25-high or -low expressing cells, SU-DHL-1 (A) or SR-786 cells (B) respectively, were co-cultured with purified NK cells in the presence of varying concentrations of antibodies (as shown in the Figures). Target cell lysis was measured by calcein release into the supernatant at four hours post addition to NK cells. Data was normalised to saponin treated controls.

DETAILED DESCRIPTION OF CERTAIN EMBODIMENTS

Figure 3:
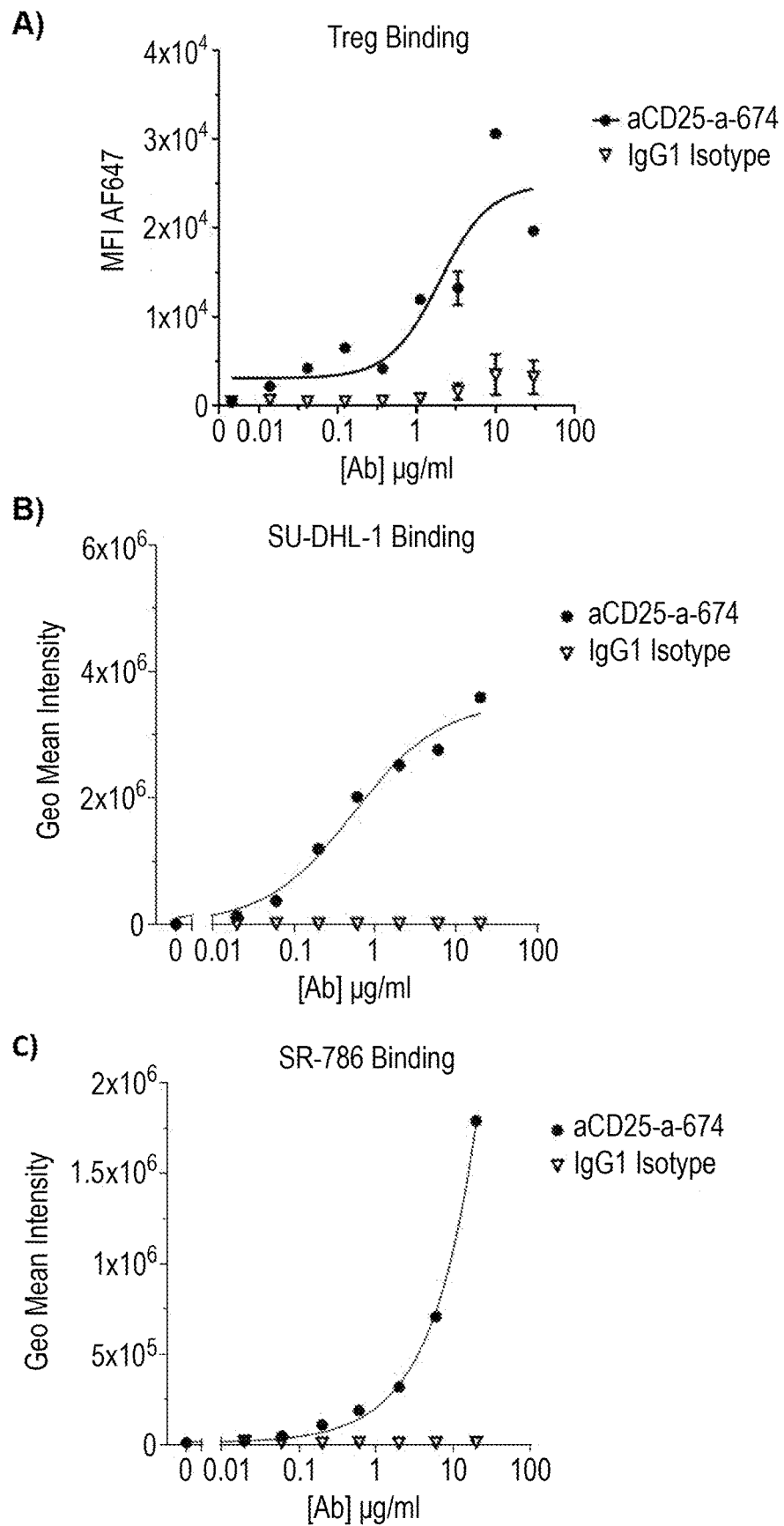
FIG. 3: Characterization of aCD25-a-674 binding to CD25 expressed on human in vitro differentiated Treg cells (A), SU-DHL-1 cells (B), or SR-786 cells (C) at increasing antibody concentrations and comparing with human IgG1 isotype control.
Figure 4:
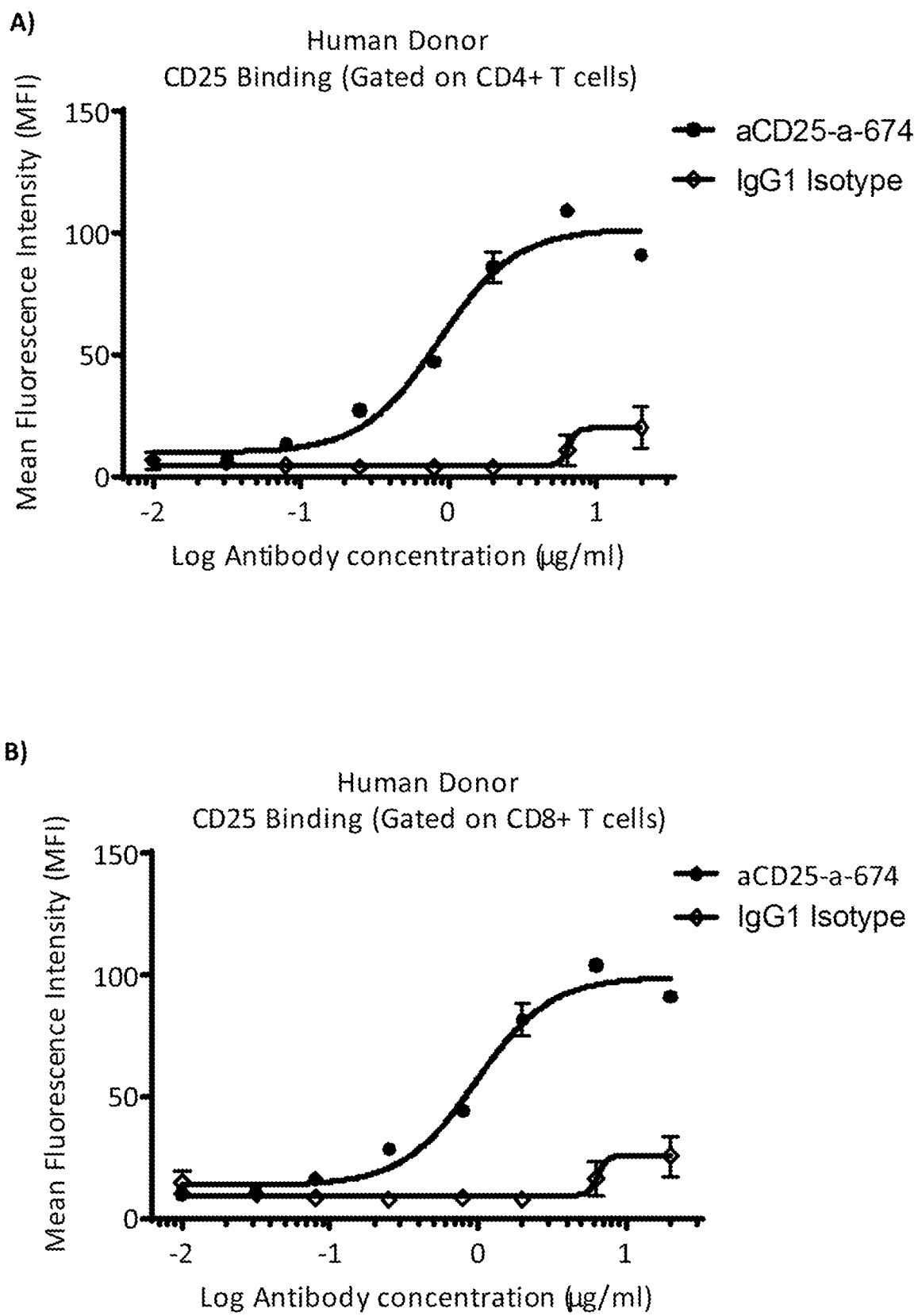
FIG. 4: Characterization of aCD25-a-674 binding to CD25 expressed on CD3/CD28 bead activated Human (A) and (B) or Cynomolgus Monkey (C) and (D) Pan T cells, then gated on $CD4^+$ and $CD8^+$ T cells, at increasing antibody concentration and comparing with human IgG1 isotype control.

Below are provided certain definitions of terms, technical means, and embodiments used herein, many or most of which confirm common understanding of those skilled in the art.

Administration: As used herein, the term "administration" refers to the administration of a composition to a subject. Administration to an animal subject (e.g., to a human) may be by any appropriate route. For example, in some embodiments, administration may be bronchial (including by bronchial instillation), buccal, enteral, intra-arterial, intra-dermal, intra-gastric, intra-medullary, intra-muscular, intra-nasal, intra-peritoneal, intra-thecal, intra-venous, intra-ventricular, within a specific organ or tissue (e. g. intra-hepatic, intra-tumoral, peri-tumoral, etc), mucosal, nasal, oral, rectal, subcutaneous, sublingual, topical, tracheal (including by intra-tracheal instillation), transdermal, vaginal and vitreal. The administration may involve intermittent dosing. Alternatively, administration may involve continuous dosing (e.g., perfusion) for at least a selected period of time. As is known in the art, antibody therapy is commonly administered parenterally, e.g. by intravenous, subcutaneous, or intratumoral injection (e.g., particularly when high doses within a tumor are desired).

Agent: The term "agent" as used herein may refer to a compound or entity of any chemical class including, for example, polypeptides, nucleic acids, saccharides, small molecules, metals, or combinations thereof. Specific embodiments of agents that may be utilized in accordance with the present invention include small molecules, drugs, hormones, antibodies, antibody fragments, aptamers, nucleic acids (e.g., siRNAs, shRNAs, antisense oligonucleotides, ribozymes), peptides, peptide mimetics, etc. An agent may be or comprise a polymer.

Antibody: As used herein, the term "antibody" refers to a polypeptide that includes canonical immunoglobulin sequence elements sufficient to confer specific binding to a particular target antigen, such as CD25, human CD25 in particular, and human CD25 extracellular domain. As is known in the art, intact antibodies as produced in nature are approximately 150 kD tetrameric agents comprised of two identical heavy chain polypeptides (about 50 kD each) and two identical light chain polypeptides (about 25 kD each) that associate with each other into what is commonly referred to as a "Y-shaped" structure. Each heavy chain is comprised of at least four domains (each about 110 amino acids long), an amino-terminal variable (VH) domain (located at the tips of the Y structure), followed by three constant domains: CH1, CH2, and the carboxy-terminal CH3 (located at the base of the Y's stem). A short region, known as the "switch", connects the heavy chain variable and constant regions. The "hinge" connects CH2 and CH3 domains to the rest of the antibody. Two disulfide bonds in this hinge region connect the two heavy chain polypeptides to one another in an intact antibody. Each light chain is comprised of two domains—an amino-terminal variable (VL) domain, followed by a carboxy-terminal constant (CL) domain, separated from one another by another "switch". Intact antibody tetramers are comprised of two heavy chain-light chain dimers in which the heavy and light chains are linked to one another by a single disulfide bond; two other disulfide bonds connect the heavy chain hinge regions to one another, so that the dimers are connected to one another and the tetramer is formed. Naturally produced antibodies are also glycosylated, typically on the CH2 domain, and each domain has a structure characterized by an "immunoglobulin fold" formed from two beta sheets (e.g., 3-, 4-, or 5-stranded sheets) packed against each other in a compressed antiparallel beta barrel. Each variable domain contains three hypervariable loops known as "complement determining regions" (CDR1, CDR2, and CDR3; as understood in the art, for example determined according to Kabat numbering scheme) and four somewhat invariant "framework" regions (FR1, FR2, FR3, and FR4). When natural antibodies fold, the FR regions form the beta sheets that provide the structural framework for the domains, and the CDR loop regions from both the heavy and light chains are brought together in three-dimensional space so that they create a single hypervariable antigen-binding site located at the tip of the Y structure. The Fc region of naturally-occurring antibodies binds to elements of the complement system, and also to receptors on effector cells, including for example effector cells that mediate cytotoxicity. As is known in the art, affinity and/or other binding attributes of Fc regions for Fc receptors can be modulated through glycosylation or other modification that can improve the developability of the antibody (Jarasch A et al., 2015).

In some embodiments, antibodies produced and/or utilized in accordance with the present invention include glycosylated Fc domains, including Fc domains with modified or engineered such glycosylation. For purposes of the present invention, in certain embodiments, any polypeptide or complex of polypeptides that includes sufficient immunoglobulin domain sequences as found in natural antibodies can be referred to and/or used as an "antibody", whether such polypeptide is naturally produced (e.g., generated by an organism reacting to an antigen), or produced by recombinant engineering, chemical synthesis, or other artificial system or methodology. In some embodiments, an antibody is polyclonal or oligoclonal, that is generated as a panel of antibodies, each associated to a single antibody sequence and binding more or less distinct epitopes within an antigen (such as different epitopes within human CD25 extracellular domain that are associated to different reference anti-CD25 antibodies).

Polyclonal or oligoclonal antibodies can be provided in a single preparation for medical uses as described in the literature (Kearns J D et al., 2015). In some embodiments, an antibody is monoclonal. In some embodiments, an antibody has constant region sequences that are characteristic of mouse, rabbit, primate, or human antibodies. In some embodiments, antibody sequence elements are humanized, primatized, chimeric, etc, as is known in the art. Moreover, the term "antibody" as used herein, can refer in appropriate embodiments (unless otherwise stated or clear from context) to any of the art-known or developed constructs or formats for utilizing antibody structural and functional features in alternative presentation, for instance as antigen-binding fragments as defined below. For example, an antibody utilized in accordance with the present invention is in a format selected from, but not limited to, intact IgG, IgE and IgM, bi- or multi-specific antibodies (e.g., Zybodies®, etc), single chain variable domains (scFv), polypeptide-Fc fusions, Fabs, cameloid antibodies, heavy-chain shark antibody (IgNAR), masked antibodies (e.g., Probodies®), or fusion proteins with polypeptides that allow expression and exposure on the cell surface (as scFv within constructs for obtaining artificial T cell receptors that are used to graft the specificity of a monoclonal antibody onto a T cell). A masked antibody can comprise a blocking or "mask" peptide that specifically binds to the antigen binding surface of the antibody and interferes with the antibody's antigen binding. The mask peptide is linked to the antibody by a cleavable linker (e.g. by a protease). Selective cleavage of the linker in the desired environment, e.g. in the tumour environment, allows the masking/blocking peptide to dissociate, enabling antigen binding to occur in the tumor, and thereby limiting potential toxicity issues. In some embodiments, an antibody may lack a covalent modification (e.g., attachment of a glycan) that it would have if produced naturally. Alternatively, an antibody may contain a covalent modification (e.g., attachment of a glycan, a payload [e.g., a detectable moiety, a therapeutic moiety, a catalytic moiety, etc.], or other pendant group [e.g., poly-ethylene glycol, etc.]).

Non-IL-2 Blocking Antibody Agent: The anti-CD25 Antibody Agents and antigen-binding fragments of the present invention are non-IL-2 blocking antibody agents. The term "Non-IL-2 blocking antibody agent" is used herein to refer to those anti-CD25 antibody agents (e.g. anti-CD25 non-IL-2 blocking antibodies) that are capable of specific binding to the CD25 subunit of the IL-2 receptor without blocking the binding of IL-2 to CD25 or signalling of IL-2 via CD25. The anti-CD25 Antibody Agents allow at least 50% of IL-2 signaling in response to IL-2 binding to CD25 compared to the level of signaling in the absence of the anti-CD25 Antibody Agent. Preferably the anti-CD25 Antibody Agents allow at least 75% of IL-2 signaling in response to CD25 compared to the level of signaling in the absence of the anti-CD25 Antibody Agent.

The CD25 subunit of the IL-2 receptor is also known as the alpha subunit of the IL-2 receptor and is found on activated T cells, regulatory T cells, activated B cells, some thymocytes, myeloid precursors and oligodendrocytes. CD25 associates with CD122 and CD132 to form a heterotrimeric complex that acts as the high-affinity receptor for IL-2. The consensus sequence of human CD25 is shown in FIG. 2.

"Specific binding", "bind specifically", and "specifically bind" are understood to mean that the antibody or antigen-binding fragment has a dissociation constant ($K_d$) for the antigen of interest of less than about $10^{-6}$ M, $10^{-7}$ M, $10^{-8}$ M, $10^{-9}$ M, $10^{-10}$ M, $10^{-11}$ M or $10^{-12}$ M. In a preferred embodiment, the dissociation constant is less than $10^{-8}$ M, for instance in the range of $10^{-9}$ M, $10^{-10}$ M, $10^{-11}$ M or $10^{-12}$ M. In accordance with some embodiments of the invention, "Specific binding", "bind specifically", and "specifically bind" may refer to affinity and/or avidity. In some embodiments, the affinity of the anti-CD25 Antibody Agents is from $10^{-8}$ to $10^{-8}$ (for example about $10^{-7}$). In some embodiments of the invention, the avidity of the anti-CD25 Antibody Agents is about from $10^{-10}$ to $10^{-8}$ (for example about $10^{-9}$). In some embodiments of the invention, the affinity and/or avidity of the anti-CD25 Antibody Agents is about from 1 nM to 700 nM, or about from 1 to 600 nM.

"Non-IL-2 blocking", as used herein and references to "non-blocking", "does not block" and the like (with respect to the non-blocking of IL-2 binding to CD25 in the presence of the anti-CD25 antibody) include embodiments wherein the anti-CD25 antibody or antigen-binding fragment inhibit less than 50% of IL-2 signalling compared to IL-2 signalling in the absence of the antibodies. In particular embodiments of the invention as described herein, the anti-CD25 antibody or antigen-binding fragment inhibits less than about 40%, 35%, 30%, preferably less than about 25% of IL-2 signalling compared to IL-2 signaling in the absence of the antibodies. Anti-CD25 non-IL-2 blocking antibodies allow binding to CD25 without interfering with IL-2 binding to CD25, or without substantially interfering with IL-2 binding to CD25. References herein to a non-IL-2 blocking antibody may alternatively be expressed as an anti-CD25 antibody that "does not inhibit the binding of interleukin 2 to CD25" or as an anti-CD25 antibody that "does not inhibit the signalling of IL-2".

Some anti-CD25 Antibody Agents may allow binding of IL-2 to CD25, but still block signalling via the CD25 receptor. Such Antibody Agents are not within the scope of the present invention. Instead, the non-IL-2 blocking anti-CD25 Antibody Agents allow binding of IL-2 to CD25 to facilitate at least 50% of the level of signalling via the CD25 receptor compared to the signalling in the absence of the anti-CD25 Antibody Agent.

IL-2 signalling via CD25, may be measured by methods as discussed in the Example and as known in the art. Comparison of IL-2 signalling in the presence and absence of the anti-CD25 antibody agent can occur under the same or substantially the same conditions.

In some embodiments, IL-2 signalling can be determined by measuring the levels of phosphorylated STAT5 protein in cells, using a standard Stat-5 phosphorylation assay. For example a Stat-5 phosphorylation assay to measure IL-2 signalling may involve culturing PMBC cells in the presence of the anti-CD25 antibody at a concentration of 10 ug/ml for 30 mins and then adding varying concentrations of IL-2 (for example at 10 U/ml or at varying concentrations of 0.25 U/ml, 0.74 U/ml, 2.22 U/ml, 6.66 U/ml or 20 U/ml) for 10 mins. Cells may then be permeabilized and levels of STAT5 protein can then be measured with a fluorescent labelled antibody to a phosphorylated STAT5 peptide analysed by flow cytometry. The percentage blocking of IL-2 signalling can be calculated as follows: % blocking=100×[(% Stat5$^+$ cells No Antibody group—% Stat5$^+$ cells 10 ug/ml Antibody group)/(% Stat5$^+$ cells No Ab group)].

In some embodiments, the anti-CD25 Antibody Agents as described herein are characterized in that they deplete tumour-infiltrating regulatory T cells efficiently, in particular within tumors.

In some embodiments, anti-CD25 Antibody Agents are characterised in that they bind Fcγ receptor with high affinity, preferably at least one activating Fcγ receptor with high affinity. Preferably the antibody binds to at least one activatory Fcγ receptor with a dissociation constant of less than about $10^{-6}$M, $10^{-7}$M, $10^{-8}$M, $10^{-9}$M or $10^{-10}$M. In some embodiments, the anti-CD25 Antibody agents are characterized by other features related to Fcγ receptors, in particular:

(a) bind to Fcγ receptors with an activatory to inhibitory ratio (A/I) superior to 1; and/or
(b) bind to at least one of FcγRI, FcγRIIc, and FcγRIIIa with higher affinity than it binds to FcγRIIb.

In some embodiments, the CD25 Antibody agent is an IgG1 antibody, preferably a human IgG1 antibody, which is capable of binding to at least one Fc activating receptor. For example, the antibody may bind to one or more receptor selected from FcγRI, FcγRIIa, FcγRIIc, FcγRIIIa and FcγRIIIb. In some embodiments, the antibody is capable of binding to FcγRIIIa. In some embodiments, the antibody is capable of binding to FcγRIIIa and FcγRIIa and optionally FcγRI. In some embodiments, the antibody is capable of binding to these receptors with high affinity, for example with a dissociation constant of less than about $10^{-7}$M, $10^{-8}$M, 10–9M or $10^{-10}$M. In some embodiments, the antibody binds an inhibitory receptor, FcγRIIb, with low affinity. In one aspect, the antibody binds FcγRIIb with a dissociation constant higher than $10^{-7}$M, higher than $10^{-6}$M or higher than $10^{-5}$M.

In some embodiments, desirable anti-CD25 Antibody Agents as described herein are characterized in that they are cytotoxic towards or induce phagocytosis of CD25 expressing cells (e.g. expressing high levels of CD25) such as immune suppressive cells or tumour cells (e.g., in each case, that express CD25 on their surfaces). In some embodiments, an anti-CD25 Antibody Agent is characterized by an activity (e.g., level and/or type) reasonably comparable to that of aCD25-a-674 with respect to immune cells (e.g., when contacted with immune cells, and particularly with immune cells that express CD25) and tumour cells. In some embodiments, a relevant activity is or comprises depleting Treg cells (e.g. in a solid tumor), or certain CD25-expressing cells (e.g., high-expressing cells) by ADCP, ADCC or CDC, promotion of T cell, B cell or NK cell expansion), skewing of T cell repertoire, etc., and combinations thereof. In some embodiments, an increased level and/or activity, or decreased level and/or increased or no change in level or activity, is assessed or determined relative to that observed under otherwise comparable conditions in absence of the entity(ies) or moiety(ies). Alternatively, or additionally, in some embodiments, an increased level and/or activity is comparable to or greater than that observed under comparable conditions when a reference anti-CD25 Antibody Agents (e.g., an appropriate reference anti-CD25 antibody, which in many embodiments is a CD25 antibody that blocks IL-2 binding to CD25, such as Daclizumab or Basiliximab) is present. In many embodiments, an anti-CD25 Antibody Agent for use in accordance with the present disclosure is or comprises an entity or moiety that binds, directly or indirectly, to CD25, typically to its extracellular domain. In some embodiments, an anti-CD25 Antibody Agent is, comprises, or competes for binding to CD25 with an anti-CD25 antibody as exemplified herein, an antigen-binding fragment (e.g., comprising one or more CDRs, all heavy chain CDRs, all light chain CDRs, all CDRs, a heavy chain variable region, a light chain variable region, or both heavy and light chain variable regions) thereof, an affinity matured variant thereof (or an antigen-binding fragment thereof), or any alternative format (e.g., chimeric, humanized, multispecific, alternate isotype, etc) of any of the foregoing. Alternatively, or additionally, in some embodiments, an anti-CD25 Antibody Agent as described herein may be characterized by one or more features that may be features that are advantageous for screening, manufacturing, (pre-clinical testing, and/or for identifying relevant epitope within human CD25, such as the sequence identified as aCD25ep-a and aCD25ep-b), and/or for formulation, administration, and/or efficacy in particular contexts (e.g., for cancer therapy), as disclosed herein.

Antigen: The term "antigen", as used herein, refers to an agent that elicits an immune response and/or that binds to a T cell receptor (e.g., when presented by an MHC molecule) and/or B cell receptor. An antigen that elicits a humoral response involve the production of antigen-specific antibodies or, as shown in the Examples for CD25 extracellular domain, can be used for screening antibody libraries and identifying candidate antibody sequences to be further characterized.

Antigen-binding Fragment: As used herein, the term "Antigen-binding Fragment" encompasses agents that include or comprise one or more portions of an antibody as described herein sufficient to confer on the antigen-binding fragment and ability to specifically bind to the Antigen targeted by the antibody. For example, in some embodiments, the term encompasses any polypeptide or polypeptide complex that includes immunoglobulin structural elements sufficient to confer specific binding. Exemplary antigen-binding fragments include, but are not limited to Small Modular ImmunoPharmaceuticals ("SMIPs™"), single chain antibodies, cameloid antibodies, single domain antibodies (e.g., shark single domain antibodies), single chain or Tandem diabodies (TendAbe), VHHs, Anticalins®, Nanobodies®, minibodies, BiTE®s, ankyrin repeat proteins or DARPINs®, Avimers®, a DART, a TCR-like antibody, Adnectins®, Affilins®, Trans-bodies®, Affibodies®, a TrimerX®, MicroProteins, Centyrins®, CoVX bodies, BiCyclic peptides, Kunitz domain derived antibody constructs, or any other antibody fragments so long as they exhibit the desired biological activity. In some embodiments, the term encompasses other protein structures such as stapled peptides, antibody-like binding peptidomimetics, antibody-like binding scaffold proteins, monobodies, and/or other non-antibody proteins scaffold, for example as reviewed in the literature (Vazquez-Lombardi R et al., 2015). In some embodiments, an antigen-binding fragment is or comprises a polypeptide whose amino acid sequence includes one or more structural elements recognized by those skilled in the art as a complementarity determining region (CDR). In some embodiments an antigen-binding fragment is or comprises a polypeptide whose amino acid sequence includes at least one reference CDR (e.g., at least one heavy chain CDR and/or at least one light chain CDR) that is substantially identical to one found in an anti-CD25 antibody as described herein (e.g., in an aCD25-a-674 amino acid sequence element), and in particular at least one heavy chain CDR, such as an HCDR3 (e.g., an aCD25-a-674-HCDR3 sequence). In some embodiments an antigen-binding fragment is or comprises a polypeptide whose amino acid sequence includes at least one CDR (e.g., at least one heavy chain CDR and/or at least one light chain CDR) that is either identical in sequence or contains a small number (e.g., 1, 2, 3, or 4) more amino acid alterations (e.g., substitutions, additions, or deletions; in many cases, substitutions) relative to such a reference CDR, while maintaining binding to the target of the antibody (e.g., aCD25-a-674) from which the reference CDR was derived. In some embodiments, an antigen-binding fragment is or comprises a polypeptide or complex thereof that includes all three CDRs (or, in some embodiments, sequences substantially identical thereto) from a heavy or light chain of a reference antibody (e.g., from aCD25-a-674); in some embodiments, an antigen-binding fragment is or comprises a polypeptide or complex thereof that includes all six CDRs (or, in some embodiments, sequences substantially identical thereto) from a reference antibody (e.g., from aCD25-a-674). In some embodiments, an antigen-binding fragment is or comprises a polypeptide or complex thereof that includes the heavy and/or light chain variable domains (or, in some embodiments, sequences substantially identical thereto) of a reference antibody (e.g., of aCD25-a-674). In some embodiments, the term "antigen-binding fragment" encompasses non-peptide and non-protein structures, such as nucleic acid aptamers, for example, RNA aptamers and DNA aptamers. An aptamer is an oligonucleotide (e.g., DNA, RNA, or an analog or derivative thereof) that binds to a particular target, such as a polypeptide. Aptamers are short synthetic single-stranded oligonucleotides that specifically bind to various molecular targets such as small molecules, proteins, nucleic acids, and even cells and tissues. These small nucleic acid molecules can form secondary and tertiary structures capable of specifically binding proteins or other cellular targets, and are essentially a chemical equivalent of antibodies. Aptamers are highly specific, relatively small in size, and non-immunogenic. Aptamers are generally selected from a biopanning method known as SELEX (Systematic Evolution of Ligands by Exponential enrichment) (See for example Ellington et al, 1990; Tuerk et al., 1990; Ni et al., 2011). Methods of generating an apatmer for any given target are well known in the art. Peptide aptamers including affimers are also encompassed. An affimer is a small, highly stable protein engineered to display peptide loops which provide a high affinity binding surface for a specific target protein. It is a protein of low molecular weight, 12-14 kDa, derived from the cysteine protease inhibitor family of cystatins. Affimer proteins are composed of a scaffold, which is a stable protein based on the cystatin protein fold. They display two peptide loops and an N-terminal sequence that can be randomized to bind different target proteins with high affinity and specificity similar to antibodies. Stabilization of the peptide upon the protein scaffold constrains the possible conformations which the peptide may take, thus increasing the binding affinity and specificity compared to libraries of free peptides.

Biological Sample. As used herein, the terms "biological sample" or "sample" typically refers to a sample obtained or derived from a biological source (e.g., a tissue or organism or cell culture) of interest, as described herein. A source of interest may be an organism, such as an animal or human. The biological sample may comprise biological tissue or fluid.

Cancer: The terms "cancer", "malignancy", "neoplasm", "tumor", "tumour", and "carcinoma", are used interchangeably herein to refer to cells that exhibit relatively abnormal, uncontrolled, and/or autonomous growth, so that they exhibit an aberrant growth phenotype characterized by a significant loss of control of cell proliferation. In general, cells of interest for detection or treatment in the present application include precancerous (e.g., benign), malignant, pre-metastatic, metastatic, and non-metastatic cells. The teachings of the present disclosure may be relevant to any and all cancers. To give but a few, non-limiting examples, in some embodiments, teachings of the present disclosure are applied to one or more cancers such as, for example, hematopoietic cancers including leukemias, lymphomas (Hodgkins and non-Hodgkins), myelomas and myeloproliferative disorders; sarcomas, melanomas, adenomas, carcinomas of solid tissue, squamous cell carcinomas of the mouth, throat, larynx, and lung, liver cancer, genitourinary cancers such as prostate, cervical, bladder, uterine, and endometrial cancer and renal cell carcinomas, bone cancer, pancreatic cancer, skin cancer, cutaneous or intraocular melanoma, cancer of the endocrine system, cancer of the thyroid gland, cancer of the parathyroid gland, head and neck cancers, breast cancer, gastro-intestinal cancers and nervous system cancers, benign lesions such as papillomas, and the like. The antibodies of the invention can be used for the treatment of CD25+ expressing tumors. The treatment of cancer involving CD25 expressing tumors can include but is not limited to lymphomas, such as such as Hodgkin lymphomas, and lymphocytic leukemias, such as chronic lymphocytic leukemia (CLL).

Combination Therapy: As used herein, the term "combination therapy" refers to those situations in which a subject is simultaneously exposed to two or more therapeutic regimens (e.g., two or more therapeutic agents). In some embodiments, two or more agents may be administered simultaneously. Alternatively, such agents may be administered sequentially; otherwise, such agents are administered in overlapping dosing regimens.

Comparable: As used herein, the term "comparable" refers to two or more agents, entities, situations, effects, sets of conditions, etc., that may not be identical to one another but that are sufficiently similar to permit comparison (e.g., by level and/or activity) there between so that conclusions may reasonably be drawn based on differences or similarities observed. Such comparable sets of conditions, effects, circumstances, individuals, or populations are characterized by a plurality of substantially identical features and one or a small number of varied features. Those of ordinary skill in the art will understand, in context, what degree of identity is required in any given circumstance for two or more such agents, entities, situations, sets of conditions, effects, or populations, etc. to be considered comparable.

Comprising: A composition or method described herein as "comprising" one or more named elements or steps is open-ended, meaning that the named elements or steps are essential, but other elements or steps may be added within the scope of the composition or method. It is also understood that any composition or method described as "comprising" (or which "comprises") one or more named elements or steps also describes the corresponding, more limited composition or method "consisting essentially of" (or which "consists essentially of") the same named elements or steps, meaning that the composition or method includes the named essential elements or steps and may also include additional elements or steps that do not materially affect the basic and novel characteristic(s) of the composition or method.

Depleted: As used herein, references to "depleted" or "depleting" (with respect to the depletion of regulatory Tcells by an anti-CD25 antibody agent) it is meant that the number, ratio or percentage of Tregs is decreased relative to when an anti-CD25 antibody that does not inhibit the binding of interleukin 2 to CD25 is not administered. In particular embodiments of the invention as described herein, over about 5%, 10%, 20%, 30%, 40%, 50%, 60%, 70%, 80%, 90% or 99% of the tumour-infiltrating regulatory T cells are depleted.

Dosage Form: As used herein, the term "dosage form" refers to a physically discrete unit of an active agent (e.g., a therapeutic or diagnostic agent) for administration to a subject. Each unit contains a predetermined quantity of active agent. In some embodiments, such quantity is a unit dosage amount (or a whole fraction thereof) appropriate for administration in accordance with a dosing regimen that has been determined to correlate with a desired or beneficial outcome when administered to a relevant population (i.e., with a therapeutic dosing regimen). Those of ordinary skill in the art appreciate that the total amount of a therapeutic composition or agent administered to a particular subject is determined by one or more attending physicians and may involve administration of multiple dosage forms.

Dosing Regimen: As used herein, the term "dosing regimen" refers to a set of unit doses (typically more than one) that are administered individually to a subject, typically separated by periods of time. In some embodiments, a given therapeutic agent has a recommended dosing regimen, which may involve one or more doses. In some embodiments, a dosing regimen comprises a plurality of doses each of which are separated from one another by a time period of the same length. Alternatively, a dosing regimen comprises a plurality of doses and at least two different time periods separating individual doses. In some embodiments, all doses within a dosing regimen are of the same unit dose amount. Alternatively, different doses within a dosing regimen are of different amounts. In some embodiments, a dosing regimen comprises a first dose in a first dose amount, followed by one or more additional doses in a second dose amount different from the first dose amount. A dosing regimen may comprise a first dose in a first dose amount, followed by one or more additional doses in a second dose amount same as the first dose amount. In some embodiments, a dosing regimen is correlated with a desired or beneficial outcome when administered across a relevant population (i.e., is a therapeutic dosing regimen).

Epitope: As used herein, the term "epitope" refers to a portion of an antigen that is bound by an antibody or antigen-binding fragment. In some embodiments, where the antigen is a polypeptide, an epitope is conformational in that it is comprised of portions of an antigen that are not covalently contiguous in the antigen but that are near to one another in three-dimensional space when the antigen is in a relevant conformation. For example, for CD25, conformational epitopes are those comprised of amino acid residues that are not contiguous in CD25 extracellular domain; linear epitopes are those comprised of amino acid residues that are contiguous in CD25 extracellular domain. In some embodiments, epitopes utilized in accordance with the present invention are provided by means of reference to those bound by anti-CD25 Antibody Agents provided herein (e.g., by aCD25-a-674 and defined as aCD25ep-a and aCD25ep-b). Means for determining the exact sequence and/or particularly amino acid residues of the epitope for aCD25-a-674 are known in the literature and in the Examples, including competition with peptides, from antigen sequences, binding to CD25 sequence from different species, truncated, and/or mutagenized (e.g. by alanine scanning or other site-directed mutagenesis), phage display-based screening, yeast presentation technologies, or (co-) crystallography techniques.

Identity: Percent (%) identity as known in the art is the relationship between two or more polypeptide sequences or two or more polynucleotide sequences, as determined by comparing the sequences. In the art, identity also means the degree of sequence relatedness between polypeptide or polynucleotide sequences, as the case may be, as determined by the match between strings of such sequences. While there exist a number of methods to measure identity between two polypeptides or two polynucleotide sequences, methods commonly employed to determine identity are codified in computer programs. Preferred computer programs to determine identity between two sequences include, but are not limited to, GCG program package (Devereux, et al., Nucleic Acids Research, 12, 387 (1984), BLASTP, BLASTN, and FASTA (Atschul et al., J. Molec. Biol. 215, 403 (1990)). The percent identity of two amino acid sequences or of two nucleic acid sequences is determined by aligning the sequences for optimal comparison purposes (e.g., gaps can be introduced in the first sequence for best alignment with the sequence) and comparing the amino acid residues or nucleotides at corresponding positions. The "best alignment" is an alignment of two sequences which results in the highest percent identity. The percent identity is determined by the number of identical amino acid residues or nucleotides in the sequences being compared (i.e., % identity=number of identical positions/total number of positions×100). Generally, references to % identity herein refer to % identity along the entire length of the molecule, unless the context specifies or implies otherwise.

Immune effector cell: An immune effector cell refers to an immune cell which is involved in the effector phase of an immune response. Exemplary immune cells include a cell of a myeloid or lymphoid origin, e.g., lymphocytes (e.g., B cells and T cells including cytolytic T cells (CTLs)), killer cells, natural killer cells, macrophages, monocytes, eosinophils, neutrophils, polymorphonuclear cells, granulocytes, mast cells, and basophils.

Immune effector cells involved in the effector phase of an immune response may express specific Fc receptors and carry out specific immune functions. An effector cell can induce antibody-dependent cell-mediated cytotoxicity (ADCC), e.g., a neutrophil capable of inducing ADCC. An effector cell can also induce antibody-dependent cell-mediated phagocytosis (ADCP), which consists in phagocytosis of a target antigen, target cell, or microorganism, e.g. macrophages capable of ADCP. For example, monocytes, macrophages, neutrophils, eosinophils, and lymphocytes which express FcγR are involved in specific killing of target cells and presenting antigens to other components of the immune system, or binding to cells that present antigens. As discussed, the antibodies according to the present invention may be optimised for ability to induce ADCC and/or ADCP.

Regulatory T cells: As used herein, "regulatory T cells" ("Treg", "Treg cells", or "Tregs") refer to a lineage of CD4+T lymphocytes specialized in controlling autoimmunity, allergy and infection. Typically, they regulate the activities of T cell populations, but they can also influence certain innate immune system cell types. Tregs are usually identified by the expression of the biomarkers CD4, CD25 and Foxp3, and low expression of CD127. Naturally occurring Treg cells normally constitute about 5-10% of the peripheral CD4+T lymphocytes. However, within a tumour microenvironment (i.e. tumour-infiltrating Treg cells), they can make up as much as 20-30% of the total CD4+T lymphocyte population.

Activated human Treg cells may directly kill target cells such as effector T cells and APCs through perforin- or granzyme B-dependent pathways; cytotoxic T-lymphocyte-associated antigen 4 (CTLA4+) Treg cells induce indoleamine 2,3-dioxygenase (IDO) expression by APCs, and these in turn suppress T-cell activation by reducing tryptophan; Treg cells, may release interleukin-10 (IL-10) and transforming growth factor (TGFβ) in vivo, and thus directly inhibit T-cell activation and suppress APC function by inhibiting expression of MHC molecules, CD80, CD86 and IL-12. Treg cells can also suppress immunity by expressing high levels of CTLA4 which can bind to CD80 and CD86 on antigen presenting cells and prevent proper activation of effector T cells Patient: As used herein, the term "patient" or "subject" refers to any organism to which a provided composition is or may be administered, e.g., for experimental, diagnostic, prophylactic, cosmetic, and/or therapeutic purposes. Typical patients include animals (e.g., mammals such as mice, rats, rabbits, non-human primates, and/or humans). In some embodiments, a patient is a human. In some embodiments, a patient is suffering from or susceptible to one or more disorders or conditions. A patient may display one or more symptoms of a disorder or condition, or may have been diagnosed with one or more disorders or conditions (such as cancer, or presence of one or more tumors). In some embodiments, the patient is receiving or has received certain therapy to diagnose and/or to treat such disease, disorder, or condition.

Pharmaceutically Acceptable: As used herein, the term "pharmaceutically acceptable" applied to the carrier, diluent, or excipient used to formulate a composition as disclosed herein means that the carrier, diluent, or excipient must be compatible with the other ingredients of the composition and not deleterious to the recipient thereof.

Pharmaceutical Composition: As used herein, the term "pharmaceutical composition" refers to a composition in which an active agent is formulated together with one or more pharmaceutically acceptable carriers. In some embodiments, active agent is present in unit dose amount appropriate for administration in a therapeutic regimen that shows a statistically significant probability of achieving a predetermined therapeutic effect when administered to a relevant population. A pharmaceutical compositions may be formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous, intratumoral, or epidural injection as a sterile solution or suspension, or sustained-release formulation; topical application, for example, as a cream, ointment, or a controlled-release patch or spray applied to skin, lungs, or oral cavity; intravaginally, intrarectally, sublingually, ocularly, transdermally, nasally, pulmonary, and to other mucosal surfaces.

Solid Tumor: As used herein, the term "solid tumor" refers to an abnormal mass of tissue that usually does not contain cysts or liquid areas. Solid tumors may be benign or malignant. Different types of solid tumors are named for the type of cells that form them. Examples of solid tumors are sarcomas (including cancers arising from transformed cells of mesenchymal origin in tissues such as cancellous bone, cartilage, fat, muscle, vascular, hematopoietic, or fibrous connective tissues), carcinomas (including tumors arising from epithelial cells), melanomas, lymphomas, mesothelioma, neuroblastoma, retinoblastoma, etc. Cancers involving solid tumors include, without limitations, brain cancer, lung cancer, stomach cancer, duodenal cancer, esophagus cancer, breast cancer, colon and rectal cancer, renal cancer, bladder cancer, kidney cancer, pancreatic cancer, prostate cancer, ovarian cancer, melanoma, mouth cancer, sarcoma, eye cancer, thyroid cancer, urethral cancer, vaginal cancer, neck cancer, lymphoma, and the like.

Therapeutically Effective Amount: As used herein, the term "therapeutically effective amount" means an amount (e.g., of an agent or of a pharmaceutical composition) that is sufficient, when administered to a population suffering from or susceptible to a disease and/or condition in accordance with a therapeutic dosing regimen, to treat such disease and/or condition. A therapeutically effective amount is one that reduces the incidence and/or severity of, stabilizes, and/or delays onset of, one or more symptoms of the disease, disorder, and/or condition. Those of ordinary skill in the art will appreciate that a "therapeutically effective amount" does not in fact require successful treatment be achieved in a particular subject.

Treatment: As used herein, the term "treatment" (also "treat" or "treating") refers to any administration of a substance (e.g., provided anti-CD25 Antibody Agent, as exemplified by aCD25-a-674, or any other agent) that partially or completely alleviates, ameliorates, relives, inhibits, delays onset of, reduces severity of, and/or reduces incidence of one or more symptoms. In some embodiments, treatment may involve the direct administration of anti-CD25 Antibody Agent such as aCD25-a-674 (for example, as an injectable, aqueous composition, optionally comprising a pharmaceutically acceptable carrier, excipient and/or adjuvant, for use for intravenous, intratumoral or peritumoral injection) or the administration using a regimen comprising obtaining cells from the subject (e.g. from the blood, a tissue, or a tumor, with or without a selection on the basis of presence, or absence, of the expression of a marker), contacting said cells with an anti-CD25 Antibody Agent such as aCD25-a-674 ex vivo, and administering such cells to the subject (with or without a selection on the basis of presence, or absence, of the expression of a marker).

Dosing and Administration. Pharmaceutical compositions comprising an anti-CD25 Antibody Agent as described herein (e.g. an anti-CD25 or antigen-binding fragment thereof, for example comprising the aCD25-a-674-HCDR3 amino acid sequence) for use in accordance with the present invention may be prepared for storage and/or delivery using any of a variety of techniques and/or technologies known and/or available to those skilled in the art. In some embodiments, a provided anti-CD25 Antibody Agent is administered according to a dosing regimen approved by a regulatory authority such as the United States Food and Drug Administration (FDA) and/or the European Medicines Agency (EMEA), e.g., for the relevant indication. In some embodiments, a provided anti-CD25 Antibody Agent is administered in combination with one or more other agents or therapies, which may themselves be administered according to a dosing regimen approved by a regulatory authority such as the United States Food and Drug Administration (FDA) and/or the European Medicines Agency (EMEA), e.g., for the relevant indication. In some embodiments however, use of a provided anti-CD25 Antibody Agent may permit reduced dosing (e.g., lower amount of active in one or more doses, smaller number of doses, and/or reduced frequency of doses) of an approved agent or therapy used in combination with the anti-CD25 Antibody Agent therapy. In some embodiments, dosing and/or administration may be adapted to other drugs that also administered, the patient status, and/or the format of anti-CD25 Antibody Agent (e.g. modified as an immunoconjugate, a single domain antibody, or a bispecific antibody).

Moreover, in some embodiments, it may be desirable to tailor dosing regimens, and particularly to design sequential dosing regimens, based on timing and/or threshold expression levels of CD25, whether for particular cell types, particular tumors or types thereof, or particular patient populations (e.g., carrying genetic markers). In some such embodiments, therapeutic dosing regimens may be combined with or adjusted in light of detection methods that assess expression of one or more inducible markers or other criteria prior to and/or during therapy.

In some embodiments, dosing and administration according to the present invention utilizes active agent having a desired degree of purity combined with one or more physiologically acceptable carriers, excipients or stabilizers in any or variety of forms. These include, for example, liquid, semi-solid and solid dosage forms, such as liquid solutions (e.g., injectable and infusible solutions), dispersions or suspensions, tablets, pills, powders, liposomes and suppositories. A preferred form may depend on the intended mode of administration and/or therapeutic application, typically in the form of injectable or infusible solutions, such as compositions similar to those used for treating of human subjects with antibodies.

In some embodiments, ingredient(s) can be prepared with carriers that protect the agent(s) against rapid release and/or degradation, such as a controlled release formulation, including implants, transdermal patches, and microencapsulated delivery systems. Biodegradable, biocompatible polymers can be used, such as polyanhydrides, polyglycolic acid, polyorthoesters, and polylactic acid. In general, each active agent is formulated, dosed, and administered in therapeutically effective amount using pharmaceutical compositions and dosing regimens that are consistently with good medical practice and appropriate for the relevant agent(s) (e.g., for agents such as antibodies). Pharmaceutical compositions containing active agents can be administered by any appropriate method known in the art, including, without limitation, oral, mucosal, by-inhalation, topical, buccal, nasal, rectal, or parenteral (e.g. intravenous, infusion, intratumoral, intranodal, subcutaneous, intraperitoneal, intramuscular, intradermal, transdermal, or other kinds of administration involving physical breaching of a tissue of a subject and administration of the pharmaceutical composition through such breach).

In some embodiments, a dosing regimen for a particular active agent may involve intermittent or continuous (e.g., by perfusion or slow release system) administration, for example to achieve a particular desired pharmacokinetic profile or other pattern of exposure in one or more tissues or fluids of interest in the subject. In some embodiments, different agents administered in combination may be administered via different routes of delivery and/or according to different schedules. Alternatively, or additionally, in some embodiments, one or more doses of a first active agent is administered substantially simultaneously with, and in some embodiments via a common route and/or as part of a single composition with, one or more other active agents.

Factors to be considered when optimizing routes and/or dosing schedule for a given therapeutic regimen may include, for example, the particular cancer being treated (e.g., type, stage, location, etc.), the clinical condition of a subject (e.g., age, overall health, weight, etc.), the site of delivery of the agent, the nature of the agent (e.g. an antibody or other protein-based compound), the mode and/or route of administration of the agent, the presence or absence of combination therapy, and other factors known to medical practitioners.

Those skilled in the art will appreciate, for example, that a specific route of delivery may impact dose amount and/or required dose amount may impact route of delivery. For example, where particularly high concentrations of an agent within a particular site or location (e.g., within a tissue or organ) are of interest, focused delivery (e.g., intratumoral delivery) may be desired and/or useful. In some embodiments, one or more features of a particular pharmaceutical composition and/or of a utilized dosing regimen may be modified over time (e.g., increasing or decreasing amount of active in any individual dose, increasing or decreasing time intervals between doses, etc.), for example in order to optimize a desired therapeutic effect or response (e.g., a therapeutic or biological response that is related to the functional features of an anti-CD25 Antibody Agent as described herein). In general, type, amount, and frequency of dosing of active agents in accordance with the present invention in governed by safety and efficacy requirements that apply when relevant agent(s) is/are administered to a mammal, preferably a human. In general, such features of dosing are selected to provide a particular and typically detectable, therapeutic response as compared with what is observed absent therapy. In context of the present invention, an exemplary desirable therapeutic response may involve, but is not limited to, inhibition of and/or decreased tumor growth, tumor size, metastasis, one or more of the symptoms and side effects that are associated with the tumor, as well as increased apoptosis of cancer cells, therapeutically relevant decrease or increase of one or more cell marker or circulating markers and the like. Such criteria can be readily assessed by any of a variety of immunological, cytological, and other methods that are disclosed in the literature. For example, the therapeutically effective amount of anti-CD25 Antibody Agents, alone or in combination with a further agent, can be determined as being sufficient to enhance killing of cancer cells as described in the Examples.

A therapeutically effective amount of an anti-CD25 Antibody Agent as active agent or composition comprising such agent can be readily determined using techniques available in the art including, for example, considering one or more factors such as the disease or condition being treated, the stage of the disease, the age and health and physical condition of the mammal being treated, the severity of the disease, the particular compound being administered, and the like.

In some embodiments, therapeutically effective amount is an effective dose (and/or a unit dose) of an active agent that may be at least about 0.01 mg/kg body weight, at least about 0.05 mg/kg body weight; at least about 0.1 mg/kg body weight, at least about 1 mg/kg body weight, at least about 5 mg/kg body weight, at least about 10 mg/kg body weight, or more (e.g. 0.01, 0.1, 0.3, 0.5, 1, 2, 3, 4, 5, 6, 7, 8, 9, 10, 20, 30, 40, or 50 mg/kg body weight). It will be understood by one of skill in the art that in some embodiments such guidelines may be adjusted for the molecular weight of the active agent. The dosage may also be varied for route of administration, the cycle of treatment, or consequently to dose escalation protocol that can be used to determine the maximum tolerated dose and dose limiting toxicity (if any) in connection to the administration of the isolated antibody or antigen-binding fragment thereof comprising the aCD25-a-674-HCDR3 amino acid sequence at increasing doses.

Therapeutic compositions typically should be sterile and stable under the conditions of manufacture and storage. The composition can be formulated as a solution, microemulsion, dispersion, liposome, or other ordered structure suitable to high drug concentration. Sterile injectable solutions can be prepared by incorporating the antibody in the required amount in an appropriate solvent with one or a combination of ingredients enumerated above, followed by filtered sterilization. Generally, dispersions are prepared by incorporating the active compound into a sterile vehicle that contains a basic dispersion medium and other required ingredients from those enumerated above. In the case of powders for preparing sterile injectable solutions, the preferred methods of preparation are vacuum drying and freeze drying that yields a powder of the active ingredient plus any additional desired ingredient from a previously sterile filtered solution. The proper fluidity of a solution can be maintained, for example, by using a coating, by the maintenance of the required particle size in the case of dispersion and by the use of surfactants. Prolonged absorption of injectable compositions can be brought about by including in the composition an agent that delays absorption, for example, monostearate salts and gelatin.

The formulation of each agent should desirably be sterile, as can be accomplished by filtration through sterile filtration membranes, and then packaged, or sold in a form suitable for bolus administration or for continuous administration. Injectable formulations may be prepared, packaged, or sold in unit dosage form, such as in ampules or in multi dose containers containing a preservative. Formulations for parenteral administration include, but are not limited to, suspensions, solutions, emulsions in oily or aqueous vehicles, pastes, and implantable sustained-release or biodegradable formulations as discussed herein. Sterile injectable formulations may be prepared using a non-toxic parenterally acceptable diluent or solvent, such as water or 1,3 butanediol. Other parentally-administrable formulations which are useful include those which comprise the active ingredient in microcrystalline form, in a liposomal preparation, or as a component of biodegradable polymer systems. Compositions for sustained release or implantation may comprise pharmaceutically acceptable polymeric or hydrophobic materials such as an emulsion, an ion exchange resin, a sparingly soluble polymer or salt.

Each pharmaceutical composition for use in accordance with the present invention may include pharmaceutically acceptable dispersing agents, wetting agents, suspending agents, isotonic agents, coatings, antibacterial and antifungal agents, carriers, excipients, salts, or stabilizers are non-toxic to the subjects at the dosages and concentrations employed. A non-exhaustive list of such additional pharmaceutically acceptable compounds includes buffers such as phosphate, citrate, and other organic acids; antioxidants including ascorbic acid and methionine; salts containing pharmacologically acceptable anions (such as acetate, benzoate, bicarbonate, bisulfate, isothionate, lactate, lactobionate, laurate, malate, maleate, salicylate, stearate, subacetate, succinate, tannate, tartrate, teoclate, tosylate, thiethiodode, and valerate salts); preservatives (such as octadecyidimethylbenzyl ammonium chloride; hexamethonium chloride; benzalkonium chloride, benzethonium chloride; sodium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin; hydrophilic polymers such as polyvinylpyrrolidone; amino acids such as glycine, glutamine, asparagine, glutamic acid, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

In some embodiments, where two or more active agents are utilized in accordance with the present invention, such agents can be administered simultaneously or sequentially. In some embodiments, administration of one agent is specifically timed relative to administration of another agent. In some embodiments, desired relative dosing regimens for agents administered in combination may be assessed or determined empirically, for example using ex vivo, in vivo and/or in vitro models; in some embodiments, such assessment or empirical determination is made in vivo, in a particular patient or patient population (e.g., so that a correlation is made).

In some embodiments, one or more active agents utilized in practice of the present invention is administered according to an intermittent dosing regimen comprising at least two cycles. Where two or more agents are administered in combination, and each by such an intermittent, cycling, regimen, individual doses of different agents may be interdigitated with one another. In some embodiments, one or more doses of the second agent is administered a period of time after a dose of an anti-CD25 Antibody Agent as described herein. In some embodiments, each dose of the second agent is administered a period of time after a dose of anti-CD25 Antibody Agent as described herein. In some embodiments, one or more doses of the second agent is administered a period of time before a dose of an anti-CD25 Antibody Agent. In some embodiments, an anti-CD25 Antibody Agent as described herein can be also administered in regimens that involve not only subsequent administration by the same route but also by alternating administration routes such as by sub-cutaneous (or intramuscular) administration and intra-tumoral administration, within one or more cycles of treatments over one, two, four or more weeks, repeating such cycle with the same regimen (or by extending the interval between administrations), depending of patient responses. Also, in some embodiments, the precise regimen followed (e.g., number of doses, spacing of doses (e.g., relative to each other or to another event such as administration of another therapy), amount of doses, etc. may be different for one or more cycles as compared with one or more other cycles.

By using any of the routes of administrations, dosages, and/or regimens as described herein, an anti-CD25 Antibody Agent as described herein can be identified, characterized, and/or validated, for example, taking into account one or more criteria that are measured in the patients using biopsies, blood samples, and/or other clinical criteria. In some embodiments, as an alternative or in addition to direct evaluation of tumor size and/or metastasis, therapeutic efficacy of an anti-CD25 Antibody Agent as described herein can be determined in methods wherein one or more different general criteria are evaluated: decrease of regulatory T cells in circulation, tumours and/or in lymphoid organs, direct cytotoxicity on cancer cells (apoptosis and necrosis of cancer cells), increase of tumor infiltrating, immune cells (such as CD4-positive and/or CD8-positive tumor infiltrating T cells), increase in immune cells that circulates in blood (total populations or specific sub-populations of lymphocytes, NK cells, monocytes, dendritic cells, macrophages, B cells, etc.), and/or presenting some differential expression pre-versus post-treatment only in either responding or non-responding patients (as determined by RNA sequencing, mass flow cytometry, and/or other mass sequencing approach). Alternatively, or additionally, in some embodiments, such identification, characterization, and/or validation may involve the follow-up at molecular level by screening the mRNA and/or protein expression of one or more specific proteins or sets of proteins. In some embodiments, one or more such techniques may allow identification or relevant information for evaluating the response to an anti-CD25 Antibody Agent as described herein, for example that may be is related to tissue distribution and/or markers for specific cell populations within (or nearby) the tumor and/or circulating in blood.

Such approaches and immune-biological data may allow determination not only of one or more efficacy and/or safety parameters or characteristics, but in some embodiments, can provide a rationale for choosing a particular dose, route or dosing regimen, for example that may be utilized in one or more clinical trials for a given indication, alone and/or in combination with other drugs, standard-of-care protocols, or immunotherapies that can provide further therapeutic benefits. Thus, in a series of further embodiments of the invention, an anti-CD25 Antibody Agent as described herein is used in a method of treating a patient suffering from a disease (such as cancer) or preventing a disease (such as cancer) after determining the combined presence (and/or absence) of expression at RNA and/or protein level for one or more genes in cells or tissues of the patient (such as a tumor, a blood sample, or a blood fraction), post- or pre-treatment with such a formulation. Such methods may allow therefore defining a one or more biomarkers, or a more complex gene expression signature (or cell population distribution) that is associated to the therapeutically effective amount of a desirable anti-CD25 Antibody Agent, the therapeutically relevant biomarker(s) that predicts that a subject may have an anti-tumor or anti-infective response after the treatment with an anti-CD25 Antibody Agent as described herein, or the therapeutically relevant biomarker(s) that predicts that a subject may respond to the treatment with a compound after the treatment with an anti-CD25 Antibody Agent.

Alternatively, or additionally, in some embodiments, dosing and administration for a particular anti-CD25 Antibody Agent as disclosed herein can be preliminarily established and/or later evaluated in view of CD25 expression in human cancers and/or other human tissues, for example by gathering data about CD25 distribution in stromal and/or immune subsets in various cancers, tissues and/or patients. Such data can be generated by using common technologies (such as flow cytometry, mass cytometry, immunohistochemistry or mRNA expression libraries) across common cancer types and/or tissues (central nervous system, Esophagus, Stomach, Liver, Colon, Rectum, Lung, Bladder, Heart, Kidney, Thyroid, Pancreas, Uterus, Skin, Breast, Ovary, Prostate and testis) for identifying relationship between CD25 expression in various immune and non-immune subpopulations and/or its relation with cell infiltrate measures and/or cancer-relevant markers associated with sub-sets of cancer cells or immune cells (such as Foxp3 and PD-1/PD-L1). CD25 expression can be confined (or not) to immune subsets in tumor tissue (such as in NK cells and other effector or regulatory immune cells), and correlations between CD25 expression and immune checkpoint inhibitors can be determined if being positive, thus suggesting appropriate uses of anti-CD25 Antibody Agents in combinations with compounds targeting such immune checkpoint inhibitor, for example a PD-1 antagonist, such as an anti-PD-1 antibody or an anti-PD-L1 antibody.

Articles of Manufacture and Kits; In some embodiments of the invention, an anti-CD25 Antibody Agent as described herein is provided in a separate article of manufacture. In some embodiments of the invention, an article of manufacture containing an anti-CD25 Antibody Agent is provided in or with a container with a label. Suitable containers may include, for example, bottles, vials, syringes, and test tubes. In some embodiments, a container may be formed from any or a variety of materials such as glass or plastic. In some embodiments, a container holds a composition that is effective for treating a particular disease, disorder, or condition, or stage or type thereof. In some embodiments, a container may have a sterile access port (for example the container may be an intravenous solution bag or a vial having a stopper pierceable by a hypodermic injection needle). For example, in some embodiments, a composition comprising an anti-CD25 Antibody Agent as described herein is packaged in clear glass vials with a rubber stopper and an aluminium seal. The label on, or associated with, the container indicates that the composition is used for treating the condition of choice.

In some embodiments, an article of manufacture may further comprise a separate container comprising a pharmaceutically acceptable buffer, such as phosphate-buffered saline, Ringer's solution and dextrose solution and/or may further include other materials desirable from a commercial and user standpoint, including other buffers, diluents, filters, needles, syringes, and package inserts with instructions for use. For example, in some embodiments, an article of manufacture may allow providing each or the agent in an intravenous formulation as a sterile aqueous solution containing a total of 2 mg, 5 mg, 10 mg, 20 mg, 50 mg, or more that are formulated, with appropriate diluents and buffers, at a final concentration of 0.1 mg/ml, 1 mg/ml, 10 mg/ml, or at a higher concentration.

In some embodiments, an anti-CD25 Antibody Agent as described herein can be provided within the kits-of-parts in the form of lyophilized is to be reconstituted with any appropriate aqueous solution that provided or not with the kits, or other types of dosage unit using any compatible pharmaceutical carrier. One or more unit dosage forms of an anti-CD25 Antibody Agent may be provided in a pack or dispenser device. Such a pack or device may, for example, comprise metal or plastic foil, such as a blister pack. In order to use correctly such kits-of-parts, it may further comprise buffers, diluents, filters, needles, syringes, and package inserts with instructions for use in the treatment of cancer.

In some embodiments, instructions that are associated with an article of manufacture or the kits as described herein may be in the form of a label, a leaflet, a publication, a recording, a diagram, or any other means that can be used to inform about the correct use and/or monitoring of the possible effects of the agents, formulations, and other mate-

EXAMPLES

Example 1

Generation of Antibodies that Bind CD25 In Vitro

Materials and Methods
CD25 Antigen Preparation
Mouse CD25-HIS, human CD25-Fc and untagged recombinant proteins were purchased from R&D Systems Biotechne. Cynomolgus CD25-Fc and CD25-HIS recombinant proteins were purchased from Sino Biological. Protein reagent biotinylation was done using the EZ-Link Sulfo-NHS-Biotinylation Kit, Thermo Scientific, Cat #21425. The CD25 antigen was concentrated to ~1 mg/mL and buffer exchanged into PBS before addition of 1:7.5 molar ratio biotinylation reagent (EZ-Link Sulfo-NHS-Biotinylation Kit, Thermo Scientific, Cat #21425.). The mixture was held at 4° C. overnight prior to another buffer exchange to remove free biotin in the solution. Biotinylation was confirmed through Streptavidin sensor binding of the labeled proteins on a ForteBio.

Library Interrogation and Selection Methodology for Isolation of Anti-CD25 Antibodies:
Eight naïve human synthetic yeast libraries each of ~$10^9$ diversity were designed, generated, and propagated as described previously (see, e.g.: Xu et al, 2013; WO2009036379; WO2010105256; WO2012009568). Eight parallel selections were performed, using the eight naïve libraries for monomeric human CD25 selections.

For the first two rounds of selection, a magnetic bead sorting technique utilizing the Miltenyi MACs system was performed, essentially as described (Siegel et al. 2004). Briefly, yeast cells (~$10^{10}$ cells/library) were incubated with 3 ml of 10 nM biotinylated dimeric human CD25 antigen for 15 min at 30° C. in FACS wash buffer (PBS with 0.1% BSA). After washing once with 50 ml ice-cold wash buffer, the cell pellet was resuspended in 40 mL wash buffer, and 500 µl Streptavidin MicroBeads (Miltenyi Biotec, Bergisch Gladbach, Germany. Cat #130-048-101) were added to the yeast and incubated for 15 min at 4° C. Next, the yeast were pelleted, resuspended in 5 mL wash buffer, and loaded onto a MACS LS column (Miltenyi Biotec, Bergisch Gladbach, Germany. Cat.#130-042-401). After the 5 mL was loaded, the column was washed 3 times with 3 ml FACS wash buffer. The column was then removed from the magnetic field, and the yeast were eluted with 5 mL of growth media and then grown overnight.

Subsequent to the two rounds of MACS, four rounds of sorting were performed using flow cytometry (FACS), which are described in the following three paragraphs.

For the first round of FACS selections, approximately $4\times10^7$ yeast were pelleted, washed three times with wash buffer, and incubated with 10 nM of each the biotinylated dimeric human or 200 nM of biotinylated monomeric mouse CD25 antigen for 15 min at 30° C. Yeast were then washed twice and stained with goat anti-human F(ab')$_2$ kappa-FITC diluted 1:100 (Southern Biotech, Birmingham, Ala., Cat#2062-02) and either streptavidin-Alexa Fluor 633 (Life Technologies, Grand Island, N.Y., Cat # S21375) diluted 1:500, or Extravidin-phycoerthyrin (Sigma-Aldrich, St Louis, Cat # E4011) diluted 1:50, secondary reagents for 15 min at 4° C. After washing twice with ice-cold wash buffer, the cell pellets were resuspended in 0.4 mL wash buffer and transferred to strainer-capped sort tubes. Sorting was performed using a FACS ARIA sorter (BD Biosciences) and sort gates were determined to select only CD25 binding. The murine selected populations from the first round of FACS were combined into a pool. This pool was then sorted for human CD25 binding to increase or identify cross-reactive binders in the third round of FACS (described below).

The second and third round of FACS for the human selected populations involved positive sorts for CD25 binders or negative sorts to decrease reagent polyspecific binders (Xu et al., 2013). Depending on the amount of polyspecific binding or target binding of a specific selection output, a positive sort followed a negative sort or vice versa, to enrich for a full binding population with limited amount of polyspecific binding. A sample of the output from the round three selections was plated and sequenced.

The fourth round of FACS consisted predominantly of positive selection using 10 nM biotinylated dimeric cyno CD25 as antigen. A sample of these selections were then plated and sequenced, similar to that done with the round three selection output.

Affinity Maturation of Clones Identified in Naïve Selections
Heavy chains from the polyspecific binder negative sort outputs were used to prepare light chain diversification libraries used for four additional selection rounds. The first of these selection rounds utilized Miltenyi MACs beads conjugated with either 10 nM biotinylated dimeric human CD25 as antigen or 100 nM biotinylated monomeric murine CD25 as antigen.

Subsequent to the MACs bead selections, three rounds of FACS sorting were performed. The first of these rounds used either monomeric human CD25 at 100 nM, dimeric cyno CD25 at 10 nM, or monomeric murine CD25 at 200 nM. The second FACS round was a negative selection with the polyspecificity reagent to enrich for a full binding population with limited amount of polyspecific binding. The third FACS round included a titration of human CD25 antigen down to 1 nM as well as a parallel selection using 100 or 10 nM murine CD25.

In parallel to the third FACS round described in the immediately preceding paragraph, competition selections were performed. For the competition selections, 200 nM of competitor IgG (from naïve selection (described above) with known bins on human CD25 to select antibodies that either did or did not compete with that bin) was incubated with 10 nM biotinylated dimeric human CD25 for 30 minutes prior to incubation with yeast for 30 minutes.

Individual colonies from each FACS selection round described above were plated and picked for sequencing characterization.

IgG and Fab Production and Purification:
Yeast clones were grown to saturation and then induced for 48 h at 30° C. with shaking. After induction, yeast cells were pelleted and the supernatants were harvested for purification. IgGs were purified using a Protein A column and eluted with acetic acid, pH 2.0. Fab fragments were generated by papain digestion and purified over CaptureSelect IgG-CH1 affinity matrix (LifeTechnologies, Cat #1943200250).

Producing a-Fucosylated aCD25-a-674 Human IgG1 Expressed in Mammalian Cells:
Synthesis of codon optimized VH and VL coding sequences for the antibody was performed and cDNAs of variable regions were cloned into the antibody expression vector (Evitria, Switzerland) using conventional (non-PCR based) cloning techniques. cDNA for oxidoreductase GDP-6-deoxy-d-lyxo-4-hexulose reductase (RMD) enzyme was cloned into an expression vector (Evitria, Switzerland). Plasmid DNA was prepared under low-endotoxin conditions based on anion exchange chromatography. Evitria uses suspension-adapted CHO K1 cells (originally received from ATCC and adapted to serum-free growth in suspension culture at Evitria) for production. The seed was grown in eviGrow medium, a chemically defined, animal-component free, serum-free medium. Cells were transfected with expression vectors for the IgG1 and the RMD enzyme using eviFect, Evitria's custom-made, proprietary transfection reagent. Cells were grown after transfection in eviMake2, an animal-component free, serum-free medium. Supernatant was harvested by centrifugation and subsequent filtration (0.2 μm filter). The antibody was purified using MabSelect™ SuRe™. The glycosylation pattern of the antibodies was characterized using LC/MS and showed >99% of a-fucosylation.

Figure 5:
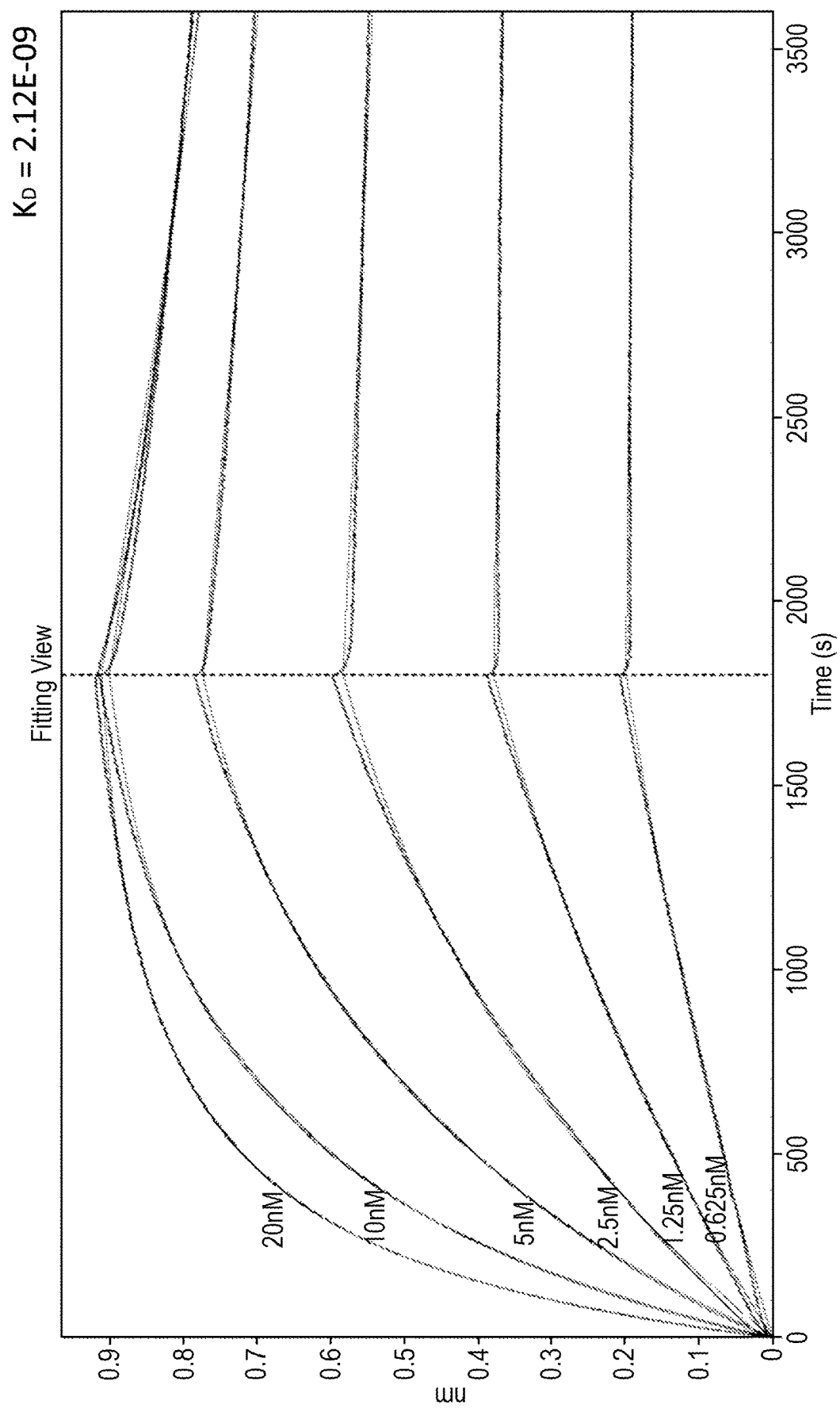
FIG. 5: Binding of aCD25-a-674 to recombinant human CD25 his tagged measured by biolayer interferometry on the Octet Red 96 instrument. 20.83 nM of rhCD25-his was loaded to the Ni NTA biosensor followed by varying concentrations of antibody (as shown in the Figures) and then let them to dissociate in Kinetics Buffer.
Figure 7:
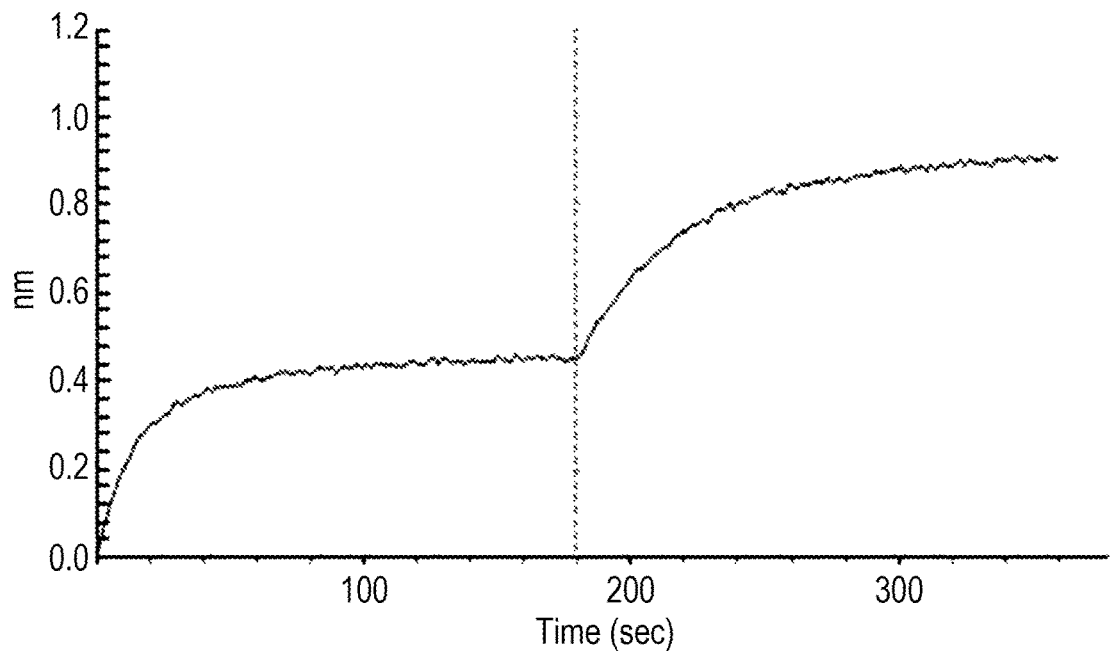
FIG. 7: Shows non-competitive binding of aCD25-a-674 and Daclizumab to CD25 by biolayer interferometry on the Octet Red384 system using a standard sandwich format binning assay. The reference monoclonal anti-human CD25 antibody Daclizumab was loaded onto AHQ sensors. The sensors were then exposed to 100 nM human CD25 antigen followed by the anti-human CD25 antibody (aCD25-a-674). Additional binding by the second antibody after antigen association indicates an unoccupied epitope (non-competitor), while no binding indicates epitope blocking (competitor).

Affinity Measurements of Anti-CD25 Antibodies:

The affinity for the CD25 antibodies was determined by measuring their Kd by ForteBio. ForteBio affinity measurements were performed generally as previously described (Estep et al., 2013). Briefly, ForteBio affinity measurements were performed by loading IgGs on-line onto AHQ sensors. Sensors were equilibrated off-line in assay buffer for 30 min and then monitored on-line for 60 seconds for baseline establishment. Monovalent binding measurements were obtained by loading CD25 dimer on AHC sensors followed by exposure to 100 nM antibody Fab in solution. For avidity binding measurement, Ni-NTA sensors were loaded with 20.83 nM antigen (recombinant human CD25 HIS tagged) for 5 min, afterwards they were transferred to assay buffer for 0.5 min for wash and again for 1 min in assay buffer for base line determination. Then the antibody was associated at different concentrations (see FIG. 5) for 20 min. Afterwards they were transferred to assay buffer for 26.6 min for off-rate measurement. Kinetics data were fit using a 1:1 binding model in the data analysis software provided by ForteBio.

Ligand Binding:

Ligand binding of the antibodies was performed on a Forte Bio Octet Red384 system (Pall Forte Bio Corp., USA) using a standard sandwich binning assay. The anti-human CD25 antibody (aCD25-a-674) was loaded onto AHQ sensors and unoccupied Fc-binding sites on the sensor were blocked with a non-relevant human IgG1 antibody. Sensors were exposed to 100 nM human CD25 followed by 100 nM human IL-2. Data was processed using Forte Bio Data Analysis Software 7.0. Additional binding by human IL2 after antigen association indicates an unoccupied epitope (non-competitor), while no binding indicates epitope blocking (competitor).

Epitope Binning:

Epitope binning of the antibodies was performed on a Forte Bio Octet Red384 system (Pall Forte Bio Corporation, Menlo Park, Calif.) using a standard sandwich format binning assay. Anti-human CD25 antibody IgG were loaded onto AHQ sensors and unoccupied Fc-binding sites on the sensor were blocked with a non-relevant human IgG1 antibody. The sensors were then exposed to 100 nM target antigen followed by daclizumab or basiliximab. Data was processed using ForteBio's Data Analysis Software 7.0. Additional binding by the second antibody after antigen association indicates an unoccupied epitope (non-competitor), while no binding indicates epitope blocking (competitor).

Binding of Anti-CD25 Antibodies to CD25-Expressing Cells:

The candidate hits are evaluated by binding to lymphoma human cell lines, SU-DHL-1 and SR-786, Karpas299, in-vitro differentiated Tregs cells, and the HSC-F Cynomolgus monkey T cell line. Binding to CD25 expressing human cell lines (SU-DHL-1 and SR-786) was examined by firstly blocking the cells with Trustain (Biolegend) prior to incubation with anti-CD25 antibodies titrated in a semi-log dilution series from a top concentration of 20 μg/ml, for 30 mins at 4° C. before being washed and incubated with PE conjugated anti-human IgG Fc antibody (Biolegend). Cells were washed again and resuspended in FACS buffer containing DAPI and acquired on the Intellicyt iQue. Live cells were gated using FSC vs SSC parameters by flow cytometry during sample acquisition. Geo Mean Intensity of stained cells were plotted on an XY chart, graphing Geo Mean Intensity against the log of the concentration, and the data fit to a non-linear regression curve from which the EC50 is calculated.

Binding to CD25 expressing in vitro differentiated Tregs was examined by staining test articles (anti-CD25 primary antibodies) with 30 μg/ml antibodies followed by semi-log dilution series (7-point) for 30 minutes on ice. This was followed by staining with a secondary antibody (Alexa Fluor 647-AffiniPure Fab Fragment Goat Anti-Human IgG (H+L)—(Jackson ImmunoResearch)) concentration of 1 μg/ml for 30 minutes on ice. All samples were stained in duplicates. Live cells were gated using FSC vs SSC parameters by flow cytometry during sample acquisition. Mean fluorescence intensity (MFI) of stained cells were plotted on an XY chart, graphing MFI against the log of the concentration, and the data fit to a non-linear regression curve from which the EC50 is calculated.

Binding to CD25 expressing activated human and Cynomolgus monkey PMBC was examined by staining test articles (anti-CD25 primary antibodies) with 20 μg/ml antibodies followed by semi-log dilution series (7-point) for 30 minutes on ice. This was followed by staining with a secondary antibody (rabbit anti-human Fcg F(ab')2-(Jackson ImmunoResearch)) concentration of 5 μg/ml for 30 minutes on ice. All samples were stained in triplicates. To minimize cross-linking induced cell death mediated by binding of the secondary antibody, cell lines were examined in staining cohorts of 4 test articles at a time. Live lymphocytes were gated using FSC vs SSC parameters by flow cytometry during sample acquisition. Mean fluorescence intensity (MFI) of gated $CD4^+$ and $CD8^+$ T cell subsets were plotted on an XY chart, graphing MFI against the log of the concentration, and the data fit to a non-linear regression curve from which the EC50 was calculated.

Binding to CD25 expressing Karpas299 cells is examined by staining test articles (anti-CD25 primary antibodies) with 20 μg/ml antibodies followed by semi-log dilution series (7-point) for 30 minutes on ice. This is followed by staining with a secondary antibody (Alexa Fluor 647-AffiniPure F(ab')2 Fragment Rabbit Anti-Human IgG Fcγ fragment—(Jackson ImmunoResearch)) concentration of 1 μg/ml for 30 minutes on ice. All samples are stained in duplicates. Live cells are gated using FSC vs SSC parameters by flow cytometry during sample acquisition. Mean fluorescence intensity (MFI) of stained cells are plotted on an XY chart, graphing MFI against the log of the concentration, and the data fit to a non-linear regression curve from which the EC50 is calculated.

Recloning, Producing, and Characterizing of aCD25-a-674 as Human IgG1 Expressed in Mammalian Cells:

Synthesis of codon optimized VH and VL coding sequences for the antibody was performed by Genewiz. cDNAs of variable regions were cloned into the antibody expression vector (Icosagen, EST) containing human IgG1 heavy chain and kappa light chain constant regions (P01857 and P01834 respectively). Full length heavy and light chain cDNAs were verified by sequencing in final vectors and then recloned for expressing them using the QMCF Technology (Icosagen) a stable episomal expression system that uses CHO-based cells (CHOEBNALT85) and appropriate vectors for production of recombinant proteins, antibodies, CHOEBNALT85 cells were transfected with 1 μg of the expression plasmids for antibody production. 48 h after the transfection 700 μg/ml of G418 was added to select plasmid containing cell population. For the production, temperature was shifted to 30° C. and the cultures were additionally fed. At the end of the production the culture supernatants were clarified by centrifugation (1000 g, 30 min, and 15° C.), PMSF was added and supernatants were processed or frozen until purification. hIgG1 antibodies were purified by MabSelect SuRe affinity chromatography followed by Superdex 200 gel filtration into either PBS or PBS 100 mM L-Arg. Human IgG1 antibodies produced in CHOEBNALT85 cells were characterized for affinity towards recombinant human CD25, cross reactivity towards murine, and cyno CD25 and epitope binning versus the selected CD25 binding antibodies.

aCD25-a-674 Epitope Mapping:

Different sets of linear, single loop, β-turn mimics, disulfide bridge mimics, discontinuous disulfide bridges, discontinuous epitope mimics peptides representing the human CD25 sequence (Uniprot record no. P01589) were synthesized using solid-phase Fmoc synthesis (Pepscan BV, The Netherlands; Timmermann P et al., 2007; Langedijk J P et al., 2011). The binding of the a-674 antibody to each of the synthesized peptides was tested in an ELISA (Pepscan, The Netherlands). The peptide arrays were incubated with primary antibody solution (overnight at 4° C.). After washing, the peptide arrays were incubated with a 1/1000 dilution of an appropriate antibody peroxidase conjugate (2010-05; Southern Biotech) for one hour at 25° C. After washing, the peroxidase substrate 2,2'-azino-di-3-ethylbenzthiazoline sulfonate (ABTS) and 20 μl/ml of 3 percent H2O2 were added. After one hour, the colour development was measured. The colour development was quantified with a charge coupled device (CCD)—camera and an image processing system. The values obtained from the CCD camera range from 0 to 3000 mAU, similar to a standard 96-well plate ELISA-reader. To verify the quality of the synthesized peptides, a separate set of positive and negative control peptides was synthesized in parallel and screened with irrelevant, control antibodies The Anti Human CD25 Ab Competition Assays:

Antibody competitions are performed on a Forte Bio Octet Red96 system (Pall Forte Bio Corp., USA) using a standard sequential binding assay. 26.8 nM recombinant human CD25his tagged is loaded onto Ni-NTA Biosensors for 200 s. After base line step on kinetic buffer sensors were exposed to 66.6 nM of first antibody for either 600 s followed by a second anti-CD25 antibody (also at 66.6 nM for either 600 s). Data is processed using Forte Bio Data Analysis Software 9.0. Additional binding by a second antibody indicates an unoccupied epitope (no competition for the epitope), while no binding indicates epitope blocking (competition for the epitope).

Results

Monoclonal antibodies (mAb) binding to recombinant human CD25 extracellular protein sequence (rhCD25) were isolated using a yeast-based antibody presentation library as described in the Materials & Methods. These antibodies were sequenced, and unique clones were produced in yeast cells (Barnard G C et al., 2010). The cell culture supernatants for each yeast clone expressing a unique antibody sequence were screened for rhCD25 binding.

Based on the binding to rhCD25, sequence uniqueness and expression levels, a panel of mAbs were identified. These antibodies were further characterized for binding to recombinant Cynomolgus monkey and mouse CD25 extracellular domain protein sequences. The clones were characterized showing IgG binding values to monovalent rhCD25 and/or recombinant cyno CD25 extracellular protein sequences that are comprised between $10^{-8}$ M and $10^{-10}$ M. In addition, each antibody was characterized as competing or not with the IL-2 ligand or reference anti-CD25 antibody Daclizumab. The antibody clones were also evaluated at the level of binding to human cells expressing different levels of CD25, such as the lymphoma cell line, SU-DHL-1, and in-vitro differentiated Treg cells, by flow cytometry.

The results of the binding to rhCD25, cross binning and IL-2 competitive binding analysis are shown in Table 1 (FIG. 3-7).

TABLE 1

| Antibody | Binding to human and cyno CD25 expressing cells | Epitope cross-binning group | Competitor of IL-2 binding to CD25 | ForteBio IgG Kd Human CD25-His (M) Avidity |
|---|---|---|---|---|
| aCD25-a-674 | Yes | 3 | No | 2.12E–09 |
| Daclizumab | Yes | 1 | Yes | 6.00E–10 |

Binding of Anti-CD25 Antibodies is Shown in FIGS. 3-7.

Finally, in order to eliminate antibody sequences that would be prone to aggregation and non-specific interaction, the antibodies were screened in a Poly Specific Reagent (PSR) assay and Affinity-Capture Self-Interaction Nanoparticle Spectroscopy (AC-SINS), an approach that allows high-throughput screening for early-stage antibody development (Liu Y et al., 2014). None of the selected antibodies scored positive in the latter assays and as such were not removed from the panel.

Among the selected hits that were sequenced and characterized as described above, the clone aCD25-a-674 is an antibody presenting novel complementarity determining regions (CDRs; FIG. 1) that compete for human CD25 binding neither with Daclizumab nor with Basiliximab. The epitope mapping study that has been performed using Pepscan technology would indicate that aCD25-a-674 binds human CD25 in the region from amino acids 150-158 and 176-186 (FIG. 2) and binds human CD25 extracellular protein sequences with a Kd value in the $10^{-8}$M to $10^{-10}$ M range.

CD25 Kinetic Measurement—Binding Strength Using Affinity and/or Avidity

The following additional investigations relating to affinity and avidity were performed. Binding of CD25 antibodies to human CD25 antigen was investigated by surface plasmon resonance using a BIACORE T200 instrument (GE Healthcare). Around 8000 resonance units (RU) of the capturing system (20 μg/ml anti human Fab; order code of Human Fab Capture Kit: 28-9583-25; GE Healthcare) were coupled on a CM5 chip (GE Healthcare BR-1005-30) at pH 5.0 by using an Amine Coupling Kit supplied by GE Healthcare (BR-1000-50).

Running and dilution buffer was PBS-P pH 7.4 (20 mM phosphate buffer, 2.7 mM KCl, 137 mM NaCl, 0.05% Surfactant P20; GE Healthcare, order code 28-9950-84). The flow cell was set to 25° C. and the sample compartment to 12° C. The CD25 antibody was captured by injecting a 3 µg/ml solution for 60 sec at a flow rate of 10 µl/min. Association of CD25 antigen was measured by injection of human CD25 solutions for 180 sec at a flow rate of 30 µl/min starting with a concentration of 1000 nM down to 1 nM in 1:10 dilution steps. The dissociation phase was triggered by switching from sample solution injection to running buffer and monitored for up to 600 seconds. The surface was regenerated by washing with two consecutive 1-minute injections of 10 mM glycine pH 2.1 (provided by the kit) at a flow rate of 10 µl/min. Bulk refractive index differences were corrected by subtracting the response obtained from an anti-human Fab reference surface; blank injections are also subtracted (=double referencing).

Binding properties of CD25-antibodies were evaluated by using various CD25 antigen variants, i.e. inhouse produced monomeric antigen (P1AA5872) and two commercially available CD25 antigens (Sino Biologicals cat no. 10165-H08H; R&D Systems cat no. 223-2A/CF).

For calculation of KD and kinetic parameters Biacore provided fitting models were used to obtain optimal curve fitting results. The 1:1 Langmuir fit was used for P1AA5872 and the Two State Kinetic fitting for CD25 from Sino Biologicals and R&D Systems.

TABLE 2

| CD25 form | Binding strength | Fit model |
|---|---|---|
| Sino biological (~20% dimer) | 40 nM | Two State Reaction |
| R&D Systems (~10% dimer) | 48 nM | Two State Reaction |
| Inhouse (0% dimer) | 517 nM | 1:1 Langmuir |

Thus, the aCD25-a-674 sequences (FIG. 1) identify antibodies that specifically bind CD25, and whose activities associated to the functional features defining anti-CD25 Antibody Agents, as that term is used herein, can be functionally evaluated by cell-based assays or animal models.

Example 2

Cell-Based Models for Validating CD25 Modulating Antibody Agents

Materials & Methods
In-Vitro IL-2 Signalling by STAT5 Phosphorylation Assay:
IL-2-blocking was characterised using a STAT5 phosphorylation assay, in which IL-2 signalling was examined. Previously frozen PBMC (Stemcell Technologies) were cultured in 96-U-bottom well plates in the presence of 10 µg/ml anti-CD25 antibodies for 30 minutes before adding IL-2 (Peprotech) at varying concentrations of 0.25 U/ml, 0.74 U/ml, 2.22 U/ml, 6.66 U/ml or 20 U/ml for 10 minutes in RPMI 1640 (Life Technologies) containing 10% FBS (Sigma), 2 mM L-Glutamine (Life Technologies) and 10,000 U/ml Pen-Strep (Sigma). IL-2 induced STAT5 phosphorylation was stopped when the cells were fixed and permeabilized with the eBioscience™ Foxp3/Transcription Factor Staining Buffer Set (Invitrogen) and treated with the BD Phosflow Perm Buffer III (BD Biosciences). Cells were then simultaneously stained with surface and intracellular fluorochrome labelled antibodies (STAT5-Alexa Fluor 647 clone 47/stat5/pY694 BD Bioscience, CD3-PerCP-Cy5.5 clone UCHT1 Biolegend, CD4-BV510 clone SK3 BD Bioscience, CD8-Alexa Fluor 700 clone RPA-T8 Invitrogen, CD45RA-PE-Cy7 clone HI100 Invitrogen, FoxP3-Alexa Fluor 488 clone 236A/E7 Invitrogen) and samples were acquired on the Fortessa LSR X20 Flow Cytometer (BD Bioscience) and analysed using the BD FACSDIVA software. Doublets were excluded using FCS-H versus FCS-A, and lymphocytes defined using SSC-A versus FCS-A parameters. $CD3^+$ T cells were defined using a CD3 PerCP-Cy5.5-A versus FCS-A plot and a gate was drawn on a histogram showing count versus STAT5 Alexa Fluor 647-A to determine the population of $STAT5^+$ $CD3^+$ T cells. The percentage blocking of IL-2 signalling was calculated as follows: % blocking=100×[(% $Stat5^+$ cells No Ab group—% $Stat5^+$ cells 10 ug/ml Ab group)/(% $Stat5^+$ cells No Ab group)]. Further analysis of STAT5 phosphorylation by different T cell subsets ($CD4^+$, $CD8^+$, $CD4^+$ $FoxP3^+$, naïve and memory T cells) was also be assessed by gating on the respective subsets and analyzed as above. Graphs and statistical analysis was performed using GraphPad Prism v7 (results not shown).

In-Vitro T Cell Activation Assay:
Impact of IL-2 signalling on Teff responses were characterised in a T cell activation assay, in which intracellular granzyme B (GrB) upregulation and proliferation were examined. Previously frozen primary human Pan T cells (Stemcell Technologies) were labelled with eFluor450 cell proliferation dye (Invitrogen) according to manufacturer's recommendation, and added to 96-U-bottom well plates at $1 \times 10^5$ cells/well in RPMI 1640 (Life Technologies) containing 10% FBS (Sigma), 2 mM L-Glutamine (Life Technologies) and 10,000 U/ml Pen-Strep (Sigma). The cells were then treated with 10 µg/ml anti-CD25 antibodies or control antibodies followed by Human T-Activator CD3/CD28 (20:1 cell to bead ratio; Gibco) and incubated for 72 hrs in a 37° C., 5% $CO_2$ humidified incubator. To assess T cell activation, cells were stained with the eBioscience Fixable Viability Dye efluor780 (Invitrogen), followed by fluorochrome labelled antibodies for surface T cell markers (CD3-PerCP-Cy5.5 clone UCHT1 Biolegend, CD4-BV510 clone SK3 BD Bioscience, CD8-Alexa Fluor 700 clone RPA-T8 Invitrogen, CD45RA-PE-Cy7 clone HI100 Invitrogen, CD25-BUV737 clone 2A3 BD Bioscience) and then fixed and permeabilized with the eBioscience™ Foxp3/Transcription Factor Staining Buffer Set (Invitrogen) before staining for intracellular GrB and intranuclear FoxP3 (Granzyme B-PE clone GB11 BD Bioscience, FoxP3-APC clone 236A/E7). Samples were acquired on the Fortessa LSR X20 Flow Cytometer (BD Bioscience) and analysed using the BD FACSDIVA software. Doublets were excluded using FCS-H versus FCS-A, and lymphocytes defined using SSC-A versus FCS-A parameters. $CD4^+$ and $CD8^+$ T cell subsets gated from the live $CD3^+$ lymphocytes were assessed using a GrB-PE-A versus proliferation eFluor450-A plot. Results were presented as percentage of proliferating GrB positive cells from the whole $CD4^+$ or $CD8^+$ T cell populations.

In Vitro ADCC Assay:
Antibody-dependent cell-mediated cytotoxicity assays (ADCC assays) were performed for the characterization of anti-human CD25 antibodies using SU-DHL-1, or SR-786 (CD25 positive) human cell lines as target cells with human NK cells as the source of effector cells. NK cells were isolated from PBMCs of healthy donors using NK cell negative isolation kit (Stemcell Technologies). NK cells were cultured overnight in the presence of and 2 ng/mL IL-2 (Peprotech). SU-DHL-1, or SR-786 target cells were loaded with Calcein-AM (Thermofisher) and plated, 4 replicates per condition, in the presence of anti-CD25 or isotype antibodies for 30 mins at 37° C. 5% $CO_2$. Following incubation, NK cells were added to wells at a Target:Effector (T:E) ratio of 1:10 (10,000 target cells and 100,000 effector cells) and incubated for 4 hrs at 37° C. 5% $CO_2$. Readout of calcein fluorescence in the supernatant was performed on BMG Fluostar plate reader. The percentage of specific lysis was calculated relative to target cells alone (0% lysis) and target cells treated with 0.1% Saponin (100% lysis). Graphs of the raw data were produced using Graphpad Prism v7 to generate dose response curves. Percentage target cell lysis was plotted on an XY chart, graphing normalized Calcein AM percentage release against the log of the concentration, and the data fit to a no-linear regression curve from which the EC50 was calculated.

In Vitro ADCP Assay:

Antibody-dependent cell-mediated phagocytosis (ADCP) assays were performed using in-vitro differentiated Tregs as target cells and monocyte-derived macrophages as the effector cells. PBMCs were isolated from leucocyte cones by Ficoll gradient centrifugation. Monocytes (CD14+ cells) were isolated using CD14 Microbeads (Miltenyi Biotec). Monocytes were cultured for 5 days in the presence of 50 ng/ml M-CSF in RPMI 1640 (Life Technologies) containing 10% FBS (Sigma), 2 mM L-Glutamine (Life Technologies) and 10,000 U/ml Pen-Strep (Sigma), fresh media containing M-CSF is added after 3 days. Regulatory T cells (Treg) were isolated using the Human Treg Cell Differentiation Kit (R&D Systems). These cells were incubated in a 37° C., 5% $CO_2$ humidified incubator for 5 days and labelled with eFluor450-dye (Invitrogen), as per manufacturer recommendations. At day 5, macrophages and eFluor450-dye labelled Tregs are cocultured for 4 hours at a 10 to 1 effector to target ratio in the presence of anti-CD25 antibodies or controls, as describe thereafter. Target cells (Treg) were added at $1 \times 10^4$ cells/well while the effector cells (macrophages) were added at $1 \times 10^5$ cells/well, for an effector to target ratio of 10 to 1. The anti-CD25 antibodies were then added at a top concentration of 1 µg/ml followed by a log series (7 points) in duplicates. Cells and antibodies were incubated for 4 hours at 37° C. 5% $CO_2$. To assess ADCP, cells were placed on ice, stained with the cell surface marker CD14 (CD14-PerCP-Cy5.5 clone MfP9 BD Biosciences) and fixed with the eBioscience fixation buffer. Two colour flow cytometric analysis was performed using the Fortessa LSR X20. Residual target cells were defined as cells that were eFluor450-dye+/CD14−. Macrophages were defined as CD14+. Dual-labelled cells (eFluor450-dye+/CD14+) were considered to represent phagocytosis of targets by Macrophages. Phagocytosis of target cells was calculated with the following equation: % Phagocytosis=100×[(percent dual positive)/(percent dual positive+percent residual targets)].

Statistics:

Prism software (GraphPad) was used to perform curve fitting to determine EC50 values and maximal activity.

Results

Figure 8:
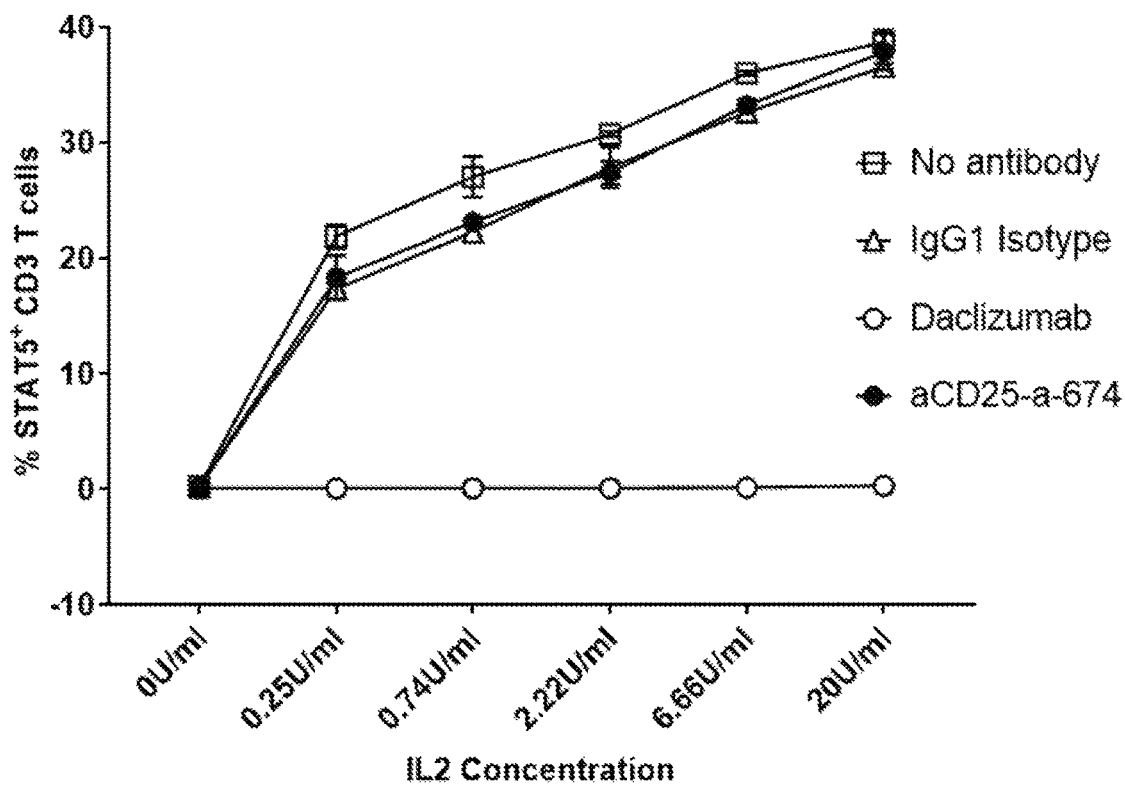
FIG. 8: Characterization of aCD25-a-674 compared to human IgG1 isotype control, Daclizumab, or in absence of a primary antibody in respect to blocking IL-2 signalling in a STAT5 phosphorylation assay using PBMCs of human origin. Cells were incubated with 10 µg/ml antibody followed by increasing concentrations of IL-2 (as shown in the Figures). Analysis was restricted to percentage of CD3-positive cells phosphorylating STAT5.
Figure 10:
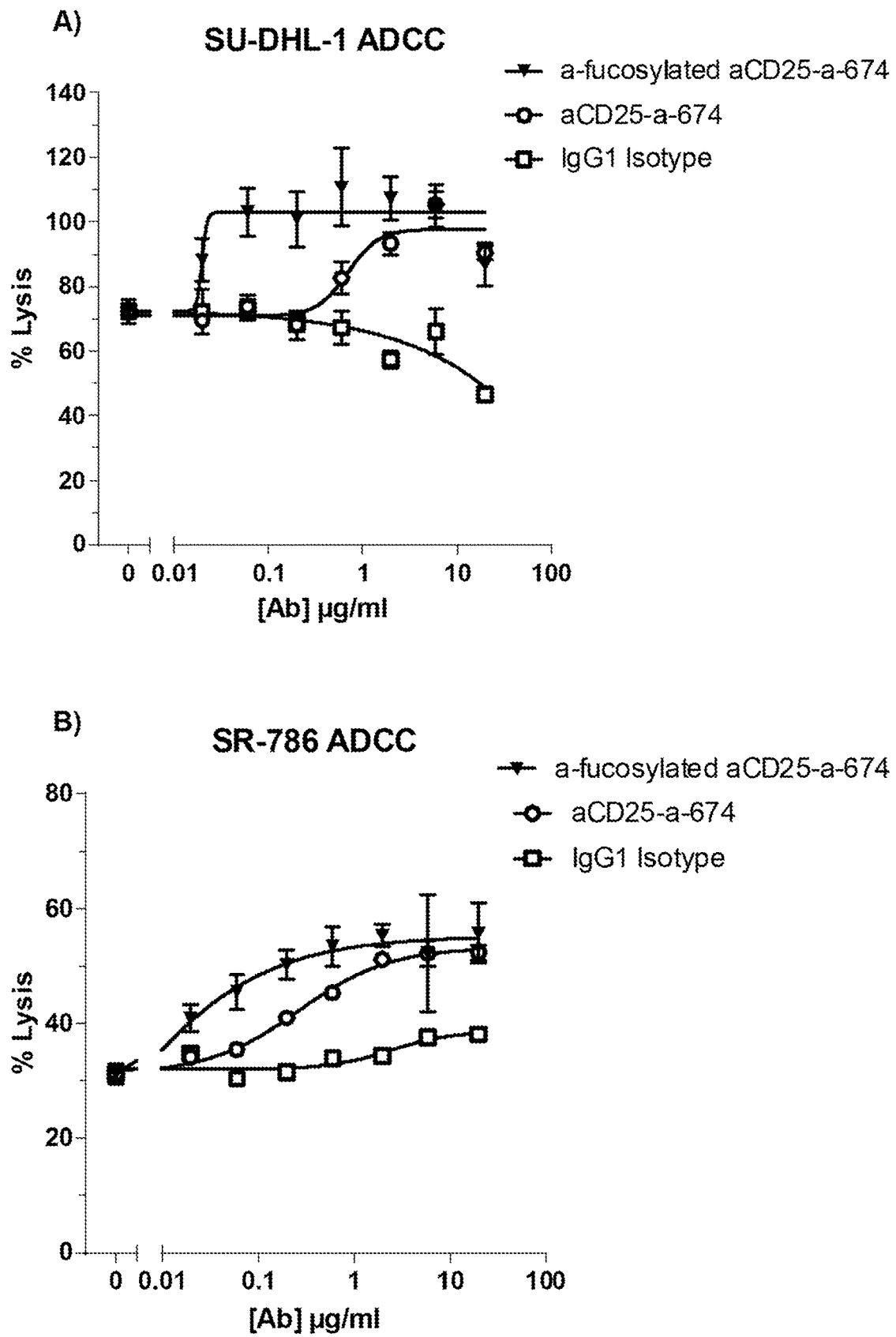
FIG. 10: Functional characterization of a-fucosylated aCD25-a-674 compared to the unmodified aCD25-a-674 and human IgG1 isotype control in respect to killing of CD25-positive cell lines in an ADCC assay. CD25-high or -low expressing cells, SU-DHL-1 (A) or SR-786 cells (B) respectively, were co-cultured with purified NK cells in the presence of varying concentrations of antibodies (as shown in the Figures). Target cell lysis was measured by calcein release into the supernatant at four hours post addition to NK cells. Data was normalised to saponin treated controls.
Figure 11:
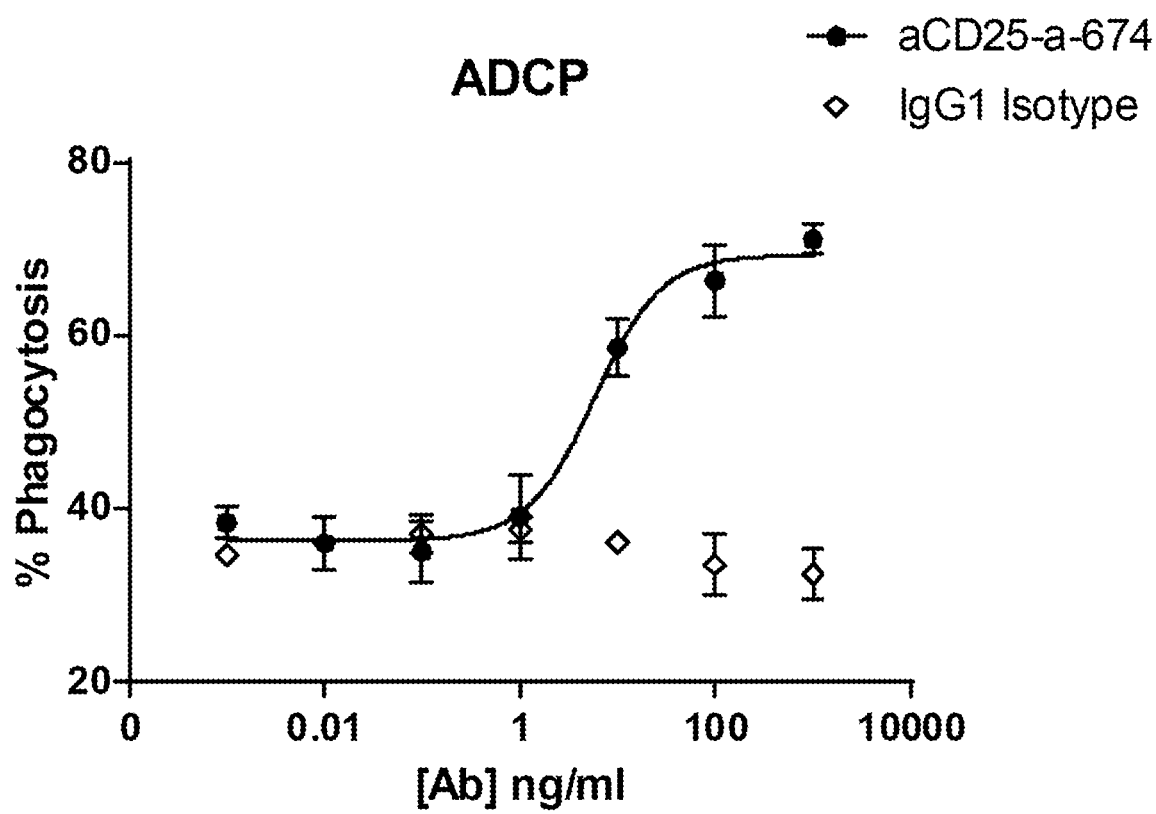
FIG. 11: Functional characterization of aCD25-a-674 compared to human IgG1 isotype control in respect to phagocytosis of in-vitro differentiated Treg cells in an ADCP assay. Tregs were co-cultured with MCSF differentiated Macrophages in the presence of varying concentrations of antibodies (as shown in the Figures). Two colour flow cytometric analysis was performed with CD14+ stained Macrophages and eFluor450-dye labelled Tregs. Residual target cells were defined as cells that were eFluor450-dye+/CD14−. Dual-labelled cells (eFluor450-dye+/CD14+) were considered to represent phagocytosis of targets by Macrophages. Phagocytosis of target cells was calculated with the following equation: % Phagocytosis=100×[(percent dual positive)/(percent dual positive+percent residual targets)].

The aCD25-a-674 antibody, as other CD25 antibodies that have been identified and characterized in Example 1, was further evaluated with respect to its ability to not interfere with IL-2 signalling and its capacity to kill CD25 expressing target cells. The ligand binding assay using the Octet showed that aCD25-a-674 does not affect IL-2 binding to CD25 (FIG. 6). This was confirmed in the STAT5 assay where aCD25-a-674 did not block IL-2 signalling regardless of IL-2 concentrations tested while IL-2 signalling was completely blocked by the reference antibody Daclizumab (FIG. 8). Daclizumab, which has been shown to block the interaction of CD25 with IL-2 via the so-called "Tac" epitope (Queen C et al, 1989 and Bielekova B, 2013) binds to a different epitope than aCD25-a-674 (FIG. 7), which can explain why Daclizumab blocks IL-2 signalling and the aCD25-a-674 does not block the IL-2 signalling in the STAT5 phosphorylation assay (FIG. 8). Finally, aCD25-a-674 kills CD25 expressing cells, tumor cells or regulatory T cells, via ADCC (FIG. 9) and ADCP (FIG. 11) when compared to the IgG1 isotype antibody. The a-fucosylated aCD25-a-674 antibody further increases the killing of CD25 positive cells compared to the unmodified CD25 antibody via ADCC (FIG. 10).

In conclusion, aCD25-a-674 has been characterized and demonstrates potent killing of CD25 positive cells (Tregs or cancer cell lines) and does not interfere with IL-2 signalling and consequently does not inhibit T effector responses. aCD25-a-674 is thus a Treg depleting antibody which could be applied for the treatment of cancer, as monotherapy or in combination.

Example 3

Production of Variants of CD25 Modulating Antibody Agents aCD25-a-634 can be subjected to further affinity maturation. The optimization is performed by introducing diversities into the heavy chain variable regions. The CDRH3 of the antibody is recombined into a premade library with CDRH1 and CDRH2 variants of a diversity of $1 \times 10^8$ and selections are performed with one round of MACS and four rounds of FACS as described in the naïve discovery. In the FACS rounds the libraries are looked at for PSR binding, species cross-reactivity, antigen cross-reactivity and affinity pressure, and sorting is performed in order to obtain a population with the desired characteristics. For these selections affinity pressures are applied either by titrating down biotinylated monomeric antigen or by preincubating the biotinylated antigen with parental Fab or IgG for 30 min and then applying that precomplexed mixture to the yeast library for a length of time which would allow the selection to reach an equilibrium. The higher affinity antibodies are then able to be sorted.

Variants showing the best affinities are then selected for mammalian production and can be further characterised using the assays as described above in Examples 1 and 2.

Example 4

Mouse Model Experiment

Materials and Methods

Therapeutic activity of a non-IL-2 blocking antibody: female BALB/c mice obtained from Charles River were injected with $3 \times 10^5$ CT26 tumour cells in 0% Matrigel subcutaneously in the flank, n=15 per group. Animals were randomized into treatment groups based on Day 1 bodyweight. Treatment was started on Day 6 and mice were treated with one injection of each antibody (mouse IgG2a isotype, IL-2 neutralizing antibody, PC61 mIgG1, a anti-mouse CD25 blocking IL-2 signalling of mouse IgG1 isotype, and 7D4 mIgG2a, an anti-mouse CD25 non-blocking IL-2 signalling of mouse IgG2a isotype) at 200 µg/animal.

Animals received either monotherapy treatments, with one group per antibody, or combination treatment of 7D4 mIgG2a and the IL-2 neutralizing antibody or 7D4 mIgG2a and PC61 mIgG1 antibody. Mice were sacrificed when the tumour volume reached 2000 mm3 or 50 days, whichever was reached first.

Results

Figure 12:
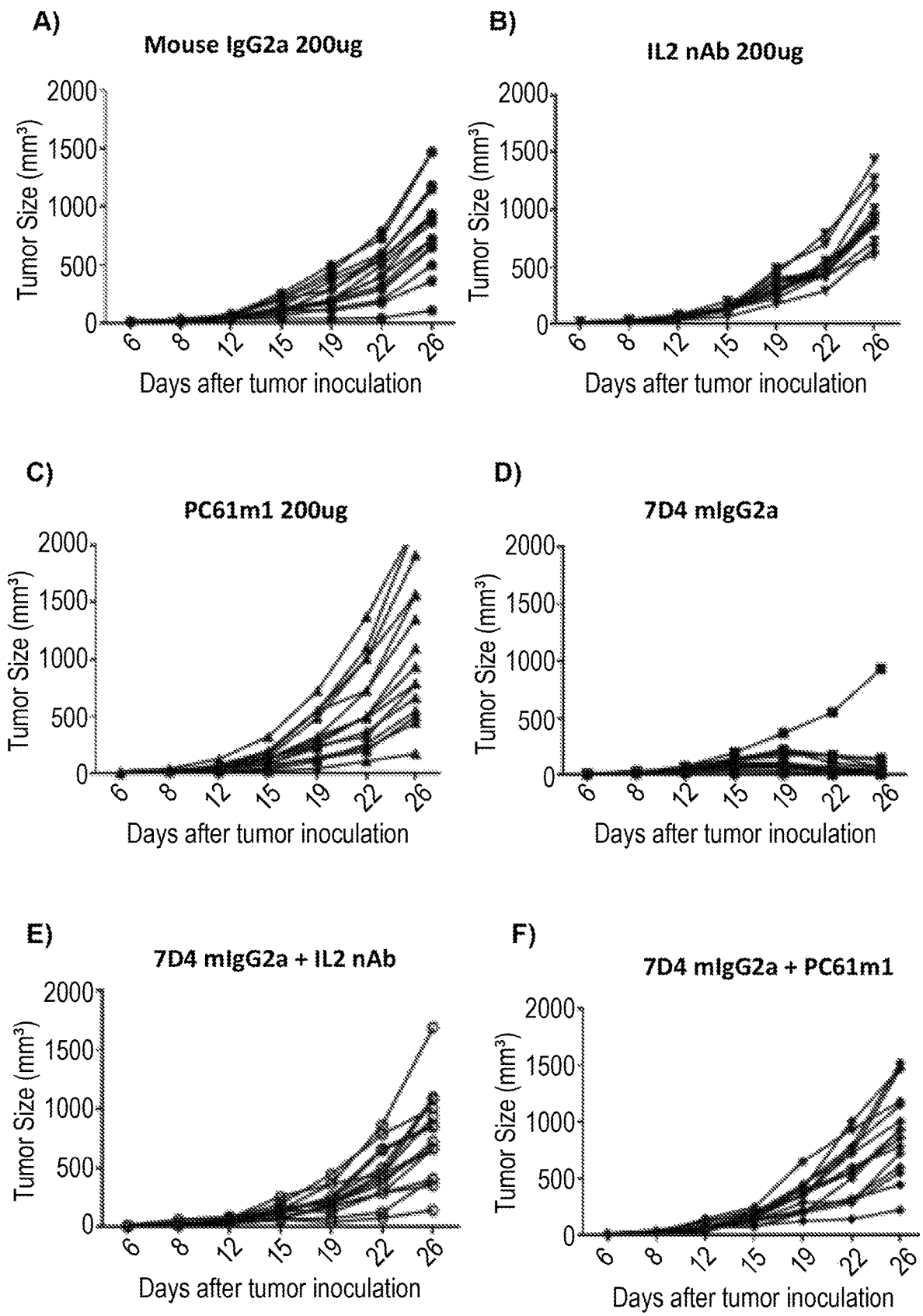
FIG. 12: Evaluation of the therapeutic activity of 7D4 mIgG2a, an anti-mouse CD25 non-IL-2 blocking, Treg depleting antibody alone (D) and in combination with an IL-2 neutralizing antibody (E) or an IL-2 blocking antibody (F) in mice bearing CT26 syngeneic colon tumors in female BALB/c mice. The activity of mouse IgG2a control (A), an IL-2 neutralizing antibody alone (B) and an IL-2 blocking antibody alone (C) were tested for comparison.

The anti-CD25 depleting non-IL-2 blocking antibody 7D4 mIgG2a induced tumour rejection in treated mice, while the other antibodies showed no effect as monotherapy when compared to the isotype control mouse IgG2a. Combination with IL2-blocking antibodies, either PC61 mIgG1 or IL2 nAb, abrogates the therapeutic activity of the non-IL-2 blocking antibody 7D4 mIgG2a (FIG. 12). This demonstrates that the non-IL-2 blocking feature of 7D4 mIgG2a is key for therapeutic activity. It also suggests that the therapeutic activity of this antibody relies on anti-tumor immune response mediated by T effector cells, which are dependent on IL-2 signalling for optimal activity. These results show that the absence of IL-2/CD25 blocking activity is required for an optimal therapeutic activity of the CD25 targeting antibody and supports the use of an anti-CD25 non-IL-2 blocking antibody as described herein in cancer therapy.

Sequences

A summary of the sequences included in the application is provided below:

| SEQ ID NO | Description of Antibody Sequences | Also referred to as: |
|---|---|---|
| 1 | Human CD25 | Uniprot code P01589 |
| 2 | aCD25-a-674 variable heavy chain CDR1 | CD25-a-674-HCDR1 |
| 3 | aCD25-a-674 variable heavy chain CDR2 | aCD25-a-674-HCDR2 |
| 4 | aCD25-a-674 variable heavy chain CDR3 | aCD25-a-674-HCDR3 |
| 5 | aCD25-a-674 variable heavy chain CDR 1, 2, 3 and FR 1, 2, 3, 4 | aCD25-a-674-HCDR123; variable heavy chain sequence of aCD25-a-674 |
| 6 | aCD25-a-674 variable light chain CDR1 | aCD25-a-674-LCDR1 |
| 7 | aCD25-a-674 variable light chain CDR2 | aCD25-a-674-LCDR2 |
| 8 | aCD25-a-674 variable light chain CDR3 | aCD25-a-674-LCDR3 |
| 9 | aCD25-a-674 variable light chain CDR 1, 2, 3 and FR 1, 2, 3, 4 | aCD25-a-674-LCDR123; variable light chain sequence of aCD25-a-674 |
| 10 | Epitope | aCD25ep-a |
| 11 | Epitope | aCD25ep-b |

EQUIVALENTS AND SCOPE

Those skilled in the art will appreciate that the present invention is defined by the appended claims and not by the Examples or other description of certain embodiments included herein.

Similarly, the singular forms "a", "an", and "the" include plural referents unless the context clearly dictates otherwise.

Unless defined otherwise above, all technical and scientific terms used herein have the same meaning as commonly understood by one of ordinary skill in the art to which this invention belongs. Any methods and materials similar or equivalent to those described herein can also be used in the practice or testing of the present invention. Generally, nomenclatures used in connection with, and techniques of, cell and tissue culture, molecular biology, immunology, genetics and protein and nucleic acid chemistry described herein are those well known and commonly used in the art, or according to manufacturers specifications.

All publications mentioned herein are incorporated herein by reference to disclose and describe the methods and/or materials in connection with which the publications are cited.

REFERENCES

Barnard G C et al., 2010. J Ind Microbiol Biotechnol. 37:961-71.
Beck A et al., 2017. Nat Rev Drug Discov. 16:315-337.
Bielekova B., 2013. Neurotherapeutics, 10(1):55-67
Dantal J et al., 1991, Transplantation 52:110-5
Estep P et al., 2013 MAbs. 5(2):270-8.
Kearns J D et al., 2015. Mol Cancer Ther. 14:1625-36.
Kijanka M et al., 2015. Nanomedicine. 10:161-174.
Langedijk J P et al., 2011. Analytical Biochemistry. 417: 149-155.
Liu L, 2015. J Pharm Sci. 104:1866-84.
Liu Y et al., 2014. MAbs. 6:483-92.
Lowenthal J. W et al., 1985. J. Immunol., 135, 3988-3994
Moreau, J.-L et al., 1987. Eur. J. Immunol. 17,929-935;
Onishi H et al; 2012 Anticanc. Res. 32, 997-1003
Queen C et al., 1989. PNAS. 86(24):10029-10033
Redman J M et al., 2015. Mol Immunol. 67: 28-45.
Setiady Y et al., 2010. Eur J Immunol. 40:780-6),
Shang B et al., 2015, Sci Rep. 5:15179
Siegel R W et al., 2004. J Immunol Methods. 286:141-53.
Sliwkowski M & Mellman I, 2013. Science. 341:1192-8.
Timmermann P et al., 2007, J. Mol. Recognit., 20, 283-99.
Volk H D et al., 1989 Clin. exp. Immunol. 76, 121-5
Vazquez-Lombardi R et al., 2015. Drug Discov Today. 20:1271-83.
Xu Y et al., 2013. Protein Eng Des Sel. 26:663-70
Smyth M et al., 2014, Immunol Cell Biol. 92, 473-4
Elpek et al., 2007 J Immunol. 178(11):6840-8;
Golgher et al., 2002 Eur J Immunol. 32(11):3267-75;
Jones et al., 2002; Cancer Immun. 22; 2:1
Onizuka et al., 1999 Cancer Res. 59(13):3128-33;
Shimizu et al., 1999 J Immunol. 163(10):5211-8
Hodi et al., 2008, Proc. Natl. Acad. Sci. USA, 105, 3005-3010
Quezada et al., 2006, J Clin Invest. 116(7):1935-45
Vargas A et al., 2017, Immunity, 46(4):577-586)
Kohm A et al., 2006, J Immunol. 176: 3301-5;
Hallett W et al., 2008. Biol Blood Marrow Transplant 14:1088-1099;
Fecci P et al., 2006 Clin Cancer Res. 12:4294-4305;
McNeill A et al., 2007. Scand J Immunol 65: 63-9;
Couper K et al., 2007. J Immunol. 178: 4136-4146;
O'Mahony D et al, 2008, Blood, 112(11), 231;
Oh et al, 2017, Oncotarget 8(29) 47440-4753;
Kreitman R J et al, 2016, Clin Cancer Res, 22(2) 310-318;
Flynn M J et al 2016, Mol Cancer Ther 15(11) 2709-2721;
Ellington et al. Nature. 1990; 346(6287): 818-822;
Tuerk et al., Science. 1990; 249(4968):505-510;
Ni et al., Curr Med Che 2011; 18(27):4206-14.
Jarasch A et al, Pharm Sci. 2015 June;104(6):1885-1898;
Rajpal et al., Proc Natl Acad Sci USA, 2005, 102(24):8466-71;
Steinwand et al., MAbs, 2014, 6(1):204-18

SEQUENCE LISTING

<160> NUMBER OF SEQ ID NOS: 11

<210> SEQ ID NO 1
<211> LENGTH: 272
<212> TYPE: PRT
<213> ORGANISM: homo sapiens

<400> SEQUENCE: 1

Met Asp Ser Tyr Leu Leu Met Trp Gly Leu Leu Thr Phe Ile Met Val
1               5                   10                  15

Pro Gly Cys Gln Ala Glu Leu Cys Asp Asp Pro Pro Glu Ile Pro
            20                  25                  30

His Ala Thr Phe Lys Ala Met Ala Tyr Lys Glu Gly Thr Met Leu Asn
                35                  40                  45

Cys Glu Cys Lys Arg Gly Phe Arg Arg Ile Lys Ser Gly Ser Leu Tyr
        50                  55                  60

Met Leu Cys Thr Gly Asn Ser Ser His Ser Ser Trp Asp Asn Gln Cys
65                  70                  75                  80

Gln Cys Thr Ser Ser Ala Thr Arg Asn Thr Thr Lys Gln Val Thr Pro
                85                  90                  95

Gln Pro Glu Glu Gln Lys Glu Arg Lys Thr Thr Glu Met Gln Ser Pro
            100                 105                 110

Met Gln Pro Val Asp Gln Ala Ser Leu Pro Gly His Cys Arg Glu Pro
        115                 120                 125

Pro Pro Trp Glu Asn Glu Ala Thr Glu Arg Ile Tyr His Phe Val Val
    130                 135                 140

Gly Gln Met Val Tyr Tyr Gln Cys Val Gln Gly Tyr Arg Ala Leu His
145                 150                 155                 160

Arg Gly Pro Ala Glu Ser Val Cys Lys Met Thr His Gly Lys Thr Arg
                165                 170                 175

Trp Thr Gln Pro Gln Leu Ile Cys Thr Gly Glu Met Glu Thr Ser Gln
            180                 185                 190

Phe Pro Gly Glu Glu Lys Pro Gln Ala Ser Pro Glu Gly Arg Pro Glu
        195                 200                 205

Ser Glu Thr Ser Cys Leu Val Thr Thr Thr Asp Phe Gln Ile Gln Thr
    210                 215                 220

Glu Met Ala Ala Thr Met Glu Thr Ser Ile Phe Thr Thr Glu Tyr Gln
225                 230                 235                 240

Val Ala Val Ala Gly Cys Val Phe Leu Leu Ile Ser Val Leu Leu Leu
                245                 250                 255

Ser Gly Leu Thr Trp Gln Arg Arg Gln Arg Lys Ser Arg Arg Thr Ile
            260                 265                 270

<210> SEQ ID NO 2
<211> LENGTH: 9
<212> TYPE: PRT
<213> ORGANISM: homo sapiens

<400> SEQUENCE: 2

Tyr Thr Phe Thr Ser Tyr Tyr Met His
1               5

<210> SEQ ID NO 3
<211> LENGTH: 17
<212> TYPE: PRT
<213> ORGANISM: homo sapiens

<400> SEQUENCE: 3

```
Ile Ile Asn Pro Ser Gly Gly Ser Thr Ser Tyr Ala Gln Lys Phe Gln
1               5                   10                  15

Gly

<210> SEQ ID NO 4
<211> LENGTH: 15
<212> TYPE: PRT
<213> ORGANISM: homo sapiens

<400> SEQUENCE: 4

Ala Arg Gly Gly Ala Glu Tyr Ile Pro Ala Glu Tyr Phe Gln His
1               5                   10                  15

<210> SEQ ID NO 5
<211> LENGTH: 122
<212> TYPE: PRT
<213> ORGANISM: homo sapiens

<400> SEQUENCE: 5

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Gly Ala Glu Tyr Ile Pro Ala Glu Tyr Phe Gln His Trp
            100                 105                 110

Gly Gln Gly Thr Leu Val Thr Val Ser Ser
        115                 120

<210> SEQ ID NO 6
<211> LENGTH: 11
<212> TYPE: PRT
<213> ORGANISM: homo sapiens

<400> SEQUENCE: 6

Arg Ala Ser Gln Ser Val Ser Ser Tyr Leu Ala
1               5                   10

<210> SEQ ID NO 7
<211> LENGTH: 7
<212> TYPE: PRT
<213> ORGANISM: homo sapiens

<400> SEQUENCE: 7

Asp Ala Ser Asn Arg Ala Thr
1               5

<210> SEQ ID NO 8
<211> LENGTH: 8
<212> TYPE: PRT
<213> ORGANISM: homo sapiens

<400> SEQUENCE: 8
```

```
Gln Gln Arg Pro Phe Leu Pro Thr
1               5

<210> SEQ ID NO 9
<211> LENGTH: 106
<212> TYPE: PRT
<213> ORGANISM: homo sapiens

<400> SEQUENCE: 9

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Pro Phe Leu Pro Thr
                85                  90                  95

Phe Gly Gly Gly Thr Lys Val Glu Ile Lys
            100                 105

<210> SEQ ID NO 10
<211> LENGTH: 11
<212> TYPE: PRT
<213> ORGANISM: Homo sapiens

<400> SEQUENCE: 10

Arg Trp Thr Gln Pro Gln Leu Ile Cys Thr Gly
1               5                   10

<210> SEQ ID NO 11
<211> LENGTH: 9
<212> TYPE: PRT
<213> ORGANISM: Homo sapiens

<400> SEQUENCE: 11

Tyr Gln Cys Val Gln Gly Tyr Arg Ala
1               5
```

The invention claimed is:

1. An antibody or antigen-binding fragment comprising:
   a) aCD25-a-674-HCDR3 amino acid sequence (SEQ ID NO: 4) as variable heavy chain complementarity determining region 3;
   b) aCD25-a-674-HCDR2 amino acid sequence (SEQ ID NO: 3) as variable heavy chain complementarity determining region 2;
   c) aCD25-a-674-HCDR1 amino acid sequence (SEQ ID NO: 2) as variable heavy chain complementarity determining region 1;
   d) aCD25-a-674-LCDR1 amino acid sequence (SEQ ID NO: 6) as variable light chain complementarity determining region 1;
   e) aCD25-a-674-LCDR2 amino acid sequence (SEQ ID NO: 7) as variable light chain complementarity determining region 2; and
   f) aCD25-a-674-LCDR3 amino acid sequence (SEQ ID NO: 8) as variable light chain complementarity determining region 3.

2. The antibody or antigen-binding fragment of claim 1, wherein the antibody or antigen-binding fragment comprises a variable heavy chain sequence having at least 95% sequence identity to the variable heavy chain region sequence of aCD25-a-674-HCDR123 amino acid sequence (SEQ ID NO: 5).

3. The antibody or antigen-binding fragment of claim 1, wherein the antibody or antigen-binding fragment comprises a variable light chain sequence having at least 95% sequence identity to the variable light chain region sequence of aCD25-a-674-LCDR123 amino acid sequence (SEQ ID NO: 9).

4. The antibody or antigen-binding fragment of claim 1, wherein the antibody or antigen-binding fragment is a monoclonal antibody, a domain antibody, a single chain antibody, a Fab fragment, a F(ab')2 fragment, a single chain variable fragment (scFv), a scFv-Fc fragment, a single chain antibody (scAb), or a single domain antibody.

5. The antibody or antigen-binding fragment of claim 1, wherein the antibody is selected from the group consisting of IgG1, IgG2, IgG3, and IgG4 isotype antibodies.

6. The antibody or antigen-binding fragment of claim 1, wherein the antibody or antigen-binding fragment is comprised in a bispecific antibody, a multispecific antibody, or an immunoconjugate further comprising a therapeutic or diagnostic agent.

7. The antibody or antigen-binding fragment of claim 1, wherein the antibody or antigen-binding fragment binds the extracellular domain of human CD25.

8. The antibody or antigen-binding fragment of claim 1, wherein the antibody or antigen-binding fragment binds cells expressing human CD25 on their surface and is an anti-CD25Antibody Agent.

9. The antibody or antigen-binding fragment of claim 1, wherein the antibody or antigen-binding fragment does not inhibit the binding of Interleukin-2(IL-2) to CD25.

10. The antibody or antigen-binding fragment of claim 1, wherein the antibody or antigen-binding fragment does not inhibit the signalling of Interleukin-2(IL-2) via CD25.

11. The antibody or an antigen-binding fragment of claim 1 wherein the antibody or antigen-binding fragment is afucosylated.

12. A nucleic acid molecule encoding the antibody or antigen-binding fragment of claim 1.

13. A nucleic acid vector comprising the nucleic acid molecule of claim 12.

14. A host cell comprising the nucleic acid vector of claim 13.

15. A composition comprising an antibody or antigen-binding fragment of comprising:
 a) aCD25-a-674-HCDR3amino acid sequence (SEQ ID NO: 4) as variable heavy chain complementarity determining region 3;
 b) aCD25-a-674-HCDR2amino acid sequence (SEQ ID NO: 3) as variable heavy chain complementarity determining region 2;
 c) aCD25-a-674-HCDR1amino acid sequence (SEQ ID NO: 2) as variable heavy chain complementarity determining region 1;
 d) aCD25-a-674-LCDR1amino acid sequence (SEQ ID NO: 6) as variable light chain complementarity determining region 1;
 e) aCD25-a-674-LCDR2amino acid sequence (SEQ ID NO: 7) as variable light chain complementarity determining region 2;
 f) aCD25-a-674-LCDR3amino acid sequence (SEQ ID NO: 8) as variable light chain complementarity determining region 3; and
 a pharmaceutically acceptable carrier or excipient.

16. A method of treating cancer in a subject, comprising administering to the subject an effective amount of the composition of claim 15.

17. The method of claim 16, further comprising administering, simultaneously or sequentially in any order, a second agent to the subject.

18. The method of claim 17 wherein the second agent is an immune checkpoint inhibitor or a cancer vaccine.

19. The method of claim 18 wherein the second agent is an immune checkpoint inhibitor, wherein the immune check point inhibitor is a PD-1antagonist.

20. The method of claim 19 wherein the PD-1antagonist is an anti-PD-1antibody or an anti-PD-L1antibody.

21. A method of depleting regulatory T cells in a tumour in a subject comprising the step of administering an effective amount of the composition of claim 15.

22. The method according to claim 21, wherein the subject has a solid tumor.

23. The method according to claim 21, wherein the subject has a haematological cancer tumor.

24. The method of claim 16 wherein the subject has a solid tumor.

25. The method of claim 16 wherein the subject has a haematological cancer tumour.

* * * * *